US006017903A

United States Patent [19]
Slusher et al.

[11] Patent Number: 6,017,903
[45] Date of Patent: *Jan. 25, 2000

[54] PHARMACEUTICAL COMPOSITIONS AND METHODS OF TREATING A GLUTAMATE ABNORMALITY AND EFFECTING A NEURONAL ACTIVITY IN AN ANIMAL USING NAALADASE INHIBITORS

[75] Inventors: Barbara S. Slusher, Kingsville; Paul F. Jackson, Bel Air; Kevin L. Tays, Elkridge; Keith M. Maclin, Baltimore, all of Md.

[73] Assignee: Guilford Pharmaceuticals Inc., Baltimore, Md.

[ * ] Notice: This patent is subject to a terminal disclaimer.

[21] Appl. No.: 08/884,479

[22] Filed: Jun. 27, 1997

Related U.S. Application Data

[63] Continuation-in-part of application No. 08/718,703, Sep. 27, 1996, Pat. No. 5,824,662, and a continuation-in-part of application No. 08/842,360, Apr. 24, 1997, and a continuation-in-part of application No. 08/863,624, May 27, 1997, and a continuation-in-part of application No. 08/858,985, May 27, 1997.

[51] Int. Cl.[7] ................................................. A61K 31/66
[52] U.S. Cl. ............................ 514/75; 514/80; 514/89; 514/95; 514/99
[58] Field of Search ............................... 514/75, 80, 89, 514/95, 99

[56] References Cited

U.S. PATENT DOCUMENTS

| | | |
|---|---|---|
| H1312 | 5/1994 | Coughlin et al. . |
| 4,671,958 | 6/1987 | Rodwell et al. . |
| 4,741,900 | 5/1988 | Alvarez et al. . |
| 4,853,326 | 8/1989 | Quash et al. . |
| 4,867,973 | 9/1989 | Goers et al. . |
| 4,906,779 | 3/1990 | Weber et al. . |
| 4,918,064 | 4/1990 | Cordi et al. . |
| 4,937,183 | 6/1990 | Ultee et al. . |
| 4,950,738 | 8/1990 | King et al. . |
| 4,959,493 | 9/1990 | Ohfume et al. . |
| 4,966,999 | 10/1990 | Coughlin et al. . |
| 4,977,155 | 12/1990 | Jacobsen et al. . |
| 4,980,356 | 12/1990 | Audiau et al. . |
| 4,994,446 | 2/1991 | Sokolovsky et al. . |
| 5,011,834 | 4/1991 | Weber et al. . |
| 5,026,717 | 6/1991 | Audiau et al. . |
| 5,047,227 | 9/1991 | Rodwell et al. . |
| 5,057,516 | 10/1991 | Jacobsen et al. . |
| 5,068,238 | 11/1991 | Jimonet . |
| 5,075,306 | 12/1991 | Jacobsen et al. . |
| 5,079,250 | 1/1992 | Jacobsen et al. . |
| 5,093,525 | 3/1992 | Weber et al. . |
| 5,109,001 | 4/1992 | Jacobsen et al. . |
| 5,130,330 | 7/1992 | Bowen et al. . |
| 5,135,080 | 8/1992 | Miller et al. . |
| 5,140,104 | 8/1992 | Coughlin et al. . |
| 5,145,862 | 9/1992 | Aizenman et al. . |
| 5,156,840 | 10/1992 | Goers et al. . |
| 5,158,976 | 10/1992 | Rosenberg . |
| 5,162,504 | 11/1992 | Horoszewicz . |
| 5,162,512 | 11/1992 | King et al. . |
| 5,177,109 | 1/1993 | Cordi et al. . |
| 5,190,976 | 3/1993 | Weber et al. . |
| 5,196,439 | 3/1993 | Higurashi et al. . |
| 5,196,510 | 3/1993 | Rodwell et al. . |
| 5,236,940 | 8/1993 | Phone-Poulenc Sante . |
| 5,242,915 | 9/1993 | Ueda et al. . |
| 5,262,568 | 11/1993 | Weber et al. . |
| 5,283,244 | 2/1994 | Yamnouchi . |
| 5,284,867 | 2/1994 | Benita et al. . |
| 5,292,765 | 3/1994 | Choi et al. . |
| 5,326,856 | 7/1994 | Coughlin et al. . |
| 5,336,689 | 8/1994 | Weber et al. . |
| 5,340,824 | 8/1994 | Gueremy et al. . |
| 5,356,902 | 10/1994 | Orstein . |
| 5,403,837 | 4/1995 | Audiau et al. . |
| 5,403,861 | 4/1995 | Fischer et al. . |
| 5,434,159 | 7/1995 | DeHaven-Hudkins et al. . |
| 5,438,130 | 8/1995 | McCormick et al. . |
| 5,449,761 | 9/1995 | Belinka, Jr. et al. . |
| 5,459,037 | 10/1995 | Erlander et al. . |
| 5,473,077 | 12/1995 | Monn et al. . |
| 5,474,547 | 12/1995 | Aebischer et al. . |
| 5,478,859 | 12/1995 | Drejer et al. . |
| 5,486,620 | 1/1996 | Monn . |
| 5,489,525 | 2/1996 | Pastan . |
| 5,489,717 | 2/1996 | Bigge et al. . |
| 5,491,241 | 2/1996 | Monn et al. . |
| 5,495,042 | 2/1996 | Belinka, Jr. et al. . |

(List continued on next page.)

FOREIGN PATENT DOCUMENTS

| | | |
|---|---|---|
| 8937077 | 1/1990 | Australia . |
| 8946189 | 6/1990 | Australia . |
| 9054488 | 11/1990 | Australia . |
| 9066624 | 5/1991 | Australia . |
| 9067393 | 5/1991 | Australia . |

(List continued on next page.)

OTHER PUBLICATIONS

Slusher et al., "Rat Brain N–Acetylated α–Linked Acidic Dipeptidase Activity," J. Bio. Chem., 1990, 265(34), 21297–21301.

Tsai et al., 61st Salmon Lecturer of the New York Academy of Medicine, Dec. 2–3, 1993, "Changes of Excitatory Neurotransmitter Metabolism in Schizophrenic Brains.".

Tsai et al., "Reductions in acidic amino acids and N–acetylaspartylglutamate in amyotrophic lateral sclerosis CNS," Brain Research, 556, 1991, 151–156.

(List continued on next page.)

*Primary Examiner*—Keith D. MacMillan
*Attorney, Agent, or Firm*—Gary M. Nath; Suet M. Chong; Nath & Associates

[57] ABSTRACT

The present invention relates to a method of treating a glutamate abnormality and a method of effecting a neuronal activity in an animal using a NAALADase inhibitor, and a pharmaceutical composition comprising an effective amount of a NAALADase inhibitor for treating a glutamate abnormality and effecting a neuronal activity in an animal.

40 Claims, 14 Drawing Sheets

U.S. PATENT DOCUMENTS

| | | |
|---|---|---|
| 5,500,420 | 3/1996 | Maiese . |
| 5,502,166 | 3/1996 | Mishina . |
| 5,521,215 | 5/1996 | Benita et al. . |
| 5,523,307 | 6/1996 | Higurashi et al. . |
| 5,527,885 | 6/1996 | Coughlin et al. . |
| 5,536,721 | 7/1996 | Faarup et al. . |
| 5,538,866 | 7/1996 | Israeli et al. . |

FOREIGN PATENT DOCUMENTS

| | | |
|---|---|---|
| 9175796 | 9/1991 | Australia . |
| 9185131 | 3/1992 | Australia . |
| 9187666 | 5/1992 | Australia . |
| 9189297 | 5/1992 | Australia . |
| 645766 | 1/1994 | Australia . |
| 9345401 | 1/1994 | Australia . |
| 9464063 | 2/1994 | Australia . |
| 9348014 | 3/1994 | Australia . |
| 9461310 | 8/1994 | Australia . |
| 652555 | 9/1994 | Australia . |
| 947047 | 12/1994 | Australia . |
| 656154 | 1/1995 | Australia . |
| 9471882 | 1/1995 | Australia . |
| 9510551 | 5/1995 | Australia . |
| 9479151 | 6/1995 | Australia . |
| 9514474 | 7/1995 | Australia . |
| 9519457 | 10/1995 | Australia . |
| 9522125 | 10/1995 | Australia . |
| 9528530 | 2/1996 | Australia . |
| 9530357 | 3/1996 | Australia . |
| 9532781 | 3/1996 | Australia . |
| 9533251 | 3/1996 | Australia . |
| 9533252 | 3/1996 | Australia . |
| 9534142 | 3/1996 | Australia . |
| 9534186 | 3/1996 | Australia . |
| 9005758 | 9/1991 | Brazil . |
| 94048098 | 8/1995 | Brazil . |
| 9503638 | 5/1996 | Brazil . |
| 2005590 | 6/1990 | Canada . |
| 2005592 | 6/1990 | Canada . |
| 2029419 | 5/1991 | Canada . |
| 2029974 | 5/1991 | Canada . |
| 1305056 | 7/1992 | Canada . |
| 1306995 | 9/1992 | Canada . |
| 2068918 | 11/1992 | Canada . |
| 1326670 | 2/1994 | Canada . |
| 2117852 | 4/1995 | Canada . |
| 1369074 | 6/1995 | Canada . |
| 2156024 | 2/1996 | Canada . |
| 2157248 | 3/1996 | Canada . |
| 9605828 | 2/1996 | Cocos (Keeling) Islands . |
| 9402947 | 12/1995 | Czech Rep. . |
| 9502221 | 3/1996 | Czech Rep. . |
| 9502074 | 5/1996 | Czech Rep. . |
| 8806621 | 5/1989 | Denmark . |
| 8906334 | 6/1990 | Denmark . |
| 169383 | 10/1994 | Denmark . |
| 270290 | 6/1988 | European Pat. Off. . |
| 313002 | 4/1989 | European Pat. Off. . |
| 31809 | 5/1989 | European Pat. Off. . |
| 342558 | 11/1989 | European Pat. Off. . |
| 348872 | 1/1990 | European Pat. Off. . |
| 370499 | 5/1990 | European Pat. Off. . |
| 374040 | 6/1990 | European Pat. Off. . |
| 374041 | 6/1990 | European Pat. Off. . |
| 433112 | 6/1991 | European Pat. Off. . |
| 470127 | 2/1992 | European Pat. Off. . |
| 486621 | 5/1992 | European Pat. Off. . |
| 497895 | 8/1992 | European Pat. Off. . |
| 509066 | 10/1992 | European Pat. Off. . |
| 375510 | 11/1992 | European Pat. Off. . |
| 517852 | 12/1992 | European Pat. Off. . |
| 519602 | 12/1992 | European Pat. Off. . |
| 528968 | 3/1993 | European Pat. Off. . |
| 530058 | 3/1993 | European Pat. Off. . |
| 556393 | 8/1993 | European Pat. Off. . |
| 516748 | 4/1994 | European Pat. Off. . |
| 592571 | 4/1994 | European Pat. Off. . |
| 594597 | 5/1994 | European Pat. Off. . |
| 408437 | 6/1994 | European Pat. Off. . |
| 532602 | 8/1994 | European Pat. Off. . |
| 629615 | 12/1994 | European Pat. Off. . |
| 600278 | 1/1995 | European Pat. Off. . |
| 633779 | 1/1995 | European Pat. Off. . |
| 427518 | 3/1995 | European Pat. Off. . |
| 648762 | 4/1995 | European Pat. Off. . |
| 667340 | 8/1995 | European Pat. Off. . |
| 669397 | 8/1995 | European Pat. Off. . |
| 688319 | 12/1995 | European Pat. Off. . |
| 318029 | 2/1996 | European Pat. Off. . |
| 696577 | 2/1996 | European Pat. Off. . |
| 699678 | 3/1996 | European Pat. Off. . |
| 703218 | 3/1996 | European Pat. Off. . |
| 705100 | 4/1996 | European Pat. Off. . |
| 707644 | 4/1996 | European Pat. Off. . |
| 711755 | 5/1996 | European Pat. Off. . |
| 713703 | 5/1996 | European Pat. Off. . |
| 715851 | 6/1996 | European Pat. Off. . |
| 8903170 | 12/1989 | Finland . |
| 8905982 | 6/1990 | Finland . |
| 8905983 | 6/1990 | Finland . |
| 9005628 | 5/1991 | Finland . |
| 9301394 | 4/1993 | Finland . |
| 9301891 | 4/1993 | Finland . |
| 9301892 | 4/1993 | Finland . |
| 9301893 | 4/1993 | Finland . |
| 9404714 | 10/1994 | Finland . |
| 93106 | 11/1994 | Finland . |
| 93107 | 11/1994 | Finland . |
| 93108 | 11/1994 | Finland . |
| 93838 | 2/1995 | Finland . |
| 93839 | 2/1995 | Finland . |
| 93840 | 2/1995 | Finland . |
| 93841 | 2/1995 | Finland . |
| 9405704 | 6/1995 | Finland . |
| 9506353 | 12/1995 | Finland . |
| 9503837 | 2/1996 | Finland . |
| 9504066 | 3/1996 | Finland . |
| 9602000 | 5/1996 | Finland . |
| 2640622 | 6/1990 | France . |
| 2640624 | 6/1990 | France . |
| 2649701 | 1/1991 | France . |
| 2649703 | 1/1991 | France . |
| 2649705 | 1/1991 | France . |
| 2662160 | 11/1991 | France . |
| 2662694 | 12/1991 | France . |
| 2662695 | 12/1991 | France . |
| 2678619 | 1/1993 | France . |
| 2707880 | 1/1995 | France . |
| 2726271 | 5/1996 | France . |
| 290883 | 6/1991 | German Dem. Rep. . |
| 68903484 | 12/1992 | Germany . |
| 68905585 | 4/1993 | Germany . |
| 4212529 | 10/1993 | Germany . |
| 68909513 | 11/1993 | Germany . |
| 3886003 | 1/1994 | Germany . |
| 68912822 | 3/1994 | Germany . |
| 69009604 | 7/1994 | Germany . |
| 69103271 | 9/1994 | Germany . |
| 69017839 | 4/1995 | Germany . |
| 4410822 | 9/1995 | Germany . |
| 3854991 | 3/1996 | Germany . |
| 69210106 | 5/1996 | Germany . |

| Number | Date | Country |
|---|---|---|
| T53625 | 11/1990 | Hungary . |
| T54891 | 4/1991 | Hungary . |
| T55231 | 5/1991 | Hungary . |
| T55403 | 5/1991 | Hungary . |
| 208079 | 8/1993 | Hungary . |
| T64324 | 12/1993 | Hungary . |
| 210744 | 7/1995 | Hungary . |
| T69181 | 8/1995 | Hungary . |
| 62406 | 1/1995 | Ireland . |
| 62688 | 2/1995 | Ireland . |
| 64289 | 7/1995 | Ireland . |
| 64657 | 8/1995 | Ireland . |
| 84535 | 9/1992 | Israel . |
| 92710 | 6/1993 | Israel . |
| 92238 | 7/1995 | Israel . |
| 1217603 | 3/1990 | Italy . |
| 1238346 | 7/1993 | Italy . |
| 1135790 | 5/1989 | Japan . |
| 1316356 | 12/1989 | Japan . |
| 2017157 | 1/1990 | Japan . |
| 2193922 | 7/1990 | Japan . |
| 2223570 | 9/1990 | Japan . |
| 2223571 | 9/1990 | Japan . |
| 3170491 | 7/1991 | Japan . |
| 3209377 | 9/1991 | Japan . |
| 04178385 | 6/1992 | Japan . |
| 3517229 | 11/1992 | Japan . |
| 4346927 | 12/1992 | Japan . |
| 5501540 | 3/1993 | Japan . |
| 5239098 | 9/1993 | Japan . |
| 5506012 | 9/1993 | Japan . |
| 5507062 | 10/1993 | Japan . |
| 5507918 | 11/1993 | Japan . |
| 5508147 | 11/1993 | Japan . |
| 5509077 | 12/1993 | Japan . |
| 94517862 | 1/1994 | Japan . |
| 6062861 | 3/1994 | Japan . |
| 6157597 | 6/1994 | Japan . |
| 6228112 | 8/1994 | Japan . |
| 6508843 | 10/1994 | Japan . |
| 6321805 | 11/1994 | Japan . |
| 95049425 | 5/1995 | Japan . |
| 7149724 | 6/1995 | Japan . |
| 95068235 | 7/1995 | Japan . |
| 7196533 | 8/1995 | Japan . |
| 7267908 | 10/1995 | Japan . |
| 8034771 | 2/1996 | Japan . |
| 8081469 | 3/1996 | Japan . |
| 236057 | 9/1994 | New Zealand . |
| 8902680 | 1/1990 | Norway . |
| 8905030 | 7/1990 | Norway . |
| 8905032 | 7/1990 | Norway . |
| 9004921 | 5/1991 | Norway . |
| 173060 | 7/1993 | Norway . |
| 174200 | 12/1993 | Norway . |
| 174775 | 3/1994 | Norway . |
| 9404578 | 6/1995 | Norway . |
| 9504888 | 12/1995 | Norway . |
| 9503191 | 2/1996 | Norway . |
| 9503394 | 3/1996 | Norway . |
| 91010 | 12/1989 | Portugal . |
| 92604 | 6/1990 | Portugal . |
| 92606 | 6/1990 | Portugal . |
| 2223569 | 9/1990 | Portugal . |
| 96930 | 11/1991 | Portugal . |
| 8909551 | 9/1990 | South Africa . |
| 8908936 | 7/1991 | South Africa . |
| 9008914 | 9/1991 | South Africa . |
| 9101553 | 12/1991 | South Africa . |
| 9302553 | of 1993 | South Africa . |
| 9403744 | 6/1995 | South Africa . |
| 9502431 | 2/1996 | South Africa . |
| 2043070 | 12/1993 | Spain . |
| 2052954 | 7/1994 | Spain . |
| 2054068 | 8/1994 | Spain . |
| 2055365 | 8/1994 | Spain . |
| 2057901 | 10/1994 | Spain . |
| 2059636 | 11/1994 | Spain . |
| 2060635 | 12/1994 | Spain . |
| 2061782 | 12/1994 | Spain . |
| 2062794 | 12/1994 | Spain . |
| 2071786 | 7/1995 | Spain . |
| 9012575 | 11/1990 | WIPO . |
| 9102810 | 3/1991 | WIPO . |
| 9106536 | 5/1991 | WIPO . |
| 9112797 | 9/1991 | WIPO . |
| 9117984 | 11/1991 | WIPO . |
| 9118892 | 12/1991 | WIPO . |
| 9204023 | 3/1992 | WIPO . |
| 9217168 | 4/1992 | WIPO . |
| 9207562 | 5/1992 | WIPO . |
| 9207847 | 5/1992 | WIPO . |
| 9301194 | 1/1993 | WIPO . |
| 9320820 | 10/1993 | WIPO . |
| 9325203 | 12/1993 | WIPO . |
| 9401142 | 1/1994 | WIPO . |
| 9418172 | 1/1994 | WIPO . |
| 9403469 | 2/1994 | WIPO . |
| 9404698 | 3/1994 | WIPO . |
| 9415622 | 7/1994 | WIPO . |
| 9420470 | 9/1994 | WIPO . |
| 9427591 | 12/1994 | WIPO . |
| 9501429 | 1/1995 | WIPO . |
| 9513369 | 5/1995 | WIPO . |
| 95076 | 7/1995 | WIPO . |
| 9518154 | 7/1995 | WIPO . |
| 9525110 | 9/1995 | WIPO . |
| 9525721 | 9/1995 | WIPO . |
| 9605175 | 2/1996 | WIPO . |
| 9605818 | 2/1996 | WIPO . |
| 9606606 | 3/1996 | WIPO . |
| 9607405 | 3/1996 | WIPO . |
| 9613492 | 5/1996 | WIPO . |
| 9615099 | 5/1996 | WIPO . |
| 9615100 | 5/1996 | WIPO . |
| 9615108 | 5/1996 | WIPO . |
| 9617832 | 6/1996 | WIPO . |
| WO 96/26272 | 8/1996 | WIPO . |

OTHER PUBLICATIONS

Rothstein et al., "Abnormal Excitatory Amino Acid Metabolism in Amyotrophic Lateral Sclerosis," Ann Neurol, 1990, 28, 18–25.

Tsai et al., "Immunocytochemical Distribution of N–acetylaspartylglutamate in the Rat Forebrain and Glutamatergic Pathways," J. Chem. Neuroanatomy, 1993, vol. 6, 277–292.

Subasinghe et al., Synthesis of Acyclic and Dehydroaspartic Acid Analogues of Ac–Asp–Glu–OH and Their Inhibition of Rat Brain N–Acetylated α–Linked Acidic Dipeptidase (NAALA Dipeptidase), J. Med. Chem 1990, 33, 2734–2744.

Slusher et al., Immunocytochemical Localization of the N–Acetyl–Aspartyl–Glutamate (NAAG) Hydrolyzing Enzyme N–Acetylated α–Linked Acidic Dipeptidase (NAALADase), J. Comparative Neurology, 1992, 315:217–229.

Stauch et al., "The effects of N–acetylated alpha–linked acidic dipeptidase (NAALADase) inhibitors on [$^3$H]NAAG catabolism in vivo," Neuroscience Letters, 1989, 100, 295–300.

Meyerhoff et al., "Genetically epilepsy–prone rats have increased brain regional activity of an enzyme which liberates glutamate from N–acetyl–aspartyl–glutamate," Brain Research, 593, 1992, 140–143.

Meyerhoff et al., "Activity of NAAG–hydrolyzing enzyme in brain may affect seizure susceptibility in genetically epilepsy–prone rats," Molecular Neurobiology of Epilepsy (Epilepsy Res. Suppl. 9), 1992, Chap. 16, 163–172.

Vornov, J., "Toxic NMDA–Receptor Activation Occurs During Recovery in a Tissue Culture Model of Ischemia," J. Neurochemistry, 1995, 65(4), 1681–1691.

Slusher et al., "NAALADase: A Potential Regulator of Synaptic Glutamate," DuPont NEN Notes, Spring 1994.

Jackson et al., "Design Synthesis, and Biological Activity of a Potent Inhibitor of the Neuropeptidase N–Acetylated α–Linked Acidic Dipeptidase," J. Medicinal Chem., 1995.

Carter et al., "Prostate–specific membrane antigen is a hydrolase with substrate and pharmacologic characteristics of a neuorpeptidase," Proc. Natl, Acad, Sci. USA, 1996, vol. 93, 749–753.

Coyle et al. "N–Acetyl–aspartyl Glutamate Recent Developments," Excitatory Amino Acids, 1991, 69–77.

Koenig et al., "N–acetyl–aspartyl–glutamate (NAAG) elicits rapid increase in intraneuronal $Ca^{2+}$ in vitro," NeuroReport 5, 1063–1068, 1994.

Heston, W.D.W., "Potential Uses of Prostate Specific Membrane Antigen (PMSA): a Neurocarboxypeptidase and Membrane Folate Hydrolase," *Urologe* [A], v. 35, pp. 400–407 (1996).

Meyeroff, J. et al., "Genetically epilepsy prone rats have increased brain regional activity of an enzyme which liberates glutamate from N–acetyl–aspartyl–glutamate," *Brain Research*, 593 (1992).

Bhardwaj, A., "Striatal Nitric Oxide (NO) Production is Enhanced In Focal Cerebral Ischemia: An In Vivo Microdialysis Study," *Society for Neuroscience 1996 Abstract Form*, (1996).

Hurn, P., "Gender–Linked Injury After Focal Cerebral Ischemia," *Society for Neuroscience 1996 Abstract Form*, (1996).

Tsai, G. et al., "Changes of excitatory neurotransmitter metabolism in schizophrenic brains," *Salmon Lecturer of the New York Acadmey of Medicine* (Dec. 2–3, 1993).

Compound 3 is Neuroprotective When Administered Post-Ischemia

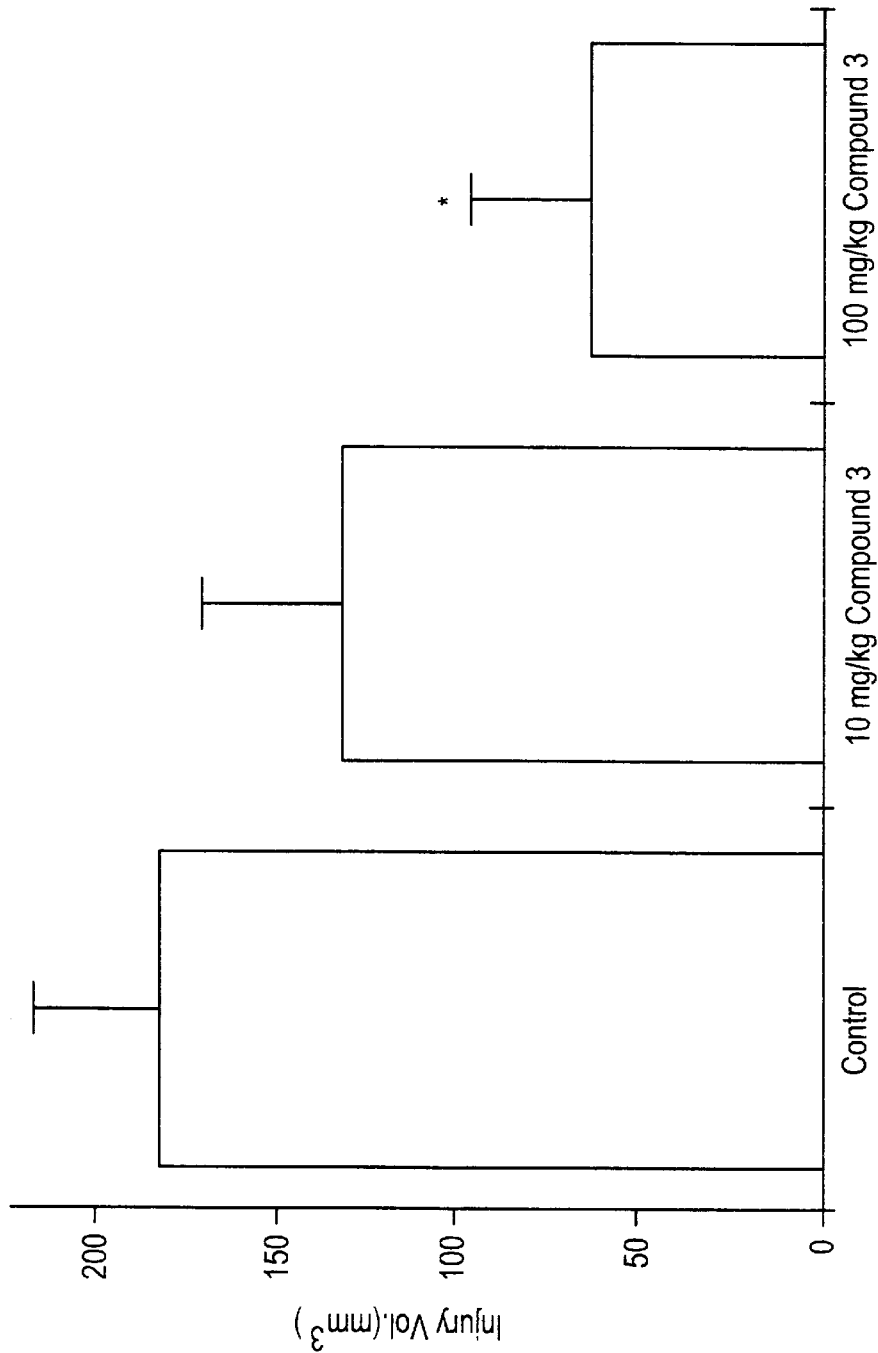

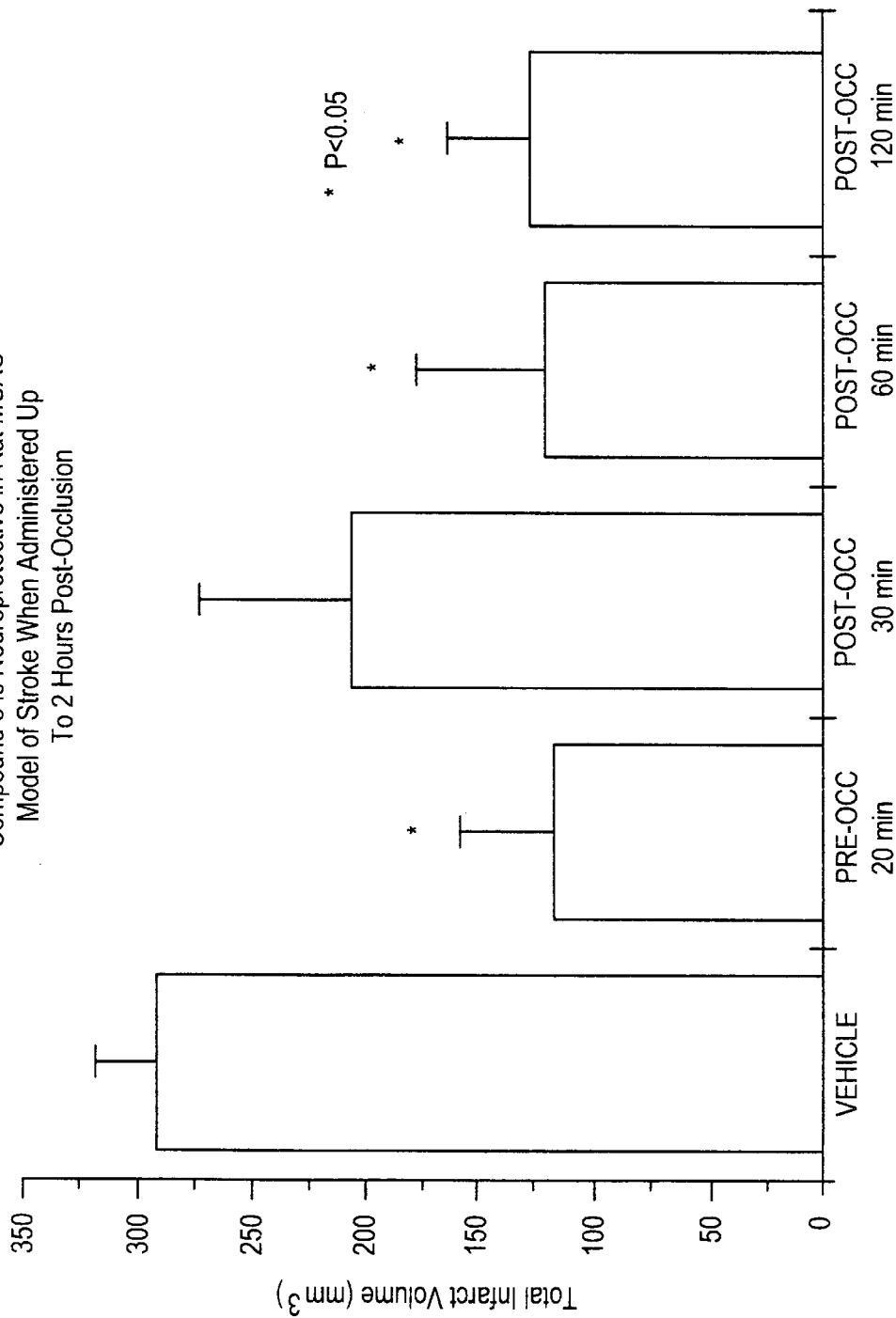

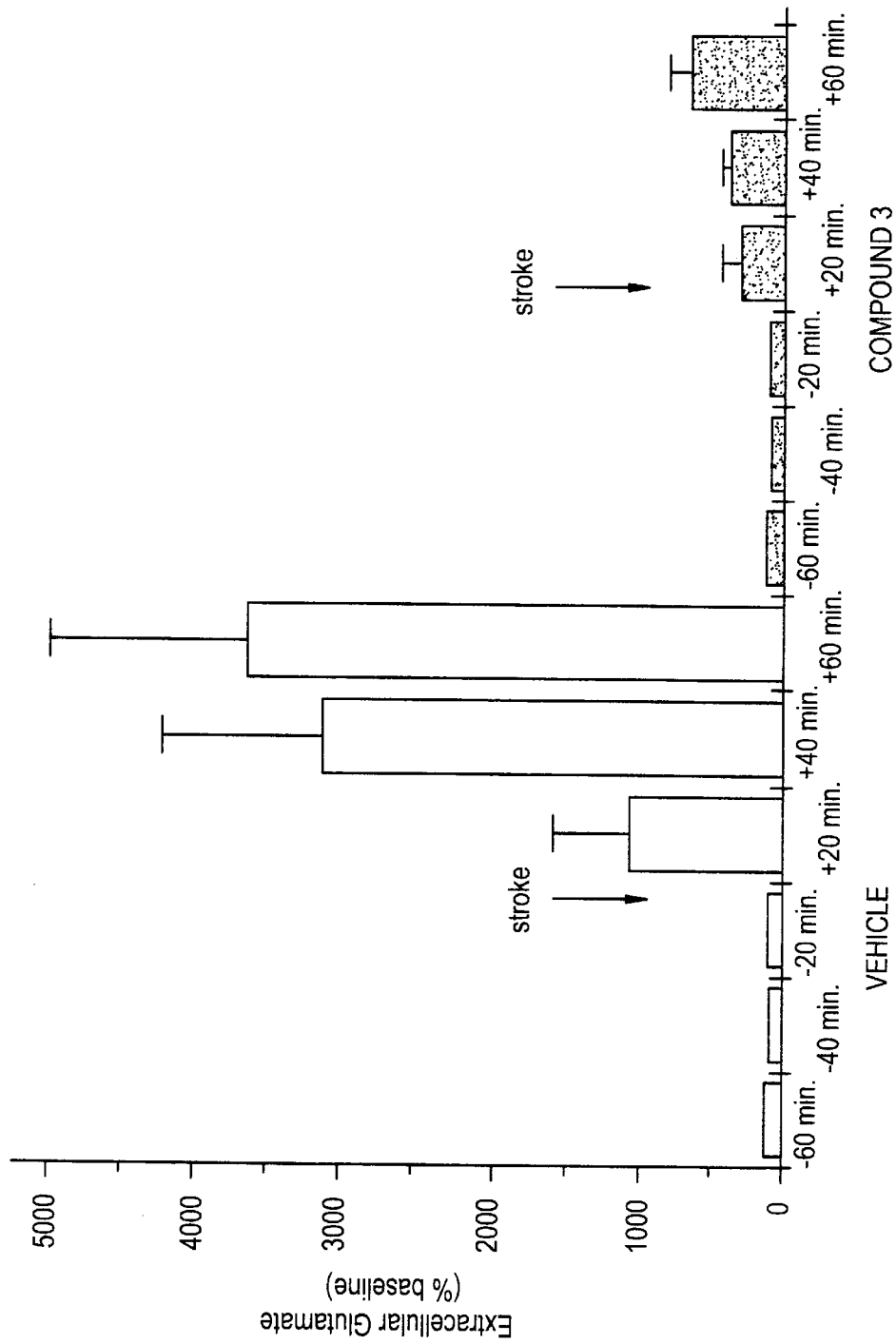

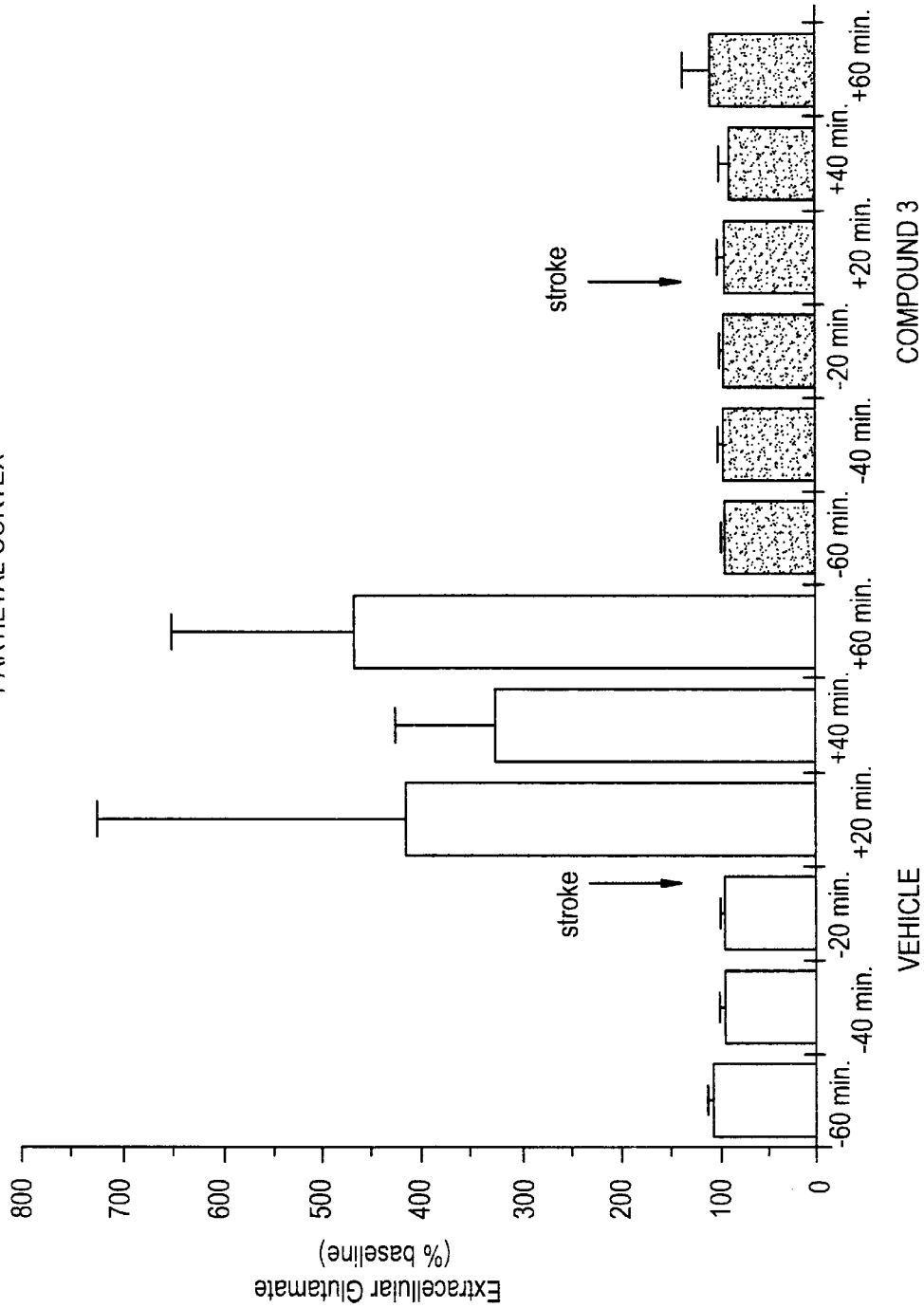

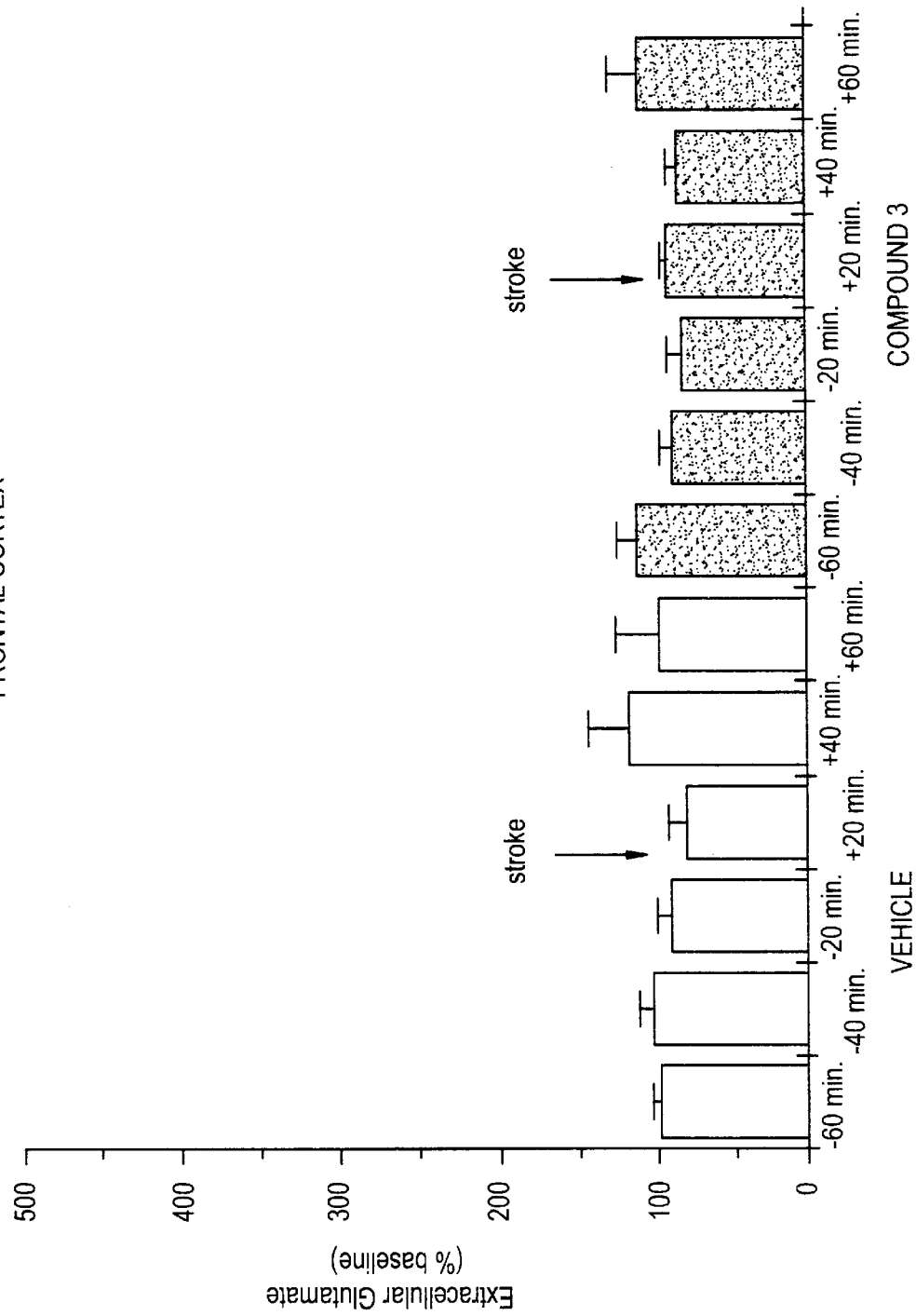

Compound 3 Administration
Following Sciatic Nerve Crush

Vehicle Polymer

Compound 3 Polymer
2ug drug/day

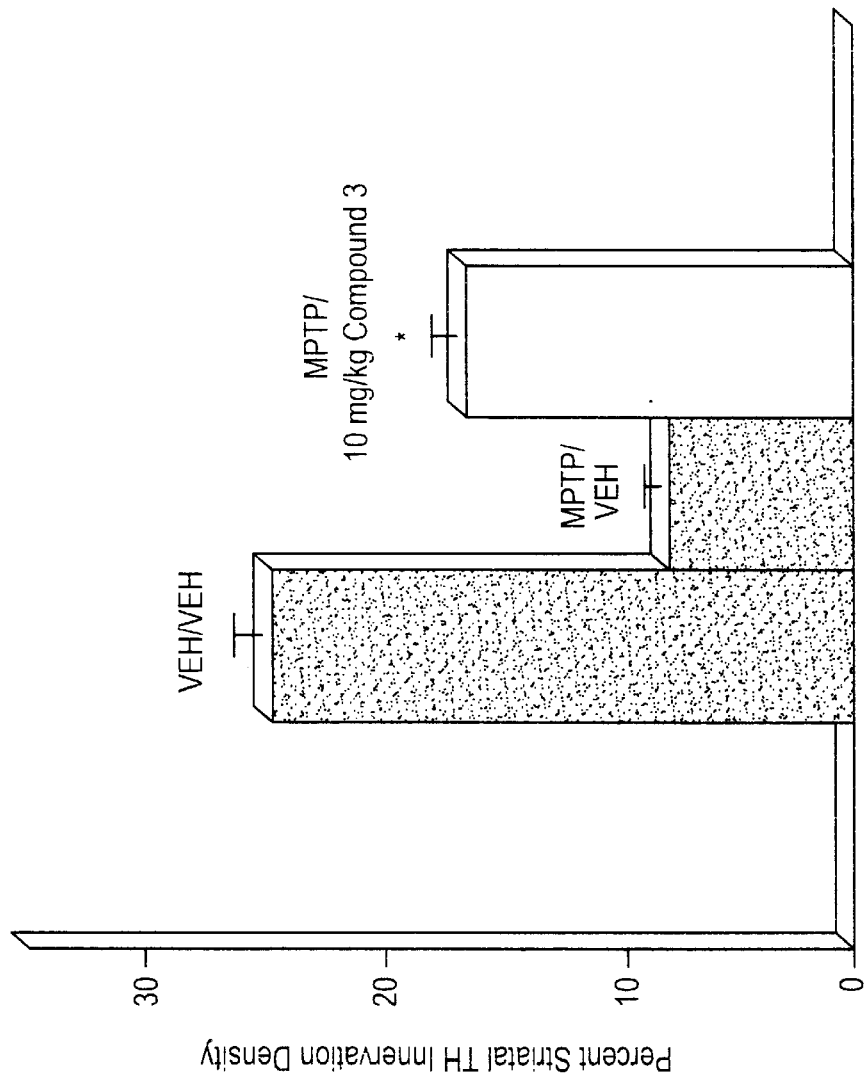

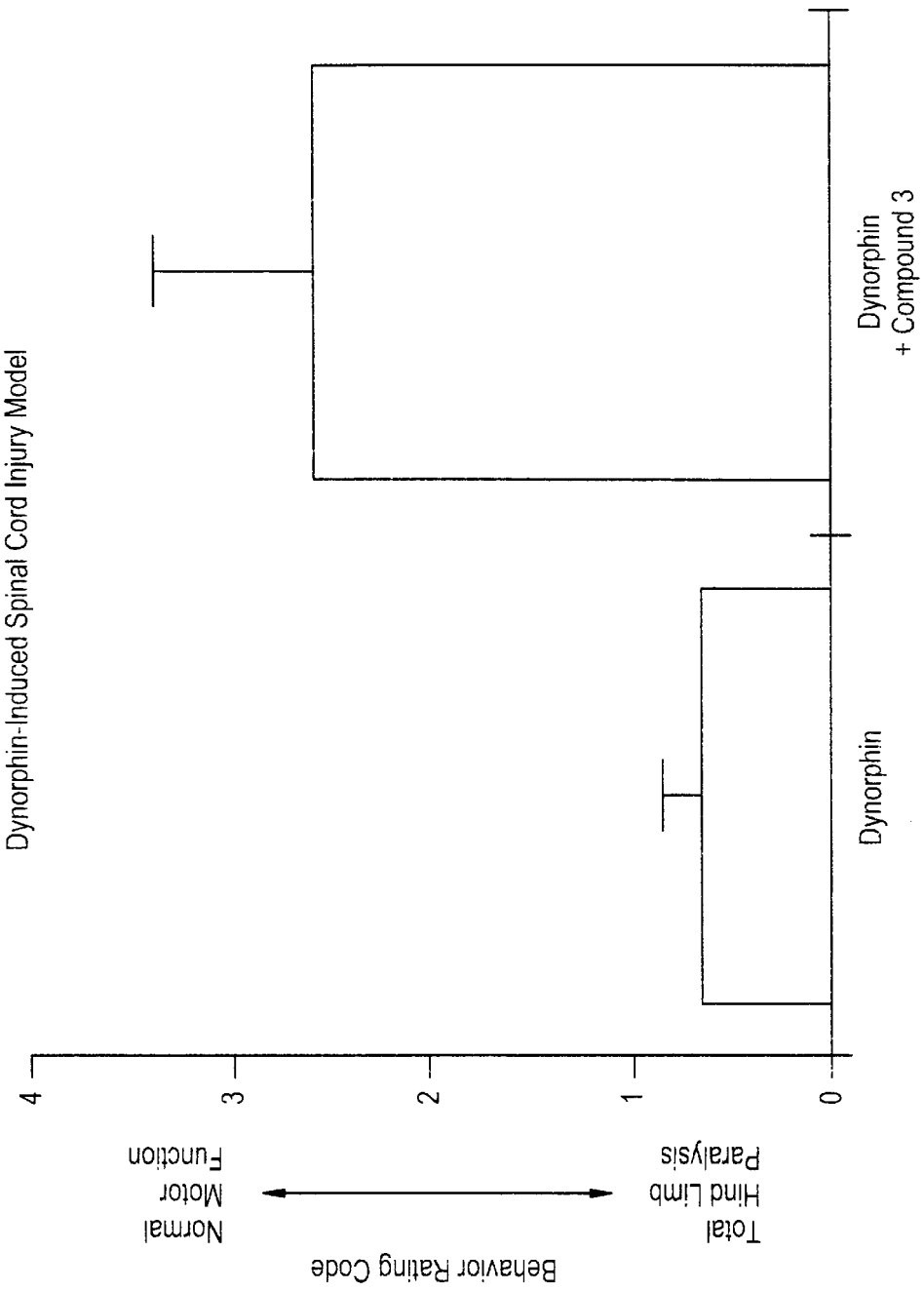

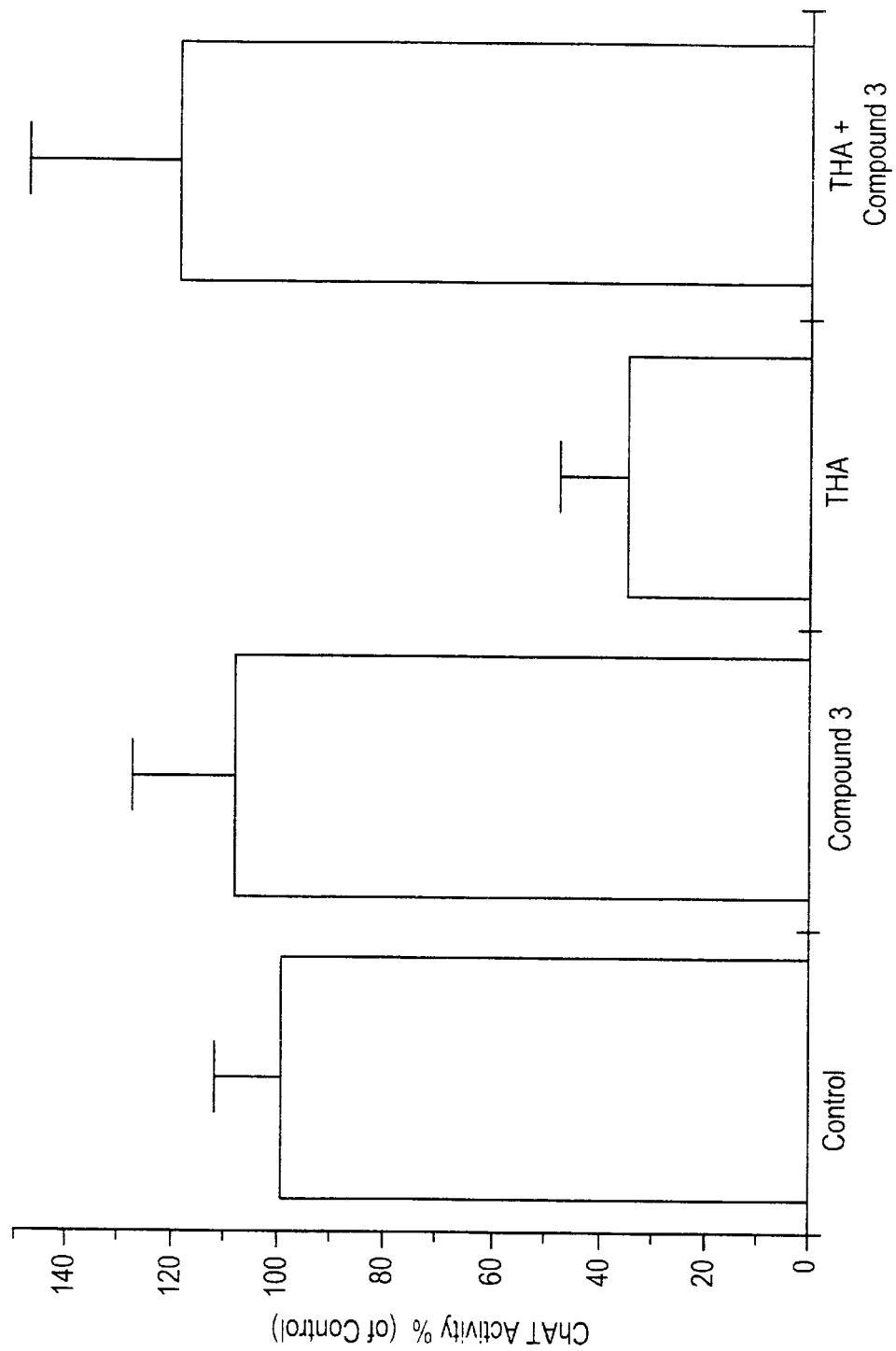

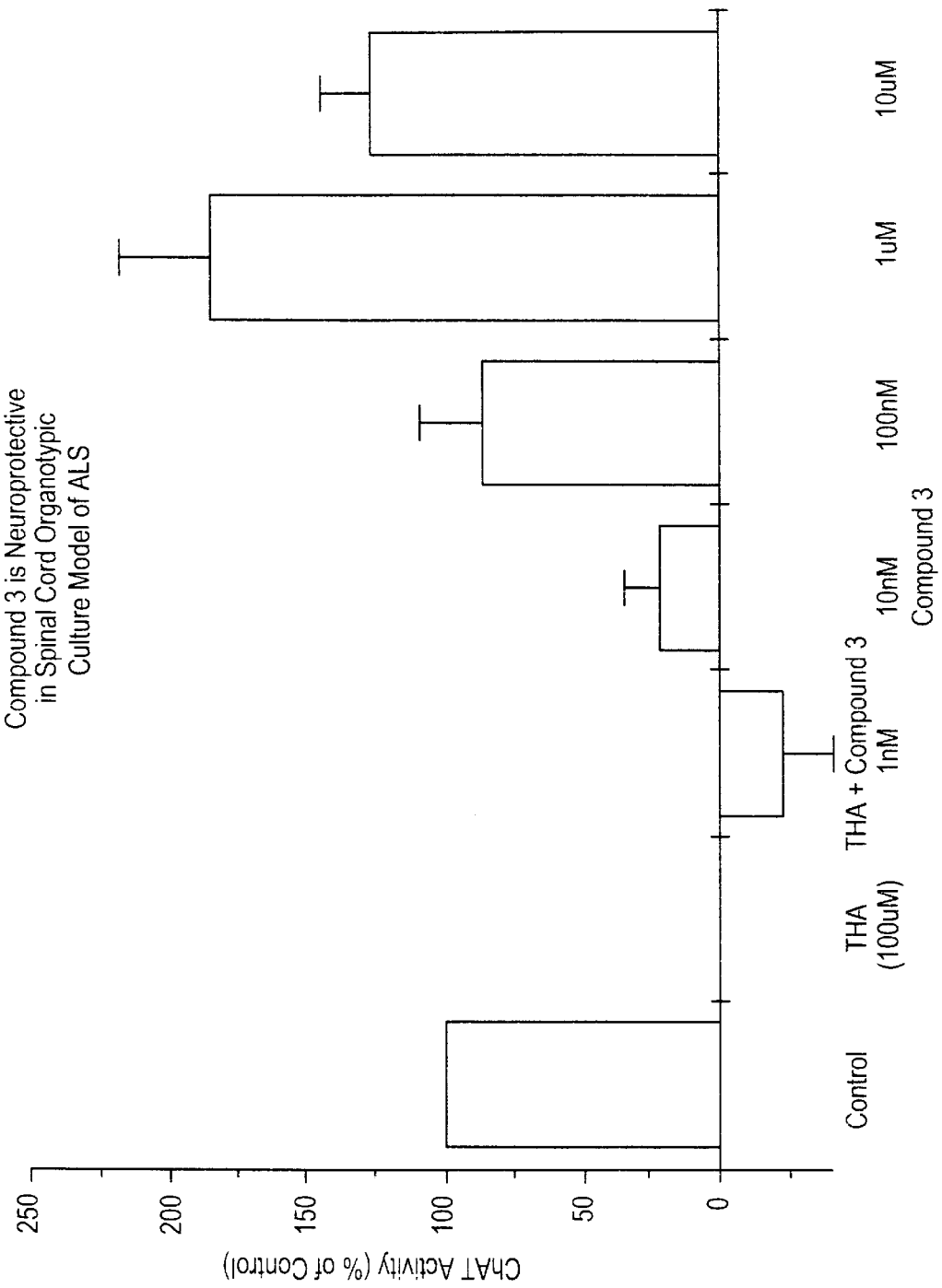

PHARMACEUTICAL COMPOSITIONS AND METHODS OF TREATING A GLUTAMATE ABNORMALITY AND EFFECTING A NEURONAL ACTIVITY IN AN ANIMAL USING NAALADASE INHIBITORS

This application is a continuation-in-part of U.S. patent application Ser. No. 08/718,703, filed Sep. 27, 1996, now U.S. Pat. No. 5,824,662; and a continuation-in-part of U.S. patent application Ser. No. 08/842,360, filed Apr. 24, 1997; and a continuation-in-part of U.S. patent application Ser. No. 08/863,624, filed May 27, 1997; and a continuation-in-part of and U.S. patent application Ser. No. 08/858,985, filed May 27, 1997, the entire contents of which applications are herein incorporated by reference.

BACKGROUND OF THE INVENTION

1. Field of the Invention

The present invention relates to a method of treating a glutamate abnormality and a method of effecting a neuronal activity in an animal using a NAALADase inhibitor, and a pharmaceutical composition comprising an effective amount of a NAALADase inhibitor for treating a glutamate abnormality and effecting a neuronal activity in an animal.

2. Description of the Prior Art

Glutamate Abnormalities

Glutamate has been implicated in various neurological diseases and conditions, including epilepsy, stroke, Alzheimer's disease, Parkinson's Disease, Amyotrophic Lateral Sclerosis (ALS), Huntington's Disease, schizophrenia, chronic pain, ischemia and neuronal loss following hypoxia, hypoglycemia, ischemia, trauma and nervous insult. Neurons release glutamate in great quantities when they are deprived of oxygen, as may occur during an ischemic brain insult such as a stroke or a heart attack. This excess release of glutamate in turn causes over-stimulation (excitotoxicity) of NMDA, AMPA, Kainate and MGR receptors. When glutamate binds to these receptors, ion channels in the cell membranes of the neurons open, permitting flows of ions across the cell membranes, e.g., $Ca^{2+}$ and $Na^+$ into the cells and $K^+$ out of the cells. These flows of ions, especially the influx of $Ca^{2+}$, cause over-stimulation of the neurons. The over-stimulated neurons secrete more glutamate, creating a domino-effect which ultimately results in cell death via the production of proteases, lipases and free radicals.

Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is currently no known effective treatment for glutate abnormalities.

NAALADase Inhibitors

NAAG and NAALADase have been implicated in several human and animal pathological conditions. For example, it has been demonstrated that intra-hippocampal injections of NAAG elicit prolonged seizure activity. More recently, it was reported that rats genetically prone to epileptic seizures have a persistent increase in their basal level of NAALADase activity. These observations support the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs. Additionally, NAALADase activity is significantly increased (two- to three-fold) in post-mortem spinal cord tissue from ALS patients and HCSMA dogs. As such, NAALADase inhibitors may be clinically useful in curbing the progression of ALS if increased metabolism of NAAG is responsible for the alterations of CSF levels of these acidic amino acids and peptides.

Abnormalities in NAAG levels and NAALADase activity have also been documented in post-mortem schizophrenic brain, specifically in the prefrontal and limbic brain regions.

The findings described above suggest that NAALADase inhibitors could be useful in treating glutamate abnormalities. In fact, the results of studies conducted by the inventors confirm that NAALADase inhibitors are effective in treating glutamate abnormalities, particularly stroke, Parkinson's Disease, Amyotrophic Lateral Sclerosis (ALS) and spinal cord injury.

While a few NAALADase inhibitors have been identified, they have only been used in non-clinical research. Examples of such inhibitors include general metallopeptidase inhibitors such as o-phenanthroline, metal chelators such as EGTA and EDTA, and peptide analogs such as quisqualic acid and β-NAAG. Accordingly, a need exists for new NAALADase inhibitors, as well as pharmaceutical compositions and methods using such new and known NAALADase inhibitors to treat glutamate abnormalities.

SUMMARY OF THE INVENTION

The present invention relates to a pharmaceutical composition comprising:

(i) an effective amount of a NAALADase inhibitor for treating a glutamate abnormality or effecting a neuronal activity in an animal; and (ii) a pharmaceutically acceptable carrier.

The present invention further relates to a method of treating a glutamate abnormality in an animal, comprising administering an effective amount of a NAALADase inhibitor to said animal.

The present invention also relates to a method of effecting a neuronal activity in an animal, comprising administering an effective amount of a NAALADase inhibitor to said animal.

BRIEF DESCRIPTION OF THE DRAWINGS

FIG. 5 is a bar graph plotting in vivo cortical injury volume against various doses of 2-(phosphonomethyl) pentanedioic acid with which rats were treated after sustaining middle cerebral artery occlusion.

FIG. 6 is a bar graph plotting in vivo total brain infarct volume of rats against various times at which the rats are treated with 2-(phosphonomethyl)pentanedioic acid after sustaining middle cerebral artery occlusion.

FIG. 7 is a bar graph plotting in vivo extracellular glutamate increases in the striatum of rats against various times at which the rats are treated with a vehicle or 2-(phosphonomethyl)pentanedioic acid after sustaining middle cerebral artery occlusion.

FIG. 8 is a bar graph plotting in vivo extracellular glutamate increases in the parietal cortex of rats against various times at which the rats are treated with a vehicle or 2-(phosphonomethyl)pentanedioic acid after sustaining middle cerebral artery occlusion.

FIG. 9 is a bar graph plotting in vivo extracellular glutamate increases in the frontal cortex of rats against various times at which the rats are treated with a vehicle or 2-(phosphonomethyl)pentanedioic acid after sustaining middle cerebral artery occlusion.

FIG. 11 is a bar graph plotting percent striatal TH innervation density against the treatment of mice with vehicle alone, vehicle following MPTP, or 2-(phosphonomethyl) pentanedioic acid following MPTP.

FIG. 12 is a bar graph plotting the neurological function code against the treatment of rats with dynorphin A alone or 2-(phosphonomethyl)pentanedioic acid with dynorphin A.

FIG. 13 is a bar graph plotting the ChAT activity of rat spinal cord organotypic cultures against the treatment of the cultures with 2-(phosphonomethyl)-pentanedioic acid alone, THA alone, or THA with 2-(phosphonomethyl)pentanedioic acid.

FIG. 14 is a bar graph plotting the ChAT activity of rat spinal cord organotypic cultures against various doses of 2-(phosphonomethyl)pentanedioic acid with which the cultures were treated in the presence of THA.

DETAILED DESCRIPTION OF THE INVENTION

Definitions

Figure 1:
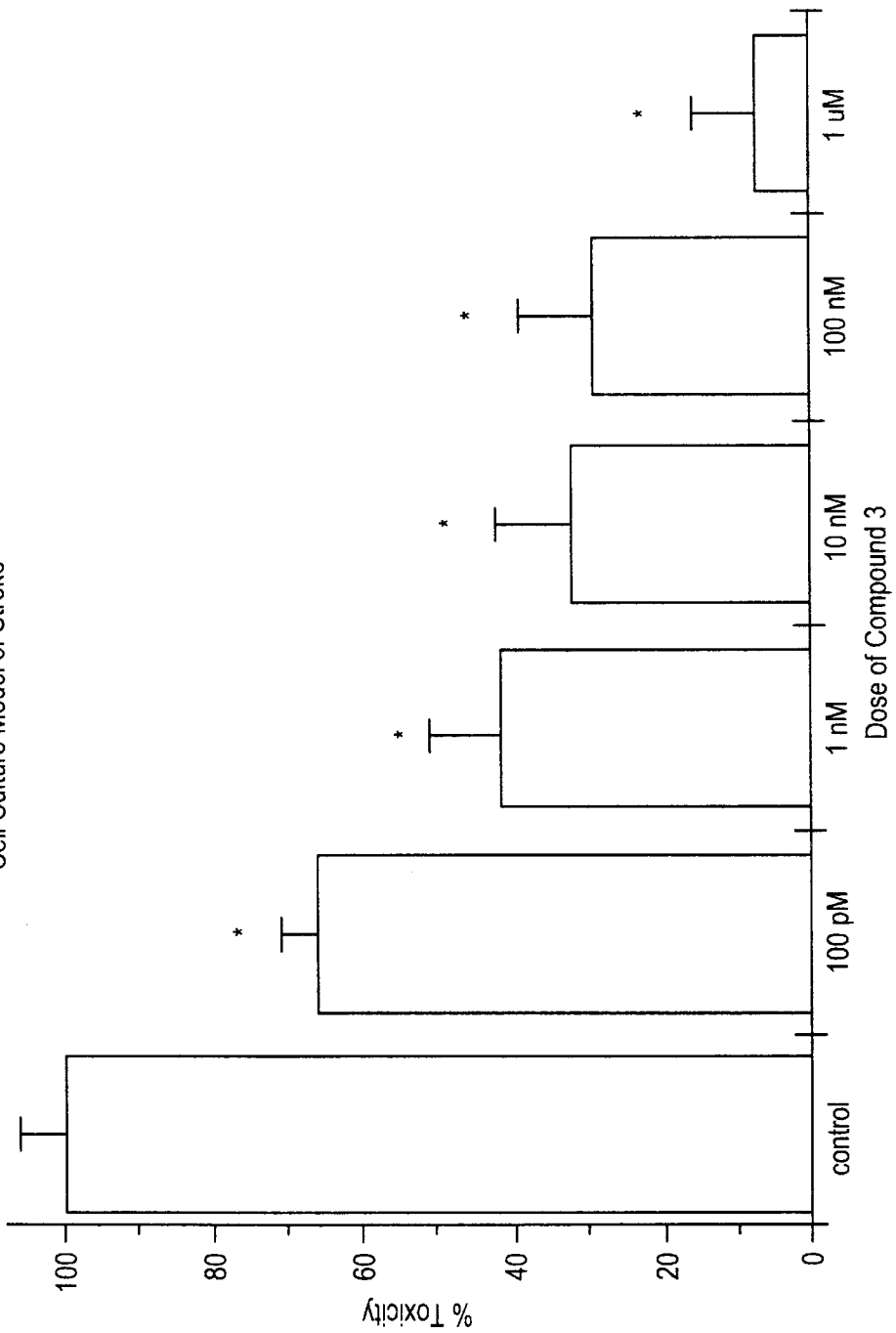
FIG. 1 is a bar graph plotting in vitro toxicity of ischemic insult (potassium cyanide and 2-deoxyglucose) against various doses of 2-(phosphonomethyl)pentanedioic acid with which cortical cell cultures were treated.

"Compound 3" refers to 2-(phosphonomethyl)pentanedioic acid (PMPA).

"Glutamate abnormality" refers to any disease, disorder or condition in which glutamate is implicated, including pathological conditions involving elevated levels of glutamate. Examples of glutamate abnormalities include epilepsy, stroke, Alzheimer's disease, Parkinson's Disease, Amyotrophic Lateral Sclerosis (ALS), Huntington's Disease, schizophrenia, chronic pain, ischemia and neuronal insult.

"Glutamate modulator" refers to any composition of matter which alone or in combination with another agent affects the level of glutamate in an animal.

"Inhibition", in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein $[E]$ is the concentration of the enzyme, $[I]$ is the concentration of the inhibitor, and $[EI]$ is the concentration of the enzyme-inhibitor complex formed by the reaction of the enzyme with the inhibitor. Unless otherwise specified, $K_i$ as used herein refers to the affinity between the inventive compounds and NAALADase. "$IC_{50}$" is a related term used to define the concentration or amount of a compound which is required to cause a 50% inhibition of the target enzyme.

"Ischemia" refers to localized tissue anemia due to obstruction of the inflow of arterial blood. Global ischemia occurs when blood flow to the entire brain ceases for a period of time, such as may result from cardiac arrest. Focal ischemia occurs when a portion of the brain is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate (NAA) and glutamate:

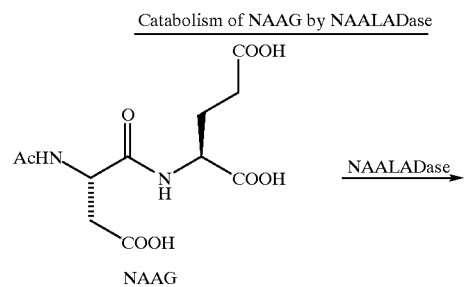

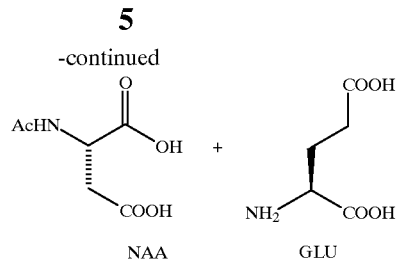

NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Nervous function" refers to the various functions of the nervous system, which among other things provide an awareness of the internal and external environments of the body, make possible voluntary and reflex activities between the various structural elements of the organism, and balance the organism's response to environmental changes.

"Nervous insult" refers to any damage to nervous tissue and any disability or death resulting therefrom. The cause of nervous insult may be metabolic, toxic, neurotoxic, iatrogenic, thermal or chemical, and includes without limitation ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination process, epilepsy, cognitive disorder, glutamate abnormality and secondary effects thereof. Currently, there is no known effective treatment for nervous tissue damage.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Neuroprotective" refers to the effect of reducing, arresting or ameliorating nervous insult, and protecting, resuscitating or reviving nervous tissue which has suffered nervous insult.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. The basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Treatment" refers to:

(i) preventing a disease, disorder or condition from occurring in an animal which may be predisposed to the disease, disorder and/or condition but has not yet been diagnosed as having it;

(ii) inhibiting the disease, disorder or condition, i.e., arresting its development; and (iii) relieving the disease, disorder or condition, i.e., causing regression of the disease, disorder and/or condition.

PHARMACEUTICAL COMPOSITIONS OF THE PRESENT INVENTION

The present invention relates to a pharmaceutical composition comprising:

(i) an effective amount of a NAALADase inhibitor for treating a glutamate abnormality or effecting a neuronal activity in an animal; and (ii) a pharmaceutically acceptable carrier.

The pharmaceutical composition may further comprise at least one additional therapeutic agent.

Since NAALADase is a metallopeptidase, useful NAALADase inhibitors for the pharmaceutical composition of the present invention include small molecule compounds with functional groups known to inhibit metallo-peptidases, such as hydroxyphosphinyl derivatives.

According to scientific literature, the glutamate moiety plays a more critical role than the aspartate moiety in the recognition of NAAG by NAALADase. As such, a preferred NAALADase inhibitor is a glutamate-derived hydroxyphosphinyl derivative, an acidic peptide analog or a mixture thereof.

A preferred acidic peptide analog is selected from the group consisting of Asp-Glu, Glu-Glu, Gly-Glu, gamma-Glu-Glu and Glu-Glu-Glu.

A preferred NAALADase inhibitor is a glutamate-derived hydroxyphosphinyl derivative of formula I:

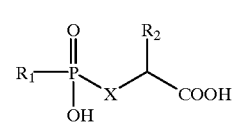

I or a pharmaceutically acceptable salt or hydrate thereof, wherein:

$R_1$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_2$–$C_9$ alkoxy, $C_2$–$C_9$ alkenyloxy, phenoxy, benzyloxy, amino, Ar or mixtures thereof;

X is $CR_3R_4$, O or $NR_1$;

$R_3$ and $R_4$ are independently selected from the group consisting of hydrogen, $C_1$–$C_6$ straight or branched chain alkyl, $C_2$–$C_6$ straight or branched chain alkenyl, $C_3$–$C_8$ cycloalkyl, $C_5$–$C_7$ cycloalkenyl, Ar, halo and mixtures thereof;

$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, Ar or mixtures thereof;

Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino or mixtures thereof.

Preferably, X is $CH_2$.

More preferably, $R_2$ is substituted with carboxy.

Even more preferably, $R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof; and $R_2$ is $C_1$–$C_2$ alkyl.

Most preferably, the glutamate-derived hydroxyphosphinyl derivative is selected from the group consisting of:
2-(phosphonomethyl)pentanedioic acid;
2-(phosphonomethyl)succinic acid;
2-[[(2-carboxyethyl)hydroxyphosphinyl]methyl] pentanedioic acid;
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[(cyclohexyl)methylhydroxyphosphinyl]methyl] pentanedioic acid;
2-[[phenylhydroxyphosphinyl]methyl]pentanedioic acid;
2-[(benzylhydroxyphosphinyl)methyl]pentanedioic acid;
2-[[(phenylmethyl)hydroxyphosphinyl]methyl]pentanedioic acid;
2-[[(phenylethyl)hydroxyphosphinyl]methyl]pentanedioic acid;
2-[[(phenylpropyl)hydroxyphosphinyl]methyl]pentanedioic acid;
2-[[(phenylbutyl)hydroxyphosphinyl]methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(methoxybenzyl)hydroxyphosphinyl]methyl] pentanedioic acid;
2-[[(2,3,4-trimethoxyphenyl)hydroxyphosphinyl]methyl] pentanedioic acid;
2-[[(phenylprop-2-enyl) hydroxyphosphinyl]methyl] pentanedioic acid;
2-[[(2-fluorobenzyl)hydroxyphosphinyl]methyl] pentanedioic acid;
2-[[((hydroxy)phenylmethyl)hydroxyphosphinyl]methyl] pentanedioic acid;
2-[[(3-methylbenzyl)hydroxyphosphinyl]methyl] pentanedioic acid;
2-[[(4-fluorophenyl)hydroxyphosphinyl]methyl] pentanedioic acid;
2-[[(3-trifluoromethylbenzyl)hydroxyphosphinyl]methyl]- pentanedioic acid; and pharmaceutically acceptable salts and hydrates thereof.

In other embodiments, $R_2$ is $C_3$–$C_9$ alkyl; $R_1$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl or $C_1$–$C_4$ straight or branched chain alkyl substituted with 2-indolyl, 3-indolyl, 4-indolyl, 2-furyl, 3-furyl, tetrahydrofuranyl, 2-thienyl, 3-thienyl, 2-pyridyl, 3-pyridyl or 4-pyridyl; or $R_1$ is 1-naphthyl, 2-naphthyl, or $C_1$–$C_4$ straight or branched chain alkyl substituted with 1-naphthyl or 2-naphthyl.

Preferred compounds of these embodiments include:
2-[(methylhydroxyphosphinyl)methyl]hexanedioic acid;
2-[(benzylhydroxyphosphinyl)methyl]hexanedioic acid;
2-[(methylhydroxyphosphinyl)methyl]heptanedioic acid;
2-[(benzylhydroxyphosphinyl)methyl]heptanedioic acid;
2-[(methylhydroxyphosphinyl)methyl]octanedioic acid;
2-[(benzylhydroxyphosphinyl)methyl]hoctanedioic acid;
2-[(methylhydroxyphosphinyl)methyl]nonanedioic acid;
2-[(benzylhydroxyphosphinyl)methyl]nonanedioic acid;
2-[(methylhydroxyphosphinyl)methyl]decanedioic acid;
2-[(benzylhydroxyphosphinyl)methyl]decanedioic acid;
2-[[(2-pyridyl)methylhydroxyphosphinyl]methyl] pentanedioic acid;
2-[[(3-pyridyl)methylhydroxyphosphinyl]methyl] pentanedioic acid;
2-[[(4-pyridyl)methylhydroxyphosphinyl]methyl] pentanedioic acid;
2-[[(3-pyridyl)ethylhydroxyphosphinyl]methyl] pentanedioic acid;
2-[[(3-pyridyl)propylhydroxyphosphinyl]methyl] pentanedioic acid;
2-[[(tetrahydrofuranyl)methylhydroxyphosphinyl]methyl] pentanedioic acid;
2-[[(tetrahydrofuranyl)ethylhydroxyphosphinyl]methyl] pentanedioic acid;
2-[[(tetrahydrofuranyl)propylhydroxyphosphinyl]methyl] pentanedioic acid;
2-[[(2-tetrahydropyranyl)hydroxyphosphinyl]methyl] pentanedioic acid;
2-[[(3-tetrahydropyranyl)hydroxyphosphinyl]methyl] pentanedioic acid;
2-[[(4-tetrahydropyranyl)hydroxyphosphinyl]methyl] pentanedioic acid;
2-[[(2-indolyl)methylhydroxyphosphinyl]methyl] pentanedioic acid;
2-[[(3-indolyl)methylhydroxyphosphinyl]methyl] pentanedioic acid;
2-[[(4-indolyl)methylhydroxyphosphinyl]methyl] pentanedioic acid;
2-[[(3-indolyl)ethylhydroxyphosphinyl]methyl] pentanedioic acid;
2-[[(3-indolyl)propylhydroxyphosphinyl]methyl] pentanedioic acid;
2-[[(2-thienyl)methylhydroxyphosphinyl]methyl] pentanedioic acid;

2-[[(3-thienyl)methylhydroxyphosphinyl]methyl] pentanedioic acid;
2-[[(4-thienyl)methylhydroxyphosphinyl]methyl] pentanedioic acid;
2-[[(3-thienyl)ethylhydroxyphosphinyl]methyl] pentanedioic acid;
2-[[(3-thienyl)propylhydroxyphosphinyl]methyl] pentanedioic acid;
2-[[(2-pyridyl)hydroxyphosphinyl]methyl]pentanedioic acid;
2-[[(3-pyridyl)hydroxyphosphinyl]methyl]pentanedioic acid;
2-[[(4-pyridyl)hydroxyphosphinyl]methyl]pentanedioic acid;
2-[[(tetrahydrofuranyl)hydroxyphosphinyl]methyl] pentanedioic acid;
2-[[(2-indolyl)hydroxyphosphinyl]methyl]pentanedioic acid;
2-[[(3-indolyl)hydroxyphosphinyl]methyl]pentanedioic acid;
2-[[(4-indolyl)hydroxyphosphinyl]methyl]pentanedioic acid;
2-[[(2-thienyl)hydroxyphosphinyl]methyl]pentanedioic acid;
2-[[(3-thienyl)hydroxyphosphinyl]methyl]pentanedioic acid;
2-[[(4-thienyl)hydroxyphosphinyl]methyl]pentanedioic acid;
2-[[(1-naphthyl)hydroxyphosphinyl]methyl]pentanedioic acid;
2-[[(2-naphthyl)hydroxyphosphinyl]methyl]pentanedioic acid;
2-[[(1-naphthyl)methylhydroxyphosphinyl]methyl] pentanedioic acid;
2-[[(2-naphthyl)methylhydroxyphosphinyl]methyl] pentanedioic acid;
2-[[(1-naphthyl)ethylhydroxyphosphinyl]methyl] pentanedioic acid;
2-[[(2-naphthyl)ethylhydroxyphosphinyl]methyl] pentanedioic acid;
2-[[(1-naphthyl)propylhydroxyphosphinyl]methyl] pentanedioic acid;
2-[[(2-naphthyl)propylhydroxyphosphinyl]methyl] pentanedioic acid;
2-[[(1-naphthyl)butylhydroxyphosphinyl]methyl] pentanedioic acid;
2-[[(2-naphthyl)butylhydroxyphosphinyl]methyl] pentanedioic acid; and
pharmaceutically acceptable salts and hydrates thereof.

In another preferred embodiment, X is $CH_2$ and $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

More preferably, $R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof.

Most preferably, the glutamate-derived hydroxyphosphinyl derivative is selected from the group consisting of:

3-(methylhydroxyphosphinyl)-2-phenylpropanoic acid;
3-(ethylhydroxyphosphinyl)-2-phenylpropanoic acid;
3-(propylhydroxyphosphinyl)-2-phenylpropanoic acid;
3-(butylhydroxyphosphinyl)-2-phenylpropanoic acid;
3-(cyclohexylhydroxyphosphinyl)-2-phenylpropanoic acid;
3-((cyclohexyl)methylhydroxyphosphinyl)-2-phenylpropanoic acid;
3-(phenylhydroxyphosphinyl)-2-phenylpropanoic acid;
3-(benzylhydroxyphosphinyl)-2-phenylpropanoic acid;
3-(phenylethylhydroxyphosphinyl)-2-phenylpropanoic acid;
3-(phenylpropylhydroxyphosphinyl)-2-phenylpropanoic acid;
3-(phenylbutylhydroxyphosphinyl)-2-phenylpropanoicacid;
3-((2,3,4-trimethoxyphenyl)-3-hydroxyphosphinyl)-2-phenylpropanoic acid;
3-(phenylprop-2-enylhydroxyphosphinyl)-2-phenylpropanoic acid;
3-(benzylhydroxyphosphinyl)-2-ethypropanoic acid;
3-(benzylhydroxyphosphinyl)-2-propylpropanoic acid;
3-(benzylhydroxyphosphinyl)-2-butylpropanoic acid;
3-(benzylhydroxyphosphinyl)-2-cyclohexylpropanoic acid;
3-(benzylhydroxyphosphinyl)-2-(cyclohexyl) methylpropanoic acid;
3-(benzylhydroxyphosphinyl)-2-phenylpropanoic acid;
3-(benzylhydroxyphosphinyl)-2-benzylpropanoic acid;
3-(benzylhydroxyphosphinyl)-2-phenylethylpropanoicacid;
3-(benzylhydroxyphosphinyl)-2-phenylpropylpropanoic acid;
3-(benzylhydroxyphosphinyl)-2-phenylbutylpropanoicacid;
3-(benzylhydroxyphosphinyl)-2-(2,3,4-trimethoxyphenyl)-propanoic acid;
3-(benzylhydroxyphosphinyl)-2-phenylprop-2-enylpropanoic acid; and
pharmaceutically acceptable salts and hydrates thereof.

In other embodiments, at least one of $R_1$ and $R_2$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, or $C_1$–$C_4$ straight or branched chain alkyl substituted with 2-indolyl 3-indolyl, 4-indolyl, 2-furyl, 3-furyl, tetrahydrofuranyl, 2-thienyl, 3-thienyl, 2-pyridyl, 3-pyridyl or 4-pyridyl; or $R_1$ is 1-naphthyl, 2-naphthyl, or $C_1$–$C_4$ straight or branched chain alkyl substituted with 1-naphthyl or 2-naphthyl.

Preferred compounds of these embodiments include:
3-[(2-pyridyl)methylhydroxyphosphinyl]-2-phenylpropanoic acid;
3-[(3-pyridyl)methylhydroxyphosphinyl]-2-phenylpropanoic acid;
3-[(4-pyridyl)methylhydroxyphosphinyl]-2-phenylpropanoic acid;
3-[(3-pyridyl)ethylhydroxyphosphinyl]-2-phenylpropanoic acid;
3-[(3-pyridyl)propylhydroxyphosphinyl]-2-phenylpropanoic acid;
3-[(tetrahydrofuranyl)methylhydroxyphosphinyl]-2-phenylpropanoic acid;
3-[(tetrahydrofuranyl)ethylhydroxyphosphinyl]-2-phenylpropanoic acid;
3-[(tetrahydrofuranyl)propylhydroxyphosphinyl]-2-phenylpropanoic acid;
3-[(2-indolyl)methylhydroxyphosphinyl]-2-phenylpropanoic acid;
3-[(3-indolyl)methylhydroxyphosphinyl]-2-phenylpropanoic acid;
3-[(4-indolyl)methylhydroxyphosphinyl]-2-phenylpropanoic acid;

3-[(3-indolyl)ethylhydroxyphosphinyl]-2-phenylpropanoic acid;
3-[(3-indolyl)propylhydroxyphosphinyl]-2-phenylpropanoic acid;
3-[(2-thienyl)methylhydroxyphosphinyl]-2-phenylpropanoic acid;
3-[(3-thienyl)methylhydroxyphosphinyl]-2-phenylpropanoic acid;
3-[(4-thienyl)methylhydroxyphosphinyl]-2-phenylpropanoic acid;
3-[(3-thienyl)ethylhydroxyphosphinyl]-2-phenylpropanoic acid;
3-[(3-thienyl)propylhydroxyphosphinyl]-2-phenylpropanoic acid;
3-(benzylhydroxyphosphinyl)-2-(2-pyridyl)methylpropanoic acid;
3-(benzylhydroxyphosphinyl)-2-(3-pyridyl)methylpropanoic acid;
3-(benzylhydroxyphosphinyl)-2-(4-pyridyl)methylpropanoic acid;
3-(benzylhydroxyphosphinyl)-2-(3-pyridyl)ethylpropanoic acid;
3-(benzylhydroxyphosphinyl)-2-(3-pyridyl)propylpropanoic acid;
3-(benzylhydroxyphosphinyl)-2-(tetrahydrofuranyl)methylpropanoic acid;
3-(benzylhydroxyphosphinyl)-2-(tetrahydrofuranyl)ethylpropanoic acid;
3-(benzylhydroxyphosphinyl)-2-(tetrahydrofuranyl)propylpropanoic acid;
3-(benzylhydroxyphosphinyl)-2-(2-indolyl)methylpropanoic acid;
3-(benzylhydroxyphosphinyl)-2-(3-indolyl)methylpropanoic acid;
3-(benzylhydroxyphosphinyl)-2-(4-indolyl)methylpropanoic acid;
3-(benzylhydroxyphosphinyl)-2-(3-indolyl)ethylpropanoic acid;
3-(benzylhydroxyphosphinyl)-2-(3-indolyl)propylpropanoic acid;
3-(benzylhydroxyphosphinyl)-2-(2-thienyl)methylpropanoic acid;
3-(benzylhydroxyphosphinyl)-2-(3-thienyl)methylpropanoic acid;
3-(benzylhydroxyphosphinyl)-2-(4-thienyl)methylpropanoic acid;
3-(benzylhydroxyphosphinyl)-2-(3-thienyl)ethylpropanoic acid;
3-(benzylhydroxyphosphinyl)-2-(3-thienyl)propylpropanoic acid;
3-((1-naphthyl)hydroxyphosphinyl)-2-phenylpropanoic acid;
3-((2-naphthyl)hydroxyphosphinyl)-2-phenylpropanoic acid;
3-((1-naphthyl)methylhydroxyphosphinyl)-2-phenylpropanoic acid;
3-((2-naphthyl)methylhydroxyphosphinyl)-2-phenylpropanoic acid;
3-((1-naphthyl)ethylhydroxyphosphinyl)-2-phenylpropanoic acid;
3-((2-naphthyl)ethylhydroxyphosphinyl)-2-phenylpropanoic acid;
3-((1-naphthyl)propylhydroxyphosphinyl)-2-phenylpropanoic acid;
3-((2-naphthyl)propylhydroxyphosphinyl)-2-phenylpropanoic acid;
3-((1-naphthyl)butylhydroxyphosphinyl)-2-phenylpropanoic acid;
3-((2-naphthyl)butylhydroxyphosphinyl)-2-phenylpropanoic acid; and pharmaceutically acceptable salts and hydrates thereof.

When X is O, $R_2$ is preferably substituted with carboxy. Exemplary compounds of this embodiment include:

2-[[methylhydroxyphosphinyl]oxy]pentanedioic acid;
2-[[ethylhydroxyphosphinyl]oxy]pentanedioic acid;
2-[[propylhydroxyphosphinyl]oxy]pentanedioic acid;
2-[[butylhydroxyphosphinyl]oxy]pentanedioic acid;
2-[[cyclohexylhydroxyphosphinyl]oxy]pentanedioic acid;
2-[[(cyclohexyl)methylhydroxyphosphinyl]oxy]pentanedioic acid;
2-[[phenylhydroxyphosphinyl]oxy]pentanedioic acid;
2-[[benzylhydroxyphosphinyl]oxy]pentanedioic acid;
2-[[phenylethylhydroxyphosphinyl]oxy]pentanedioic acid;
2-[[phenylpropylhydroxyphosphinyl]oxy]pentanedioic acid;
2-[[phenylbutylhydroxyphosphinyl]oxy]pentanedioic acid;
2-[[(4-methylbenzyl)hydroxyphosphinyl]oxy]pentanedioic acid;
2-[[(4-fluorobenzyl)hydroxyphosphinyl]oxy]pentanedioic acid;
2-[[(2-fluorobenzyl)hydroxyphosphinyl]oxy]pentanedioic acid;
2-[[(pentafluorobenzyl)hydroxyphosphinyl]oxy]pentanedioic acid;
2-[[(methoxybenzyl)hydroxyphosphinyl]oxy]pentanedioic acid;
2-[[(2,3,4-trimethoxyphenyl)hydroxyphosphinyl]oxy]pentanedioic acid;
2-[[(1-naphthyl)hydroxyphosphinyl]oxy]pentanedioic acid;
2-[[(2-naphthyl)hydroxyphosphinyl]oxy]pentanedioic acid;
2-[[(1-naphthyl)methylhydroxyphosphinyl]oxy]pentanedioic acid;
2-[[(2-naphthyl)methylhydroxyphosphinyl]oxy]pentanedioic acid;
2-[[(1-naphthyl)ethylhydroxyphosphinyl]oxy]pentanedioic acid;
2-[[(2-naphthyl)ethylhydroxyphosphinyl]oxy]pentanedioic acid;
2-[[(1-naphthyl)propylhydroxyphosphinyl]oxy]pentanedioic acid;
2-[[(2-naphthyl)propylhydroxyphosphinyl]oxy]pentanedioic acid;
2-[[(1-naphthyl)butylhydroxyphosphinyl]oxy]pentanedioic acid;
2-[[(2-naphthyl)butylhydroxyphosphinyl]oxy]pentanedioic acid;
2-[[(phenylprop-2-enyl)hydroxyphosphinyl]oxy]pentanedioic acid;
2-[[benzylhydroxyphosphinyl]oxy]pentanedioic acid;
2-[[((hydroxy)phenylmethyl)hydroxyphosphinyl]oxy]pentanedioic acid;
2-[[(3-methylbenzyl)hydroxyphosphinyl]oxy]pentanedioic acid;
2-[[(4-fluorophenyl)hydroxyphosphinyl]oxy]pentanedioic acid;
2-[[(2-fluorobenzyl)hydroxyphosphinyl]oxy]pentanedioic acid;
2-(phosphono)oxy]pentanedioic acid;
2-[[(3-trifluoromethylbenzyl)hydroxyphosphinyl]oxy]pentanedioic acid;
2-[[methylhydroxyphosphinyl]oxy]-2-phenylethanoic acid;
2-[[ethylhydroxyphosphinyl]oxy]-2-phenylethanoic acid;
2-[[propylhydroxyphosphinyl]oxy]-2-phenylethanoic acid;
2-[[butylhydroxyphosphinyl]oxy]-2-phenylethanoic acid;
2-[[cyclohexylhydroxyphosphinyl]oxy]-2-phenylethanoic acid;

2-[[(cyclohexyl)methylhydroxyphosphinyl]oxy]-2-phenylethanoic acid;
2-[[phenylhydroxyphosphinyl]oxy]-2-phenylethanoic acid;
2-[[benzylhydroxyphosphinyl]oxy]-2-phenylethanoic acid;
2-[[phenylethylhydroxyphosphinyl]oxy]-2-phenylethanoic acid;
2-[[phenylpropylhydroxyphosphinyl]oxy]-2-phenylethanoic acid;
2-[[phenylbutylhydroxyphosphinyl]oxy]-2-phenylethanoic acid;
2-[[(2,3,4-trimethoxyphenyl)-3-hydroxyphosphinyl]oxy]-2-phenylethanoic acid;
2-[[(1-naphthyl)hydroxyphosphinyl]oxy]-2-phenylethanoic acid;
2-[[(2-naphthyl)hydroxyphosphinyl]oxy]-2-phenylethanoic acid;
2-[[(1-naphthyl)methylhydroxyphosphinyl]oxy]-2-phenylethanoic acid;
2-[[(2-naphthyl)methylhydroxyphosphinyl]oxy]-2-phenylethanoic acid;
2-[[(1-naphthyl)ethylhydroxyphosphinyl]oxy]-2-phenylethanoic acid;
2-[[(2-naphthyl)ethylhydroxyphosphinyl]oxy]-2-phenylethanoic acid;
2-[[(1-naphthyl)propylhydroxyphosphinyl]oxy]-2-phenylethanoic acid;
2-[[(2-naphthyl)propylhydroxyphosphinyl]oxy]-2-phenylethanoic acid;
2-[[(1-naphthyl)butylhydroxyphosphinyl]oxy]-2-phenylethanoic acid;
2-[[(2-naphthyl)butylhydroxyphosphinyl]oxy]-2-phenylethanoic acid;
2-[[phenylprop-2-enylhydroxyphosphinyl]oxy]-2-phenylethanoic acid;
2-[(methylhydroxyphosphinyl)oxy]hexanedioic acid;
2-[(benzylhydroxyphosphinyl)oxy]hexanedioic acid;
2-[(methylhydroxyphosphinyl)oxy]heptanedioic acid;
2-[(benzylhydroxyphosphinyl)oxy]heptanedioic acid;
2-[(methylhydroxyphosphinyl)oxy]octanedioic acid;
2-[(benzylhydroxyphosphinyl)oxy]octanedioic acid;
2-[(methylhydroxyphosphinyl)oxy]nonanedioic acid;
2-[(benzylhydroxyphosphinyl)oxy]nonanedioic acid;
2-[(methylhydroxyphosphinyl)oxy]decanedioic acid;
2-[(benzylhydroxyphosphinyl)oxy]decanedioic acid;
2-[[benzylhydroxyphosphinyl]oxy]-2-methylethanoic acid;
2-[[benzylhydroxyphosphinyl]oxy]-2-ethylethanoic acid;
2-[[benzylhydroxyphosphinyl]oxy]-2-propylethanoic acid;
2-[[benzylhydroxyphosphinyl]oxy]-2-butylethanoic acid;
2-[[benzylhydroxyphosphinyl]oxy]-2-cyclohexylethanoic acid;
2-[[benzylhydroxyphosphinyl]oxy]-2-(cyclohexyl)methylethanoic acid;
2-[[benzylhydroxyphosphinyl]oxy]-2-phenylethanoic acid;
2-[[benzylhydroxyphosphinyl]oxy]-2-benzylethanoic acid;
2-[[benzylhydroxyphosphinyl]oxy]-2-phenylethylethanoic acid;
2-[[benzylhydroxyphosphinyl]oxy]-2-phenylpropylethanoic acid;
2-[[benzylhydroxyphosphinyl]oxy]-2-phenylbutylethanoic acid;
2-[[benzylhydroxyphosphinyl]oxy]-2-(2,3,4-trimethoxyphenyl)ethanoic acid;
2-[[benzylhydroxyphosphinyl]oxy]-2-(1-naphthyl)ethanoic acid;
2-[[benzylhydroxyphosphinyl]oxy]-2-(2-naphthyl)ethanoic acid;
2-[[benzylhydroxyphosphinyl]oxy]-2-(1-naphthyl)methylethanoic acid;
2-[[benzylhydroxyphosphinyl]oxy]-2-(2-naphthyl)methylethanoic acid;
2-[[benzylhydroxyphosphinyl]oxy]-2-(1-naphthyl)ethylethanoic acid;
2-[[benzylhydroxyphosphinyl]oxy]-2-(2-naphthyl)ethylethanoic acid;
2-[[benzylhydroxyphosphinyl]oxy]-2-(1-naphthyl)propylethanoic acid;
2-[[benzylhydroxyphosphinyl]oxy]-2-(2-naphthyl)propylethanoic acid;
2-[[benzylhydroxyphosphinyl]oxy]-2-(1-naphthyl)butylethanoic acid;
2-[[benzylhydroxyphosphinyl]oxy]-2-(2-naphthyl)butylethanoic acid;
2-[[benzylhydroxyphosphinyl]oxy]-2-phenylprop-2-enylethanoic acid;
2-[[(2-pyridyl)methylhydroxyphosphinyl]oxy]pentanedioic acid;
2-[[(3-pyridyl)methylhydroxyphosphinyl]oxy]pentanedioic acid;
2-[[(4-pyridyl)methylhydroxyphosphinyl]oxy]pentanedioic acid;
2-[[(3-pyridyl)ethylhydroxyphosphinyl]oxy]pentanedioic acid;
2-[[(3-pyridyl)propylhydroxyphosphinyl]oxy]pentanedioic acid;
2-[[(tetrahydrofuranyl)methylhydroxyphosphinyl]oxy]pentanedioic acid;
2-[[(tetrahydrofuranyl)ethylhydroxyphosphinyl]oxy]pentanedioic acid;
2-[[(tetrahydrofuranyl)propylhydroxyphosphinyl]oxy]pentanedioic acid;
2-[[(2-indolyl)methylhydroxyphosphinyl]oxy]pentanedioic acid;
2-[[(3-indolyl)methylhydroxyphosphinyl]oxy]pentanedioic acid;
2-[[(3-indolyl)methylhydroxyphosphinyl]oxy]pentanedioic acid;
2-[[(3-indolyl)ethylhydroxyphosphinyl]oxy]pentanedioic acid;
2-[[(2-indolyl)prethylhydroxyphosphinyl]oxy]pentanedioic acid;
2-[[(3-thienyl)methylhydroxyphosphinyl]oxy]pentanedioic acid;
2-[[(3-thienyl)methylhydroxyphosphinyl]oxy]pentanedioic acid;
2-[[(4-thienyl)methylhydroxyphosphinyl]oxy]pentanedioic acid;
2-[[(3-thienyl)ethylhydroxyphosphinyl]oxy]pentanedioic acid;
2-[[(3-thienyl)propylhydroxyphosphinyl]oxy]pentanedioic acid; and pharmaceutically acceptable salts and hydrates thereof.

In another preferred embodiment, $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

Exemplary compounds of this embodiment include:
2-[[(2-pyridyl)methylhydroxyphosphinyl]oxy]-2-phenylethanoic acid;
2-[[(3-pyridyl)methylhydroxyphosphinyl]oxy]-2-phenylethanoic acid;
2-[[(4-pyridyl)methylhydroxyphosphinyl]oxy]-2-phenylethanoic acid;

2-[[(3-pyridyl)ethylhydroxyphosphinyl]oxy]-2-phenylethanoic acid;
2-[[(3-pyridyl)propylhydroxyphosphinyl]oxy]-2-phenylethanoic acid;
2-[[(tetrahydrofuranyl)methylhydroxyphosphinyl]oxy]-2-phenylethanoic acid;
2-[[(tetrahydrofuranyl)ethylhydroxyphosphinyl]oxy]-2-phenylethanoic acid;
2-[[(tetrahydrofuranyl)propylhydroxyphosphinyl]oxy]-2-phenylethanoic acid;
2-[[(2-indolyl)methylhydroxyphosphinyl]oxy]-2-phenylethanoic acid;
2-[[(3-indolyl)methylhydroxyphosphinyl]oxy]-2-phenylethanoic acid;
2-[[(4-indolyl)methylhydroxyphosphinyl]oxy]-2-phenylethanoic acid;
2-[[(3-indolyl)ethylhydroxyphosphinyl]oxy]-2-phenylethanoic acid;
2-[[(3-indolyl)propylhydroxyphosphinyl]oxy]-2-phenylethanoic acid;
2-[[(2-thienyl)methylhydroxyphosphinyl]oxy]-2-phenylethanoic acid;
2-[[(3-thienyl)methylhydroxyphosphinyl]oxy]-2-phenylethanoic acid;
2-[[(4-thienyl)methylhydroxyphosphinyl]oxy]-2-phenylethanoic acid;
2-[[(3-thienyl)ethylhydroxyphosphinyl]oxy]-2-phenylethanoic acid;
2-[[(3-thienyl)propylhydroxyphosphinyl]oxy]-2-phenylethanoic acid;
2-[[benzylhydroxyphosphinyl]oxy]-2-(2-pyridyl)methylethanoic acid;
2-[[benzylhydroxyphosphinyl]oxy]-2-(3-pyridyl)methylethanoic acid;
2-[[benzylhydroxyphosphinyl]oxy]-2-(4-pyridyl)methylethanoic acid;
2-[[benzylhydroxyphosphinyl]oxy]-2-(3-pyridyl)ethylethanoic acid;
2-[[benzylhydroxyphosphinyl]oxy]-2-(3-pyridyl)propylethanoic acid;
2-[[benzylhydroxyphosphinyl]oxy]-2-(tetrahydrofuranyl)methylethanoic acid;
2-[[benzylhydroxyphosphinyl]oxy]-2-(tetrahydrofuranyl)ethylethanoic acid;
2-[[benzylhydroxyphosphinyl]oxy]-2-(tetrahydrofuranyl)propylethanoic acid;
2-[[benzylhydroxyphosphinyl]oxy]-2-(2-indolyl)methylethanoic acid;
2-[[benzylhydroxyphosphinyl]oxy]-2-(3-indolyl)methylethanoic acid;
2-[[benzylhydroxyphosphinyl]oxy]-2-(4-indolyl)methylethanoic acid;
2-[[benzylhydroxyphosphinyl]oxy]-2-(3-indolyl)ethylethanoic acid;
2-[[benzylhydroxyphosphinyl]oxy]-2-(3-indolyl)propylethanoic acid;
2-[[benzylhydroxyphosphinyl]oxy]-2-(2-thienyl)methylethanoic acid;
2-[[benzylhydroxyphosphinyl]oxy]-2-(3-thienyl)methylethanoic acid;
2-[[benzylhydroxyphosphinyl]oxy]-2-(4-thienyl)methylethanoic acid;
2-[[benzylhydroxyphosphinyl]oxy]-2-(3-thienyl)ethylethanoic acid;
2-[[benzylhydroxyphosphinyl]oxy]-2-(3-thienyl)propylethanoic acid; and
pharmaceutically acceptable salts and hydrates thereof.

When X is $NR_1$, $R_2$ is preferably substituted with carboxy. Exemplary compounds of this embodiment include:
2-[[methylhydroxyphosphinyl]amino]pentanedioic acid;
2-[[ethylhydroxyphosphinyl]amino]pentanedioic acid;
2-[[propylhydroxyphosphinyl]amino]pentanedioic acid;
2-[[butylhydroxyphosphinyl]amino]pentanedioic acid;
2-[[cyclohexylhydroxyphosphinyl]amino]pentanedioic acid;
2-[[(cyclohexyl)methylhydroxyphosphinyl]amino]pentanedioic acid;
2-[[phenylhydroxyphosphinyl]amino]pentanedioic acid;
2-[[benzylhydroxyphosphinyl]amino]pentanedioic acid;
2-[[phenylethylhydroxyphosphinyl]amino]pentanedioic acid;
2-[[phenylpropylhydroxyphosphinyl]amino]pentanedioic acid;
2-[[phenylbutylhydroxyphosphinyl]amino]pentanedioic acid;
2-[[(4-methylbenzyl)hydroxyphosphinyl]amino]pentanedioic acid;
2-[[(4-fluorobenzyl)hydroxyphosphinyl]amino]pentanedioic acid;
2-[[(2-fluorobenzyl)hydroxyphosphinyl]amino]pentanedioic acid;
2-[[(pentafluorobenzyl)hydroxyphosphinyl]amino]pentanedioic acid;
2-[[(methoxybenzyl)hydroxyphosphinyl]amino]pentanedioic acid;
2-[[(2,3,4-trimethoxyphenyl)hydroxyphosphinyl]amino]pentanedioic acid;
2-[[(1-naphthyl)hydroxyphosphinyl]amino]pentanedioic acid;
2-[[(2-naphthyl)hydroxyphosphinyl]amino]pentanedioic acid;
2-[[(1-naphthyl)methylhydroxyphosphinyl]amino]pentanedioic acid;
2-[[(2-naphthyl)methylhydroxyphosphinyl]amino]pentanedioic acid;
2-[[(1-naphthyl)ethylhydroxyphosphinyl]amino]pentanedioic acid;
2-[[(2-naphthyl)ethylhydroxyphosphinyl]amino]pentanedioic acid;
2-[[(1-naphthyl)propylhydroxyphosphinyl]amino]pentanedioic acid;
2-[[(2-naphthyl)propylhydroxyphosphinyl]amino]pentanedioic acid;
2-[[(1-naphthyl)butylhydroxyphosphinyl]amino]pentanedioic acid;
2-[[(2-naphthyl)butylhydroxyphosphinyl]amino]pentanedioic acid;
2-[[(phenylprop-2-enyl)hydroxyphosphinyl]amino]pentanedioic acid;
2-[[benzylhydroxyphosphinyl]amino]pentanedioic acid;
2-[[(2-fluorobenzyl)hydroxyphosphinyl]amino]-2-pentanedioic acid;
2-[[((hydroxy)phenylmethyl)hydroxyphosphinyl]amino]pentanedioic acid;
2-[[(3-methylbenzyl)hydroxyphosphinyl]amino]pentanedioic acid;
2-[[(4-fluorophenyl)hydroxyphosphinyl]amino]pentanedioic acid;
2-[(phosphono)amino]pentanedioic acid;
2-[[(3-trifluoromethylbenzyl)hydroxyphosphinyl]amino]pentanedioic acid;
2-[(methylhydroxyphosphinyl)amino]hexanedioic acid;
2-[(benzylhydroxyphosphinyl)amino]hexanedioic acid;
2-[(methylhydroxyphosphinyl)amino]heptanedioic acid;

2-[(benzylhydroxyphosphinyl)amino]heptanedioic acid;
2-[(methylhydroxyphosphinyl)amino]octanedioic acid;
2-[(benzylhydroxyphosphinyl)amino]octanedioic acid;
2-[(methylhydroxyphosphinyl)amino]nonanedioic acid;
2-[(benzylhydroxyphosphinyl)amino]nonanedioic acid;
2-[(methylhydroxyphosphinyl)amino]decanedioic acid;
2-[(benzylhydroxyphosphinyl)amino]decanedioic acid;
3-[[(2-pyridyl)methylhydroxyphosphinyl]amino] pentanedioic acid;
3-[[(3-pyridyl)methylhydroxyphosphinyl]amino] pentanedioic acid;
3-[[(4-pyridyl)methylhydroxyphosphinyl]amino] pentanedioic acid;
3-[[(3-pyridyl)ethylhydroxyphosphinyl]amino]pentanedioic acid;
3-[[(3-pyridyl)propylhydroxyphosphinyl]amino] pentanedioic acid;
3-[[(tetrahydrofuranyl)methylhydroxyphosphinyl]amino] pentanedioic acid;
3-[[(tetrahydrofuranyl)ethylhydroxyphosphinyl]amino] pentanedioic acid;
3-[[(tetrahydrofuranyl)propylhydroxyphosphinyl]amino] pentanedioic acid;
3-[[(2-indolyl)methylhydroxyphosphinyl]amino] pentanedioic acid;
3-[[(3-indolyl)methylhydroxyphosphinyl]amino] pentanedioic acid;
3-[[(4-indolyl)methylhydroxyphosphinyl]amino] pentanedioic acid;
3-[[(3-indolyl)ethylhydroxyphosphinyl]amino]pentanedioic acid;
3-[[(3-indolyl)propylhydroxyphosphinyl]amino] pentanedioic acid;
3-[[(2-thienyl)methylhydroxyphosphinyl]amino] pentanedioic acid;
3-[[(3-thienyl)methylhydroxyphosphinyl]amino] pentanedioic acid;
3-[[(4-thienyl)methylhydroxyphosphinyl]amino] pentanedioic acid;
3-[[(3-thienyl)ethylhydroxyphosphinyl]amino]pentanedioic acid;
3-[[(3-thienyl)propylhydroxyphosphinyl]amino] pentanedioic acid; and
pharmaceutically acceptable salts and hydrates thereof.

In another preferred embodiment, $R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

Exemplary compounds of this embodiment include:
2-[[methylhydroxyphosphinyl]amino]-2-phenylethanoic acid;
2-[[ethylhydroxyphosphinyl]amino]-2-phenylethanoic acid;
2-[[propylhydroxyphosphinyl]amino]-2-phenylethanoic acid;
2-[[butylhydroxyphosphinyl]amino]-2-phenylethanoic acid;
2-[[cyclohexylhydroxyphosphinyl]amino]-2-phenylethanoic acid;
2-[[(cyclohexyl)methylhydroxyphosphinyl]amino]-2-phenylethanoic acid;
2-[[phenylhydroxyphosphinyl]amino]-2-phenylethanoic acid;
2-[[benzylhydroxyphosphinyl]amino]-2-phenylethanoic acid;
2-[[phenylethylhydroxyphosphinyl]amino]-2-phenylethanoic acid;
2-[[phenylpropylhydroxyphosphinyl]amino]-2-phenylethanoic acid;
2-[[phenylbutylhydroxyphosphinyl]amino]-2-phenylethanoic acid;
2-[[(2,3,4-trimethoxyphenyl)-3-hydroxyphosphinyl]amino]-2-phenylethanoic acid;
2-[[(1-naphthyl)hydroxyphosphinyl]amino]-2-phenylethanoic acid;
2-[[(2-naphthyl)hydroxyphosphinyl]amino]-2-phenylethanoic acid;
2-[[(1-naphthyl)methylhydroxyphosphinyl]amino]-2-phenylethanoic acid;
2-[[(2-naphthyl)methylhydroxyphosphinyl]amino]-2-phenylethanoic acid;
2-[[(1-naphthyl)ethylhydroxyphosphinyl]amino]-2-phenylethanoic acid;
2-[[(2-naphthyl)ethylhydroxyphosphinyl]amino]-2-phenylethanoic acid;
2-[[(1-naphthyl)propylhydroxyphosphinyl]amino]-2-phenylethanoic acid;
2-[[(2-naphthyl)propylhydroxyphosphinyl]amino]-2-phenylethanoic acid;
2-[[(1-naphthyl)butylhydroxyphosphinyl]amino]-2-phenylethanoic acid;
2-[[(2-naphthyl)butylhydroxyphosphinyl]amino]-2-phenylethanoic acid;
2-[[phenylprop-2-enylhydroxyphosphinyl]amino]-2-phenylethanoic acid;
2-[[benzylhydroxyphosphinyl]amino]-2-methylethanoic acid;
2-[[benzylhydroxyphosphinyl]amino]-2-ethylethanoic acid;
2-[[benzylhydroxyphosphinyl]amino]-2-propylethanoic acid;
2-[[benzylhydroxyphosphinyl]amino]-2-butylethanoic acid;
2-[[benzylhydroxyphosphinyl]amino]-2-cyclohexylethanoic acid;
2-[[benzylhydroxyphosphinyl]amino]-2-(cyclohexyl)methylethanoic acid;
2-[[benzylhydroxyphosphinyl]amino]-2-phenylethanoic acid;
2-[[benzylhydroxyphosphinyl]amino]-2-benzylethanoic acid;
2-[[benzylhydroxyphosphinyl]amino]-2-phenylethylethanoic acid;
2-[[benzylhydroxyphosphinyl]amino]-2-phenylpropylethanoic acid;
2-[[benzylhydroxyphosphinyl]amino]-2-phenylbutylethanoic acid;
2-[[benzylhydroxyphosphinyl]amino]-2-(2,3,4-trimethoxyphenyl)ethanoic acid;
2-[[benzylhydroxyphosphinyl]amino]-2-(1-naphthyl) ethanoic acid;
2-[[benzylhydroxyphosphinyl]amino]-2-(2-naphthyl) ethanoic acid;
2-[[benzylhydroxyphosphinyl]amino]-2-(1-naphthyl) methylethanoic acid;
2-[[benzylhydroxyphosphinyl]amino]-2-(2-naphthyl) methylethanoic acid;
2-[[benzylhydroxyphosphinyl]amino]-2-(1-naphthyl) ethylethanoic acid;
2-[[benzylhydroxyphosphinyl]amino]-2-(2-naphthyl) ethylethanoic acid;
2-[[benzylhydroxyphosphinyl]amino]-2-(1-naphthyl) propylethanoic acid;
2-[[benzylhydroxyphosphinyl]amino]-2-(2-naphthyl) propylethanoic acid;

2-[[benzylhydroxyphosphinyl]amino]-2-(1-naphthyl)butylethanoic acid;
2-[[benzylhydroxyphosphinyl]amino]-2-(2-naphthyl)butylethanoic acid;
2-[[benzylhydroxyphosphinyl]amino]-2-phenolprop-2-enylethanoic acid;
2-[[(2-pyridyl)methylhydroxyphosphinyl]amino]-2-phenylethanoic acid;
2-[[(3-pyridyl)methylhydroxyphosphinyl]amino]-2-phenylethanoic acid;
2-[[(4-pyridyl)methylhydroxyphosphinyl]amino]-2-phenylethanoic acid;
2-[[(3-pyridyl)ethylhydroxyphosphinyl]amino]-2-phenylethanoic acid;
2-[[(3-pyridyl)propylhydroxyphosphinyl]amino]-2-phenylethanoic acid;
2-[[(tetrahydrofuranyl)methylhydroxyphosphinyl]amino]-2-phenylethanoic acid;
2-[[(tetrahydrofuranyl)ethylhydroxyphosphinyl]amino]-2-phenylethanoic acid;
2-[[(tetrahydrofuranyl)propylhydroxyphosphinyl]amino]-2-phenylethanoic acid;
2-[[(2-indolyl)methylhydroxyphosphinyl]amino]-2-phenylethanoic acid;
2-[[(3-indolyl)methylhydroxyphosphinyl]amino]-2-phenylethanoic acid;
2-[[(4-indolyl)methylhydroxyphosphinyl]amino]-2-phenylethanoic acid;
2-[[(3-indolyl)ethylhydroxyphosphinyl]amino]-2-phenylethanoic acid;
2-[[(3-indolyl)propylhydroxyphosphinyl]amino]-2-phenylethanoic acid;
2-[[(2-thienyl)methylhydroxyphosphinyl]amino]-2-phenylethanoic acid;
2-[[(3-thienyl)methylhydroxyphosphinyl]amino]-2-phenylethanoic acid;
2-[[(4-thienyl)methylhydroxyphosphinyl]amino]-2-phenylethanoic acid;
2-[[(3-thienyl)ethylhydroxyphosphinyl]amino]-2-phenylethanoic acid;
2-[[(3-thienyl)propylhydroxyphosphinyl]amino]-2-phenylethanoic acid;
2-[[benzylhydroxyphosphinyl]amino]-2-(2-pyridyl)methylethanoic acid;
2-[[benzylhydroxyphosphinyl]amino]-2-(3-pyridyl)methylethanoic acid;
2-[[benzylhydroxyphosphinyl]amino]-2-(4-pyridyl)methylethanoic acid;
2-[[benzylhydroxyphosphinyl]amino]-2-(3-pyridyl)ethylethanoic acid;
2-[[benzylhydroxyphosphinyl]amino]-2-(3-pyridyl)propylethanoic acid;
2-[[benzylhydroxyphosphinyl]amino]-2-(tetrahydrofuranyl)methylethanoic acid;
2-[[benzylhydroxyphosphinyl]amino]-2-(tetrahydrofuranyl)ethylethanoic acid;
2-[[benzylhydroxyphosphinyl]amino]-2-(tetrahydrofuranyl)propylethanoic acid;
2-[[benzylhydroxyphosphinyl]amino]-2-(2-indolyl)methylethanoic acid;
2-[[benzylhydroxyphosphinyl]amino]-2-(3-indolyl)methylethanoic acid;
2-[[benzylhydroxyphosphinyl]amino]-2-(4-indolyl)methylethanoic acid;
2-[[benzylhydroxyphosphinyl]amino]-2-(3-indolyl)ethylethanoic acid;
2-[[benzylhydroxyphosphinyl]amino]-2-(3-indolyl)propylethanoic acid;
2-[[benzylhydroxyphosphinyl]amino]-2-(2-thienyl)methylethanoic acid;
2-[[benzylhydroxyphosphinyl]amino]-2-(3-thienyl)methylethanoic acid;
2-[[benzylhydroxyphosphinyl]amino]-2-(4-thienyl)methylethanoic acid;
2-[[benzylhydroxyphosphinyl]amino]-2-(3-thienyl)ethylethanoic acid;
2-[[benzylhydroxyphosphinyl]amino]-2-(3-thienyl)propylethanoic acid; and pharmaceutically acceptable salts and hydrates thereof.

Synthesis of NAALADase Inhibitors

The NAALADase inhibitors of formula I can be readily prepared by standard techniques of organic chemistry, utilizing the general synthetic pathways depicted below in Schemes I–IX. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

Scheme I

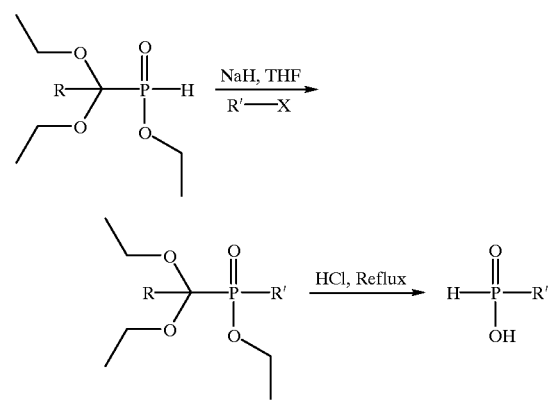

Methods of substituting the R group are known in the art. Additional methods of synthesizing phosphinic acid esters are described in *J. Med. Chem.*, Vol. 31, pp. 204–212 (1988), and set forth below in Scheme II.

Scheme II

Method A

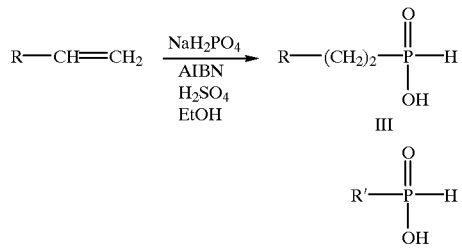

A. R' = (CH₃)₃Ph          H. R' = n-C₇H₁₅
B.      (CH₂)₄Ph              I.     n-C₈H₁₇
C.      (CH₂)₅Ph              J.     n-C₉H₁₉
D.      (CH₂)₄(P—F-Ph)        K.     CH₂CHCH₃C₄H₉
E.      (CH₂)₄-(3-pyridyl)    L.     CH₂(CH₃)C(CH₃)₂
F.      n-C₅H₁₁
G.      n-C₆H₁₃

Method B

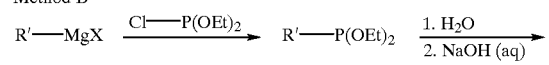

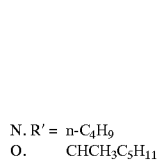

N. R' = n-C4H9
O.     CHCH3C5H11

Starting with the aforementioned phosphinic acid esters, there are a variety of routes for preparing the compounds of formula I. For example, a general route has been described in *J. Med. Chem.*, Vol. 39, pp. 619–622 (1996), and is set forth below in Scheme III.

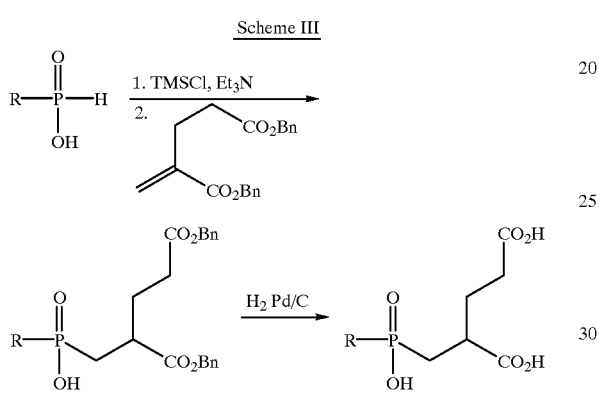

Other routes for preparing the compounds of formula I are set forth below in Scheme IV and Scheme V. Scheme IV and Scheme V show the starting material as a phosphinic acid derivative and the R group as any reasonable chemical substituent including without limitation the substituents listed in Scheme II and throughout the specification.

Another route for preparing the compounds of formula I allows for aromatic substitution at $R_1$, and is set forth below in Scheme VI.

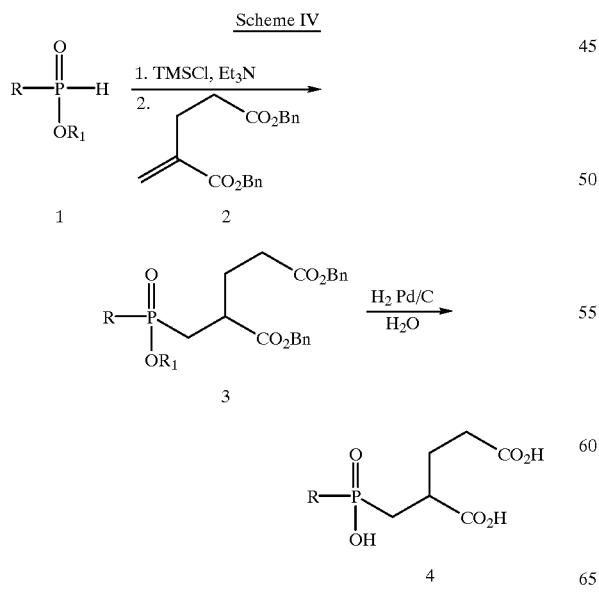

-continued

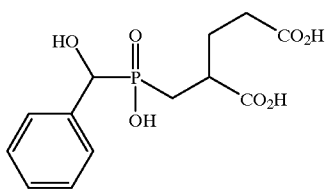

9

Another route for preparing the compounds of formula I allows for aromatic substitution at the $R_2$ position, and is set forth below in Scheme VII.

Scheme VII

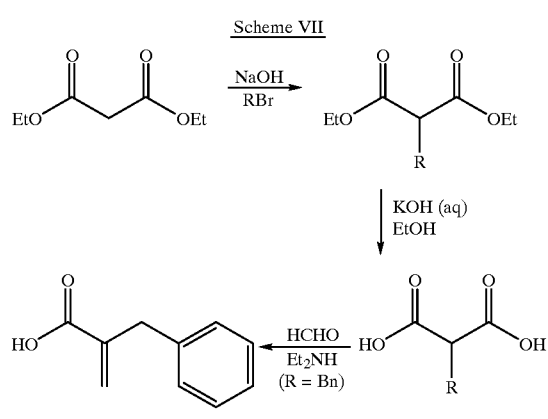

Another route for preparing the compounds of formula I wherein X is $NR_1$ is set forth below in Scheme VIII.

Scheme VIII

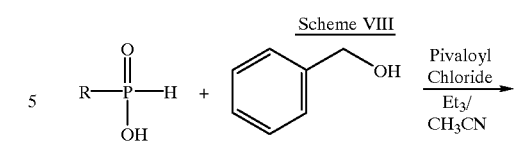

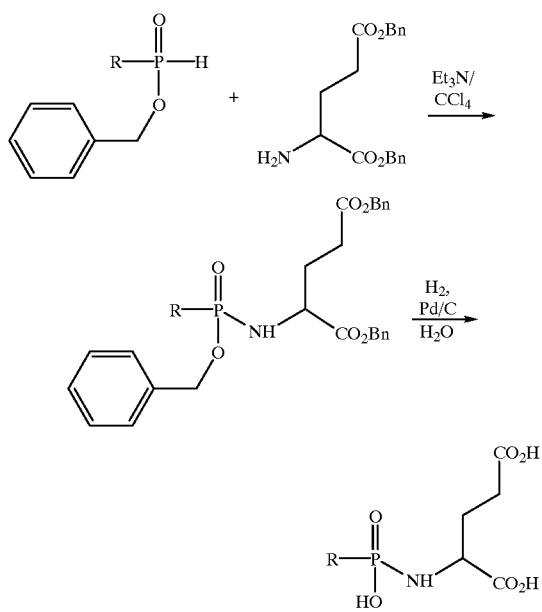

Another route for preparing the compounds of formula I wherein X is oxygen is set forth below in Scheme IX.

Scheme IX

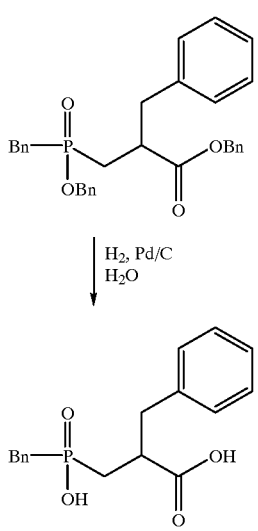

METHODS OF THE PRESENT INVENTION

METHODS OF TREATING A GLUTAMATE ABNORMALITY

Although not limited to any one particular theory, it is believed that the NAALADase inhibitors used in the methods of the present invention modulate levels of glutamate by acting on a storage form of glutamate which is hypothesized to be upstream from the effects mediated by the NMDA receptor.

Accordingly, the present invention further relates to a method of treating a glutamate abnormality in an animal, comprising administering an effective amount of a NAALADase inhibitor to said animal.

The glutamate abnormality may be any disease, disorder or condition in which glutamate is implicated, including pathological conditions involving elevated levels of glutamate. Examples of glutamate abnormalities include without limitation epilepsy, stroke, Alzheimer's disease, Parkinson's Disease, Amyotrophic Lateral Sclerosis (ALS), Huntington's Disease, schizophrenia, chronic pain, ischemia, peripheral neuropathy, traumatic brain injury and physical damage to the spinal cord. In a preferred embodiment, the glutamate abnormality is selected from the group consisting of stroke, Parkinson's Disease, Amyotrophic Lateral Sclerosis (ALS) and spinal cord injury.

The NAALADase inhibitor may be administered alone or in combination with at least one additional therapeutic agent.

A preferred NAALADase inhibitor is a glutamate-derived hydroxyphosphinyl derivative, an acidic peptide analog or a mixture thereof.

A preferred acidic peptide analog is an amino acid sequence selected from the group consisting of Asp-Glu, Glu-Glu, Gly-Glu, gamma-Glu-Glu and Glu-Glu-Glu.

A preferred NAALADase inhibitor is a glutamate-derived hydroxyphosphinyl derivative of formula I:

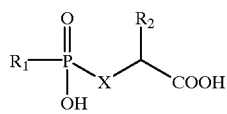

or a pharmaceutically acceptable salt or hydrate thereof, wherein:

$R_1$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or mixtures thereof;

X is $CR_3R_4$, O or $NR_1$;

$R_3$ and $R_4$ are independently selected from the group consisting of hydrogen, $C_1$–$C_6$ straight or branched chain alkyl, $C_2$–$C_6$ straight or branched chain alkenyl, $C_3$–$C_8$ cycloalkyl, $C_5$–$C_7$ cycloalkenyl, Ar, halo and mixtures thereof;

$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, Ar or mixtures thereof;

Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino or mixtures thereof.

Preferably, X is $CH_2$.

More preferably, $R_2$ is substituted with carboxy.

Even more preferably, $R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof; and $R_2$ is $C_1$–$C_2$ alkyl.

Most preferably, the glutamate-derived hydroxyphosphinyl derivative is selected from the group consisting of:

2-(phosphonomethyl)pentanedioic acid;
2-(phosphonomethyl)succinic acid;
2-[[(2-carboxyethyl)hydroxyphosphinyl]methyl] pentanedioic acid;
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[(cyclohexyl)methylhydroxyphosphinyl]methyl] pentanedioic acid;
2-[[phenylhydroxyphosphinyl]methyl]pentanedioic acid;
2-[(benzylhydroxyphosphinyl)methyl]pentanedioic acid;
2-[[(phenylmethyl)hydroxyphosphinyl]methyl]pentanedioic acid;
2-[[(phenylethyl)hydroxyphosphinyl]methyl]pentanedioic acid;
2-[[(phenylpropyl)hydroxyphosphinyl]methyl]pentanedioic acid;
2-[[(phenylbutyl)hydroxyphosphinyl]methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(methoxybenzyl)hydroxyphosphinyl]methyl] pentanedioic acid;
2-[[(2,3,4-trimethoxyphenyl)hydroxyphosphinyl]methyl] pentanedioic acid;
2-[[(phenylprop-2-enyl)hydroxyphosphinyl]methyl] pentanedioic acid;
2-[[(2-fluorobenzyl)hydroxyphosphinyl]methyl] pentanedioic acid;
2-[[((hydroxy)phenylmethyl)hydroxyphosphinyl]methyl] pentanedioic acid;
2-[[(3-methylbenzyl)hydroxyphosphinyl]methyl] pentanedioic acid;
2-[[(4-fluorophenyl)hydroxyphosphinyl]methyl] pentanedioic acid;

2-[[(3-trifluoromethylbenzyl)hydroxyphosphinyl]methyl] pentanedioic acid; and pharmaceutically acceptable salts and hydrates thereof.

Examples of other glutamate-derived hydroxyphosphinyl derivatives useful for the present method are identified above with respect to pharmaceuticals compositions.

METHODS OF EFFECTING A NEURONAL ACTIVITY

The inventors have discovered that inhibition of NAALADase promotes nerve regeneration and myelin formation.

Accordingly, the present invention also relates to a method of effecting a neuronal activity in an animal, comprising administering an effective amount of a NAALADase inhibitor to said animal.

The neuronal activity that is effected by the method of the present invention may be selected from the group consisting of: stimulation of damaged neurons, promotion of neuronal regeneration, prevention of neurodegeneration and treatment of a neurological disorder.

Examples of a neurological disorder that is treatable by the method of the present invention include without limitation: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; and Parkinson's disease.

The method of the present invention is particularly useful for treating a neurological disorder selected from the group consisting of: peripheral neuropathy caused by physical injury or disease state, traumatic brain injury, physical damage to the spinal cord, stroke associated with brain damage, demyelinating diseases and neurological disorders relating to neurodegeneration. Examples of demyelinating diseases include multiple sclerosis. Examples of neurological disorders relating to neurodegeneration include Alzheimer's Disease, Parkinson's Disease, and amyotrophic lateral sclerosis (ALS).

The NAALADase inhibitor may be administered alone or in combination with at least one additional therapeutic agent.

A preferred NAALADase inhibitor is a glutamate-derived hydroxyphosphinyl derivative, an acidic peptide analog or a mixture thereof.

A preferred acidic peptide analog is an amino acid sequence selected from the group consisting of Asp-Glu, Glu-Glu, Gly-Glu, gamma-Glu-Glu and Glu-Glu-Glu.

A preferred NAALADase inhibitor is a glutamate-derived hydroxyphosphinyl derivative of formula I:

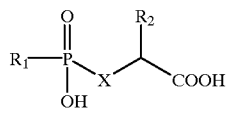

I or a pharmaceutically acceptable salt or hydrate thereof, wherein:

$R_1$ is selected from the group consisting of hydrogen, $C_1-C_9$ straight or branched chain alkyl, $C_2-C_9$ straight or branched chain alkenyl, $C_3-C_8$ cycloalkyl, $C_5-C_7$ cycloalkenyl and Ar, wherein said $R_1$ is unsubstituted or substituted with carboxy, $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_9$ alkoxy, $C_2-C_9$ alkenyloxy, phenoxy, benzyloxy, amino, Ar or mixtures thereof;

X is $CR_3R_4$, O or $NR_1$;

$R_3$ and $R_4$ are independently selected from the group consisting of hydrogen, $C_1-C_6$ straight or branched chain alkyl, $C_2-C_6$ straight or branched chain alkenyl, $C_3-C_8$ cycloalkyl, $C_5-C_7$ cycloalkenyl, Ar, halo and mixtures thereof;

$R_2$ is selected from the group consisting of hydrogen, $C_1-C_9$ straight or branched chain alkyl, $C_2-C_9$ straight or branched chain alkenyl, $C_3-C_8$ cycloalkyl, $C_5-C_7$ cycloalkenyl and Ar, wherein said $R_2$ is unsubstituted or substituted with carboxy, $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_6$ alkoxy, $C_2-C_6$ alkenyloxy, phenoxy, benzyloxy, amino, Ar or mixtures thereof;

Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1-C_6$ straight or branched chain alkyl, $C_2-C_6$ straight or branched chain alkenyl, $C_1-C_6$ alkoxy, $C_2-C_6$ alkenyloxy, phenoxy, benzyloxy, amino or mixtures thereof.

Preferably, X is $CH_2$.

More preferably, $R_2$ is substituted with carboxy.

Even more preferably, $R_1$ is hydrogen, $C_1-C_4$ straight or branched chain alkyl, $C_2-C_4$ straight or branched chain alkenyl, $C_3-C_8$ cycloalkyl, $C_5-C_7$ cycloalkenyl, benzyl or phenyl, wherein said $R_1$ is unsubstituted or substituted with carboxy, $C_3-C_8$ cycloalkyl, $C_5-C_7$ cycloalkenyl, halo, hydroxy, nitro, trifluoromethyl, $C_1-C_6$ straight or branched chain alkyl, $C_2-C_6$ straight or branched chain alkenyl, $C_1-C_4$ alkoxy, $C_2-C_4$ alkenyloxy, phenoxy, benzyloxy, amino, benzyl, phenyl or mixtures thereof; and $R_2$ is $C_1-C_2$ alkyl.

Most preferably, the glutamate-derived hydroxyphosphinyl derivative is selected from the group consisting of:

2-(phosphonomethyl)pentanedioic acid;

2-(phosphonomethyl)succinic acid;

2-[[(2-carboxyethyl)hydroxyphosphinyl]methyl] pentanedioic acid;

2-[[methylhydroxyphosphinyl]methyl]pentanedioic acid;

2-[[ethylhydroxyphosphinyl]methyl]pentanedioic acid;

2-[[propylhydroxyphosphinyl]methyl]pentanedioic acid;

2-[[butylhydroxyphosphinyl]methyl]pentanedioic acid;

2-[[cyclohexylhydroxyphosphinyl]methyl]pentanedioic acid;

2-[[(cyclohexyl)methylhydroxyphosphinyl]methyl] pentanedioic acid;

2-[[phenylhydroxyphosphinyl]methyl]pentanedioic acid;

2-[(benzylhydroxyphosphinyl)methyl]pentanedioic acid;

2-[[(phenylmethyl)hydroxyphosphinyl]methyl]pentanedioic acid;

2-[[(phenylethyl)hydroxyphosphinyl]methyl]pentanedioic acid;

2-[[(phenylpropyl)hydroxyphosphinyl]methyl]pentanedioic acid;

2-[[(phenylbutyl)hydroxyphosphinyl]methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(methoxybenzyl)hydroxyphosphinyl]methyl] pentanedioic acid;
2-[[(2,3,4-trimethoxyphenyl)hydroxyphosphinyl]methyl] pentanedioic acid;
2-[[(phenylprop-2-enyl)hydroxyphosphinyl]methyl] pentanedioic acid;
2-[[(2-fluorobenzyl)hydroxyphosphinyl]methyl] pentanedioic acid;
2-[[((hydroxy)phenylmethyl)hydroxyphosphinyl]methyl] pentanedioic acid;
2-[[(3-methylbenzyl)hydroxyphosphinyl]methyl] pentanedioic acid;
2-[[(4-fluorophenyl)hydroxyphosphinyl]methyl] pentanedioic acid;
2-[[(3-trifluoromethylbenzyl)hydroxyphosphinyl]methyl] pentanedioic acid; and pharmaceutically acceptable salts and hydrates thereof.

Examples of other glutamate-derived hydroxyphosphinyl derivatives useful for the present method are identified above with respect to pharmaceuticals compositions.

ROUTE OF ADMINISTRATION

In the methods of the present invention, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the NAALADase inhibitors used in the methods of the present invention should readily penetrate the blood-brain barrier when peripherally administered. Compounds which cannot penetrate the blood-brain barrier can be effectively administered by an intraventricular route.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their poly-oxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The NAALADase inhibitors used in the methods of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

DOSAGE

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

In a preferred embodiment, the NAALADase inhibitors are administered in lyophilized form. In this case, 1 to 100 mg of a NAALADase inhibitor may be lyophilized in individual vials, together with a carrier and a buffer, such as mannitol and sodium phosphate. The compound may be reconstituted in the vials with bacteriostatic water before administration.

In treating global ischemia, the NAALADase inhibitors are preferably administered orally, rectally, parenterally or topically at least 1 to 6 times daily, and may follow an initial bolus dose of higher concentration.

As previously mentioned, the NAALADase inhibitors used in the methods of the present invention may be administered in combination with one or more therapeutic agents. Specific dose levels for these agents will depend upon considerations such as those identified above for the NAALADase inhibitors.

ADMINISTRATION REGIMEN

For the methods of the present invention, any administration regimen regulating the timing and sequence of drug delivery can be used and repeated as necessary to effect treatment. Such regimen may include pretreatment and/or co-administration with additional therapeutic agents.

To maximize protection of nervous tissue from nervous insult, the NAALADase inhibitors should be administered to the affected cells as soon as possible. In situations where nervous insult is anticipated, the compounds should be administered before the expected nervous insult. Such situations of increased likelihood of nervous insult include surgery (cartoid endarterectomy, cardiac, vascular, aortic, orthopedic); endovascular procedures such as arterial catherization (cartoid, vertebral, aortic, cardia, renal, spinal, Adamkiewicz); injections of embolic agents; coils or balloons for hemostasis; interruptions of vascularity for treatment of brain lesions; and predisposing medical conditions such as crescendo transient ischemic attacks, emboli and sequential strokes. Where pretreatment for stroke or ischemia is impossible or impracticable, it is important to get the NAALADase inhibitors to the affected cells as soon as possible during or after the event. In the time period between strokes, diagnosis and treatment procedures should be minimized to save the cells from further damage and death.

COMBINATION WITH OTHER TREATMENTS

In methods of treating nervous insult (particularly acute ischemic stroke and global ischemia caused by drowning and head trauma), the NAALADase inhibitors can be co-administered with one or more therapeutic agents, preferably agents which can reduce the risk of stroke (such as aspirin), and more preferably agents which can reduce the risk of a second ischemic event (such as ticlopidine).

The NAALADase inhibitors can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a NAALADase inhibitor, as well as one or more pharmaceutical excipients, such as wetting, emulsifying and pH buffering agents.

In Vivo Toxicity of NAALADase Inhibitors

To examine the toxicological effect of NAALADase inhibition in vivo, a group of mice were injected with 2-(phosphonomethyl) pentanedioic acid, a NAALADase inhibitor of high activity, in doses of 1, 5, 10, 30, 100, 300 and 500 mg/kg body weight. The mice were subsequently observed two times per day for 5 consecutive days. The survival rate at each dose level is provided below in TABLE I. The results show that the NAALADase inhibitor is non-toxic to mice, suggesting that it would be similarly non-toxic to humans when administered at therapeutically effective amounts.

TABLE I

TOXICOLOGICAL EFFECTS OF NAALADASE INHIBITORS

| Dose (mg/kg) | 1 | 5 | 10 | 30 | 100 | 300 | 500 |
|---|---|---|---|---|---|---|---|
| Survival Rate After 5 days (%) | 100 | 100 | 100 | 100 | 100 | 100 | 66.7 |

In Vitro Inhibition of NAALADase Activity

Various compounds of formula I were tested for in vitro inhibition of NAALADase activity. The results are provided below in Table III.

TABLE II

IN VITRO INHIBITION OF NAALADASE ACTIVITY

| Compound | $K_i$ (nM) |
|---|---|
| 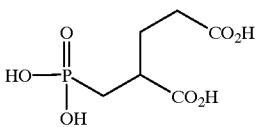<br>2-(phosphonomethyl)pentanedioic acid | 0.293 ± 0.08 |
| 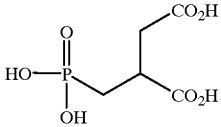<br>2-(phosphonomethyl) succinic acid | 700.00 ± 67.3 |
| 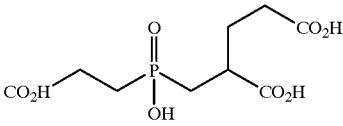<br>2-[[(2-carboxyethyl)hydroxyphosphinyl]-methyl]pentanedioic acid | 1.89 ± 0.19 |
| 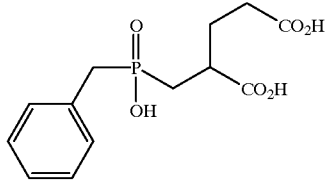 | 34.15 |

TABLE II-continued

IN VITRO INHIBITION OF NAALADASE ACTIVITY

| Compound | $K_i$ (nM) |
|---|---|
| phenyl-P(O)(OH)-CH$_2$-CH(CO$_2$H)-CH$_2$-CH$_2$-CO$_2$H | 35.85 |
| HO-CH(phenyl)-P(O)(OH)-CH$_2$-CH(CO$_2$H)-CH$_2$-CH$_2$-CO$_2$H | 54.50 |
| butyl-P(O)(OH)-CH$_2$-CH(CO$_2$H)-CH$_2$-CH$_2$-CO$_2$H | 113.50 |
| (3-methylphenyl)-P(O)(OH)-CH$_2$-CH(CO$_2$H)-CH$_2$-CH$_2$-CO$_2$H | 180.00 |
| phenyl-CH$_2$-CH$_2$-P(O)(OH)-CH$_2$-CH(CO$_2$H)-CH$_2$-CH$_2$-CO$_2$H | 148.50 |
| phenyl-CH$_2$-CH$_2$-CH$_2$-P(O)(OH)-CH$_2$-CH(CO$_2$H)-CH$_2$-CH$_2$-CO$_2$H | 231.67 |
| (4-fluorophenyl)-P(O)(OH)-CH$_2$-CH(CO$_2$H)-CH$_2$-CH$_2$-CO$_2$H | 532.00 |
| methyl-P(O)(OH)-CH$_2$-CH(CO$_2$H)-CH$_2$-CH$_2$-CO$_2$H | 1100.00 |
| (4-methylphenyl)-CH$_2$-P(O)(OH)-CH$_2$-CH(CO$_2$H)-CH$_2$-CH$_2$-CO$_2$H | 68.00 |
| (4-fluorophenyl)-CH$_2$-P(O)(OH)-CH$_2$-CH(CO$_2$H)-CH$_2$-CH$_2$-CO$_2$H | 70.00 |
| (4-methoxyphenyl)-CH$_2$-P(O)(OH)-CH$_2$-CH(CO$_2$H)-CH$_2$-CH$_2$-CO$_2$H | 89.50 |
| (2-fluorophenyl)-CH$_2$-P(O)(OH)-CH$_2$-CH(CO$_2$H)-CH$_2$-CH$_2$-CO$_2$H | 145.00 |
| (pentafluorophenyl)-CH$_2$-P(O)(OH)-CH$_2$-CH(CO$_2$H)-CH$_2$-CH$_2$-CO$_2$H | 22.67 |
| (4-methylphenyl)-P(O)(OH)-CH$_2$-CH(CO$_2$H)-CH$_2$-CH$_2$-CO$_2$H | 204.00 |

TABLE II-continued

IN VITRO INHIBITION OF NAALADASE ACTIVITY

| Compound | $K_i$ (nM) |
|---|---|
| (phenethyl-CH(CO2H)-CH2-P(O)(OH)-OH) | 199.00 |
| (HO-P(O)(OH)-CH2-CH(CO2H)-(CH2)3-CO2H) | 185.00 |
| (4-benzyloxybenzyl-P(O)(OH)-CH2-CH(CO2H)-CH2-CO2H) | 177.00 |
| (3-trifluoromethylbenzyl-P(O)(OH)-CH2-CH(CO2H)-CH2-CO2H) | 22.50 |
| (2-trifluoromethylbenzyl-P(O)(OH)-CH2-CH(CO2H)-CH2-CO2H) | 92.00 |
| (4-hydroxybenzyl-P(O)(OH)-CH2-CH(CO2H)-CH2-CO2H) | 117.00 |

The results show that 2-(phosphonomethyl)pentanedioic acid exhibits high NAALADase inhibiting activity, with a $K_i$ of 0.293 nM. The activity of this compound is over 1000 times greater than that of previously described NAALADase inhibitors.

By comparison, 2-(phosphonomethyl)succinic acid exhibits much lower NAALADase inhibiting activity, suggesting that a glutamate analog attached to the phosphonic acid contributes to its NAALADase inhibiting activity.

The results also show that 2-[[(2-carboxyethyl)hydroxyphosphinyl]methyl]pentanedioic acid, which has an additional carboxylic acid side chain similar to the aspartate residue found in NAAG, exhibits a lower NAALADase inhibiting activity than 2-(phosphonomethyl)pentanedioic acid.

Protocol for Assaying In Vitro Inhibition of NAALADase Activity

The amount of [$^3$H]Glu liberated from [$^3$H]NAAG in 50 mM Tris-Cl buffer was measured for 15 minutes at 37° C. using 30–50 μg of synaptosomal protein. Substrate and product were resolved by anion-exchange liquid chromatography. Duplicate assays were performed so that no more than 20% of the NAAG was digested, representing the linear range of peptidase activity. Quisqualate (100 μM) was included in parallel assay tubes to confirm the specificity of the measurements.

In Vitro Assay of NAALADase Inhibitors on Ischemia

To examine the in vitro effect of NAALADase inhibitors on ischemia, cortical cell cultures were treated with various compounds of formula I during an ischemic insult (potassium cyanide and 2-deoxyglucose) and for one hour thereafter (for experimental details, see Vornov et al., *J. Neurochem*, Vol. 65, No. 4, pp. 1681–1691 (1995)).

The neuroprotective effect of each tested compound is provided below in TABLE III (a). Neuroprotective effect is expressed as $EC_{50}$, the concentration which is required to cause a 50% reduction in glutamate toxicity following an ischemic insult.

TABLE III(a)

| Compound | $EC_{50}$ (nM) |
|---|---|
| (HO-P(O)(OH)-CH2-CH(CO2H)-CH2-CO2H) | 0.67 |
| (phenethyl-CH(CO2H)-CH2-P(O)(OH)-OH) | 373.0 |

TABLE III(a)-continued

| Compound | EC$_{50}$ (nM) |
|---|---|
| [3-(trifluoromethyl)benzyl phosphinate pentanedioic acid structure] | 112.0 |
| [benzyl phosphinate pentanedioic acid structure] | 132.0 |
| [phenyl phosphinate pentanedioic acid structure] | 100.0 |
| [hydroxy(phenyl)methyl phosphinate pentanedioic acid structure] | 767.0 |
| [butyl phosphinate pentanedioic acid structure] | 794.0 |
| [4-methylbenzyl phosphinate pentanedioic acid structure] | 37.00 |
| [4-fluorobenzyl phosphinate pentanedioic acid structure] | 79.00 |
| [pentafluorobenzyl phosphinate pentanedioic acid structure] | 2.00 |
| [phenethyl phosphinate pentanedioic acid structure] | 834.00 |
| [3-phenylpropyl phosphinate pentanedioic acid structure] | 4315.00 |
| [4-methoxybenzyl phosphinate pentanedioic acid structure] | 1670.00 |

The dose-response of this effect, as measured by the % toxicity at different concentrations of 2-(phosphonomethyl)pentanedioic acid, is provided below in TABLE III(b) and graphically presented in FIG. 1.

TABLE III(b)

| Dose | % Toxicity | |
|---|---|---|
| Control | 100.00 ± 9.0 | (n = 5) |
| 100 pM | 66.57 ± 4.38 | (n = 5) |
| 1 nM | 42.31 ± 9.34 | (n = 5) |
| 10 nM | 33.08 ± 9.62 | (n = 5) |
| 100 nM | 30.23 ± 9.43 | (n = 5) |
| 1 µM | 8.56 ± 8.22 | (n = 5) |

The results show that toxicity decreased as the concentration of 2-(phosphonomethyl)pentanedioic acid increased, suggesting that NAALADase inhibitors would be effective in treating ischemia or neuronal damage caused by ischemia.

The methods for this assay are described in detail below. Specifically, cell cultures were exposed to potassium cyanide and 2-deoxyglucose (2-DG)(10 mM) and analyzed for release of lactate dehydrogenase (LDH).

In Vitro Toxicity of NAAG

To examine the in vitro toxicity of NAAG, cortical cell cultures were treated with NAAG (in concentrations ranging from 3 $\mu$M to 3 mM) for 20 minutes. The toxicity measurement for each concentration of NAAG is provided below in TABLE IV and graphically presented in FIG. 2.

TABLE IV

| Dose of NAAG | % Toxicity | |
|---|---|---|
| 3 $\mu$M | 3.51 | (n = 1) |
| 10 $\mu$M | 4.30 ± 3.12 | (n = 3) |
| 30 $\mu$M | 11.40 ± 6.17 | (n = 3) |
| 100 $\mu$M | 12.66 ± 5.50 | (n = 3) |
| 300 $\mu$M | 13.50 ± 4.0 | (n = 3) |
| 1 mM | 21.46 ± 4.20 | (n = 3) |
| 3 mM | 45.11 ± 4.96 | (n = 3) |

The results show that toxicity increased as the concentration of NAAG increased. The toxicity is attributed to the release of glutamate by NAAG when cleaved by NAALADase.

In Vitro Assay of NAALADase Inhibitors on Toxicity of NAAG

To examine the effect of NAALADase inhibitors on in vitro toxicity of NAAG, cortical cell cultures were treated with 2-(phosphonomethyl)pentanedioic acid (1 $\mu$M) during exposure to NAAG and for one hour thereafter. The toxicity measurement for each concentration of NAAG is provided below in TABLE V and graphically presented in FIG. 3.

TABLE V

| Dose of NAAG | % Toxicity | |
|---|---|---|
| 3 $\mu$M | −4.71 | (n = 1) |
| 10 $\mu$M | −3.08 ± 0.81 | (n = 3) |
| 30 $\mu$M | −4.81 ± 1.13 | (n = 3) |
| 100 $\mu$M | −2.87 ± 0.78 | (n = 3) |
| 300 $\mu$M | −2.09 ± 0.48 | (n = 3) |
| 1 mM | 0.26 ± 1.11 | (n = 3) |
| 3 mM | 16.83 ± 8.76 | (n = 3) |

Figure 2:
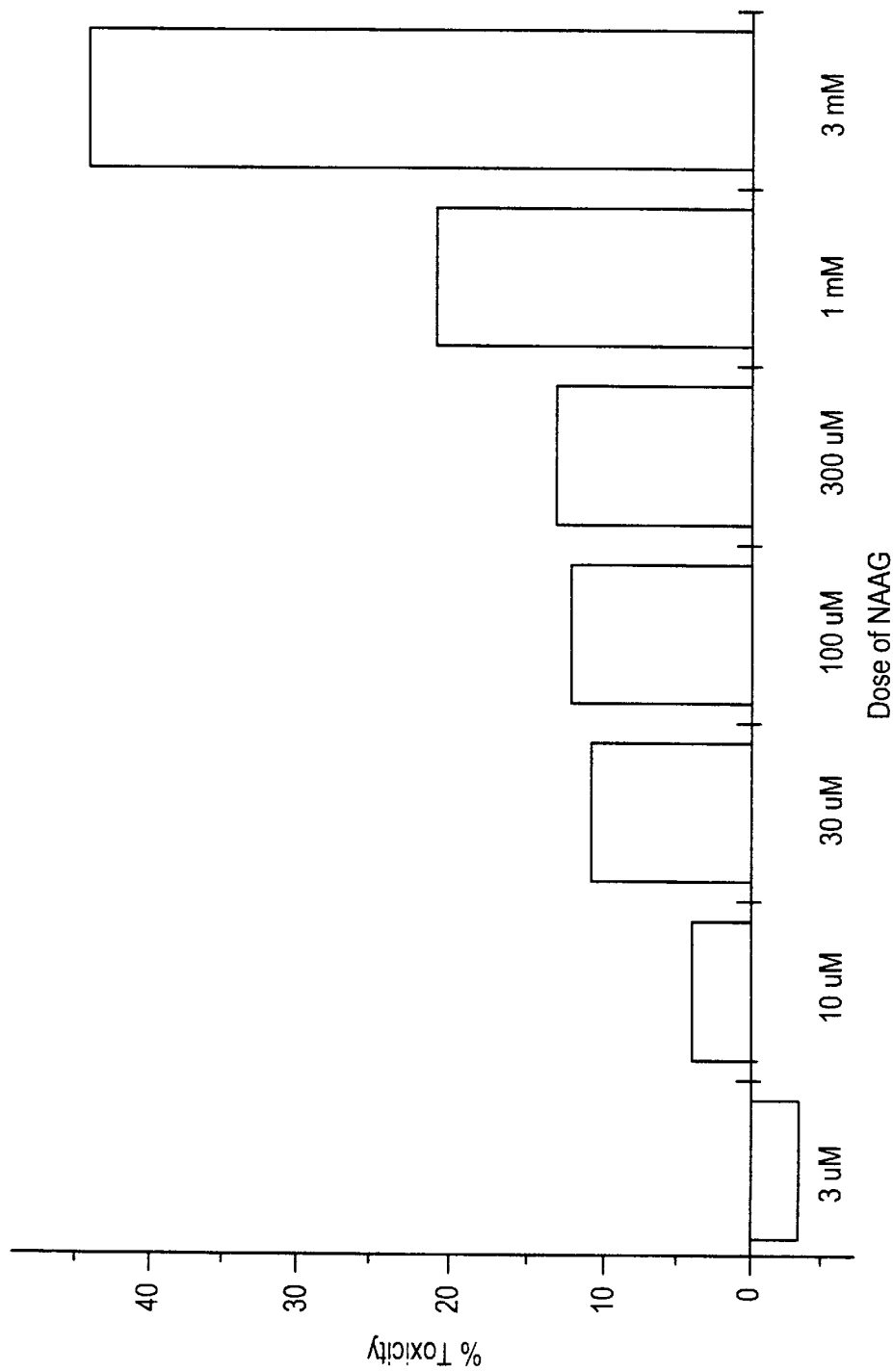
FIG. 2 is a bar graph plotting in vitro toxicity against various doses of NAAG to which cortical cell cultures were exposed.
Figure 3:
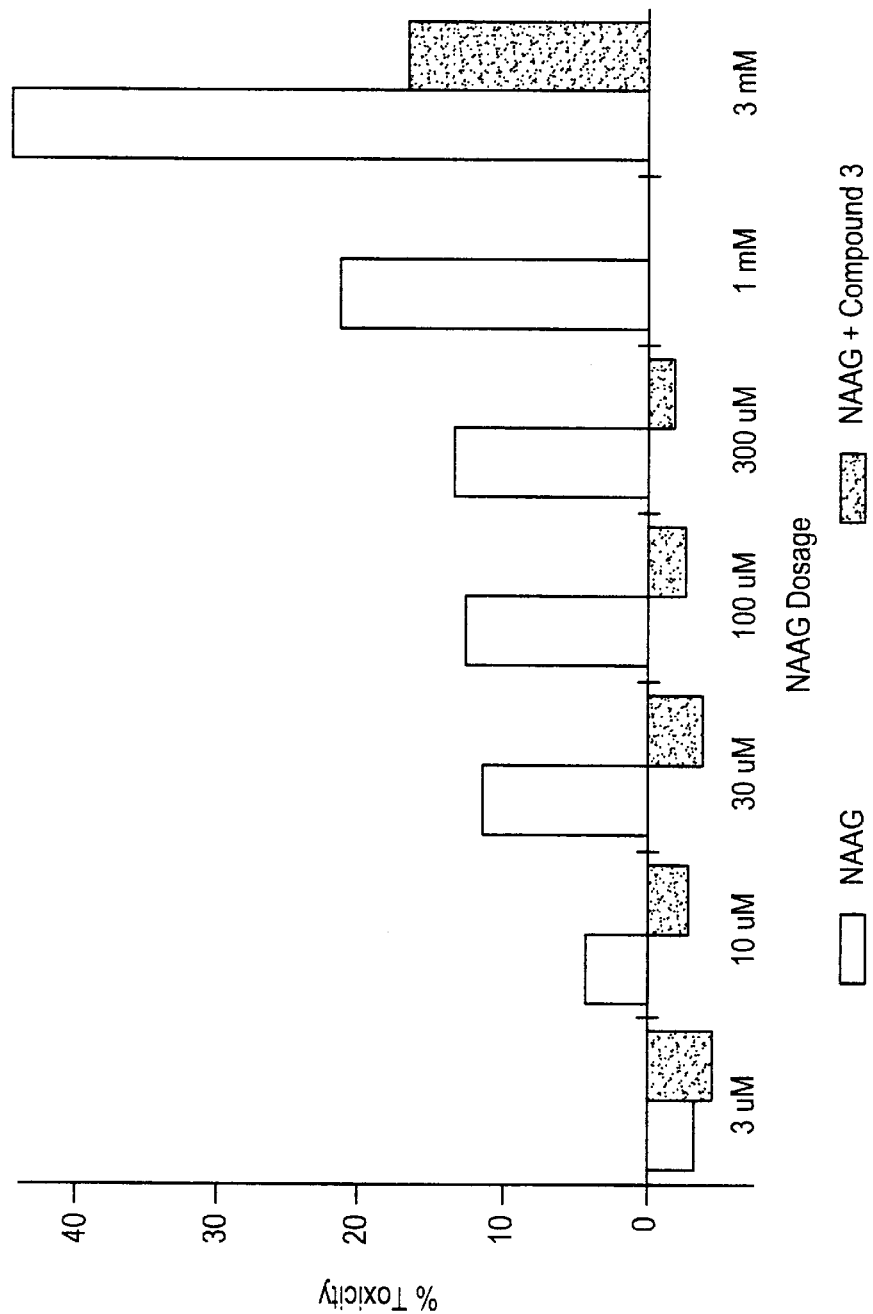
FIG. 3 is a bar graph plotting in vitro toxicity following treatment with 2-(phosphonomethyl)pentanedioic acid, against various doses of NAAG to which cortical cell cultures were exposed.

When compared to the results of FIG. 2/TABLE IV, the results of FIG. 3/TABLE V show that toxicity decreased considerably after treatment with the NAALADase inhibitor, suggesting that it would be effective in treating glutamate abnormalities.

Figure 4:
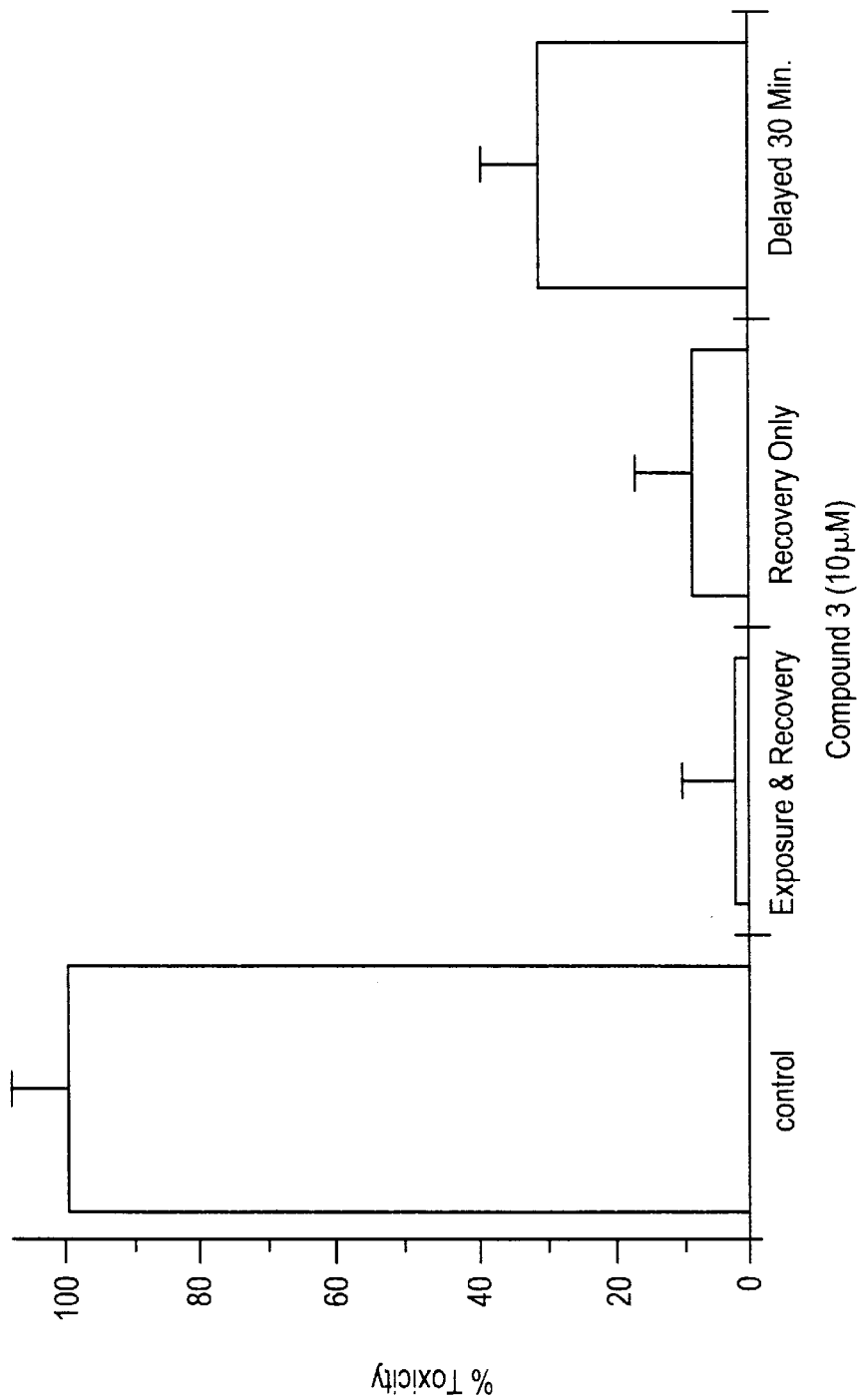
FIG. 4 is a bar graph plotting in vitro toxicity of ischemic insult against various times at which cortical cell cultures were treated with 2-(phosphonomethyl)-pentanedioic acid.

In Vitro Assay of NAALADASE Inhibitors on Ischemia at Different Times of Administration To examine the effect of NAALADase inhibitors on in vitro ischemic toxicity at different times of administration, cortical cell cultures were treated with 2-(phosphonomethyl) pentanedioic acid (i) during an ischemic insult and for one hour thereafter (exposure and recovery); (ii) for one hour following ischemic insult (recovery only); and (iii) for one hour beginning 30 minutes after ischemic insult (delayed 30 minutes). The toxicity measurement for each time of administration is provided below in TABLE VI and graphically presented in FIG. 4.

TABLE VI

| Time of Administration Relative to Ischemic Insult | % Toxicity |
|---|---|
| Control | 100.00% |
| Exposure & Recovery | 2.54% |

TABLE VI-continued

| Time of Administration Relative to Ischemic Insult | % Toxicity |
|---|---|
| Recovery Only | 9.03% |
| Delayed 30 Minutes | 31.49% |

The results show that significant neuronal protection is achieved when NAALADase inhibitors are administered during exposure and recovery from an ischemic insult, and even after a 30 minute delay following the ischemic insult.

Protocol for In Vitro Toxicity Assay a. Cell Culture

Dissociated cortical cell cultures are prepared using the papain-dissociation method of Heuttner and Baughman (1986) as modified by Murphy and Baraban (1990). See TABLE VII for the Dissociated Culture Protocol as used herein. Fetuses of embryonic day 17 are removed from timed pregnancy rats (Harlan Sprague Dawley). The cortex is rapidly dissected out in Dulbecco's phosphate-buffered saline, stripped of meninges, and incubated in a papain solution for 15 minutes at 37° C. The tissue is then mechanically triturated and pelleted at 500 g (1000–2000 rpm on swinging bucket Beckman). The pellet is resuspended in a DNAase solution, triturated with a 10 ml pipette ×15–20, layered over a "10×10" solution containing albumin and trypsin inhibitor (see TABLE VII for an example of a "10×10" solution), repelleted, and resuspended in a plating medium containing 10% fetal bovine serum (HyClone A-1111-L), 5% heat-inactivated Equine serum (HyClone A-3311-L), and 84% modified Earle's basal medium (MEM) (Gibco 51200–020) with high glucose (4.5 g/L) and 1 g/L NaHCO$_3$. Each 24-well plate is pretreated with poly-D-lysine (0.5 ml/well of 10 $\mu$g/ml) for 1 h and rinsed with water before plating. Cultures are plated at 2.5×10$^6$ cells/ml with each well of a 24 well plate receiving 500 $\mu$l/well. Alternatively, 35 mm dishes can be plated at 2 ml/dish, 6 well plates at 2 ml/well, or 12 well plates at 1 ml/well. After plating, 50% of the medium is changed every 3–4 days with growth serum containing 5% heat-inactivated Equine serum (HyClone A-3311-L), 95% modified Earle's basal medium (MEM) (Gibco 51200–020), and 1% L-Glutamine (Gibco 25030–081). Experiments are performed after 21 days in cultures. Cultures are maintained in a 5% CO$_2$ atmosphere at 37° C. These methodologies are described in further detail below in the TABLE VII.

TABLE VII

DISSOCIATED CULTURE PROTOCOL

I. PREPARE SOLUTIONS
Stocks/Solutions

| | |
|---|---|
| DNAase Stock, 1 ml (100x) 5 mg DNAase I (Worthington LS002004); 1 ml dissoc. EBSS; freeze as 50 $\mu$l aliquots. | Dulbecco's PBS. 500 ml 4 gm NaCl (J.T. Baker 3624-01); 1.06 gm Na$_2$HPO$_4$.7H$_2$O (Fisher S373-3); 100 mg KCl (Fisher P217-500); 100 mg KH$_2$PO$_4$ (Sigma P-0662); 500 ml dH$_2$O; adjust pH to 7.4 and sterile filter. |
| Dissociated EBSS, 500 ml 1.1 gm NaHCO$_3$; | EDTA Stock. 10 ml 184.2 mg EDTA sodium salt |

TABLE VII-continued

DISSOCIATED CULTURE PROTOCOL

| | |
|---|---|
| 50 ml EBSS stock (Gibco 14050-025); 450 ml dH$_2$O; sterile filter. 10 and 10 Stock, 10 ml 100 mg BSA (Sigma A-4919); 100 mg Trypsin Inhibitor from Egg White (Sigma T-2011) 10 ml dissoc. EBSS; sterile filter. Media Dissociated growth, 500 ml 500 ml MEM (Gibco 51200-020) containing glucose and NaHCO$_3$ (2.25 gm glucose and 0.5 gm NaHCO$_3$); 25 ml heat-inactivated Equine Serum (HyClone A-3311-L); 5 ml L-Glutamine (200 mM, 100x stock, Gibco 25030-081); sterile filter. 15 ml heat-inactivated Equine Serum (HyClone A-3311-L); 3 ml L-Glutamine (200 mM, 100x stock, Gibco 25030-081); (Gibco 15140-015); 1 ml Penicillin-Streptomycin stock. For papain dissociation: 4 mg Cysteine (C-8277); 25 ml dissoc. EBSS; 250 µl Papain stock (Worthington LS003126); place in 37° C. waterbath until clear. | (Sigma ED4S); 10 ml dH$_2$O; sterile filter. Poly-D-Lysine Stock, 5 ml 5 mg Poly-D-Lysine, 100–150 K (Sigma P-6407); 5 ml sterile water; keep frozen. Plating media, 300 ml 250 ml MEM containing glucose and sodium bicarbonate (2.25 gm glucose and 0.5 gm NaHCO$_3$ in 500 ml Gibco MEM 51200-020); 30 ml Fetal Bovine Serum (HyClone A-1111-L). For DNAase treatment: DNAase, 5 ml 4.5 ml dissoc. EBSS; 500 µl "10 and 10" stock; 50 µl DNAase stock. "10 and 10", 5 ml 4.5 ml of EBSS; 500 µl "10 and 10" stock. |

II. COAT DISHES
Use poly-d-lysine stock at 1:100 dilution to coat 24-well plates (0.5 ml/well) or at 1:10 dilution to coat 35 mm glass cover slips (1.0 ml/coverslip).
Leave until end of dissection.
III. DISSECT TISSUE
Use Harlan Sprague-Dawley timed pregnancy rats, ordered to arrive at E-17.
Decapitate, spray abdomen down with 70% EtOH.
Remove uterus through midline incision and place in sterile dPBS.
Remove brains from embryos, leaving them in dPBS.
Brain removal: Penetrate skull and skin with fine forceps at lambda. Pull back to open posterior fossa.
Then move forceps anteriorly to separate sagittal suture. Brain can be removed by scooping back from olfactory bulbs under the brain.
Move brains to fresh dPBS; subsequently, dissect away from cortex.
IV. PAPAIN DISSOCIATION
Transfer cortices equally to two 15 ml tubes containing sterile papain solution, maintained at 37° C.
Triturate xl with sterile 10 ml pipette.
Incubate only for 15 minutes at 37° C.
Spin at 500 G for 5 minutes (1000–2000 RPM on swinging bucket Beckman)
V. DNAase TREATMENT
Remove supernatant and any DNA gel layer from cell pellet (or pick up and remove pellet with pipette).
Move cell pellet to DNAase solution.
Triturate with 10 ml pipette, x15–20.

TABLE VII-continued

DISSOCIATED CULTURE PROTOCOL

Layer cell suspension over the "10 and 10" solution by pipetting it against the side of the tubes.
Spin again at 500 G for 5 minutes (cells will spin into "10 and 10" layer).
Wash tube sides with plating media without disturbing pellet.
Pipette off the media wash and repeat the wash.
VI. PLATE
Add about 4.5 ml plating media to each pellet for 5 ml volume.
Re-suspend with 10 ml pipette.
Pool cells into a single tube.
Quickly add 10 µl of the suspended cells to a hemocytometer so that they do not settle.
Count cells per large square, corresponding to 10 million cells/ml.
Put re-suspended cells into a larger container so that they number 2.5 million cells/ml.
Triturate to homogeneity.
Finish coating plates:
Aspirate or dump Lysine;
Wash x1 with sterile water and dump.
Add plating media, with cells, to the plates as follows:

| | |
|---|---|
| 35 mm dishes | 2 ml/dish; |
| 6 well plate | 2 ml/well; |
| 12 well plate | 1 ml/well; |
| 24 well plate | 500 µl/well. |

VII. FEED
Cultures are usually made on Thursdays.
Start feeding twice a week; beginning the following Monday, feedings on Mondays and Fridays.
Remove 50% of volume and replace with fresh growth media.

b. Ischemic Insult Using Potassium Cyanide and 2-deoxyglucose

Twenty-one to twenty-four days following the initial cortical cell plating, the experiment is performed. The cultures are washed three times in HEPES buffered saline solution containing no phosphate. The cultures are then exposed to potassium cyanide (KCN) (5 mM) and 2-deoxyglucose (2-DG) (10 mM) for 20 minutes at 37° C. These concentrations were shown previously to induce maximal toxicity (Vornov et al., *J. Neurochem*, Vol. 65, No. 4, pp. 1681–1691 (1995)). At the end of 24 hours, the cultures are analyzed for release of the cytosolic enzyme lactate dehydrogenase (LDH), a standard measure of cell lysis. LDH measurements are performed according to the method of Koh and Choi, *J. Neuroscience Methods* (1987).

c. NAAG Induced Neurotoxicity

Cultures are assessed microscopically and those with uniform neuronal densities are used in the NAAG neurotoxicity trials.

At the time of the experiment, the cultures are washed once in HEPES-buffered saline solution (HBSS; NaCl 143.4 mM, HEPES 5 mM, KCl 5.4 mM, MgSO$_4$ 1.2 mM, NaH$_2$PO$_4$ 1.2 mM, CaCl$_2$ 2.0 mM, D-glucose 10 mM) (Vornov et al., 1995) and then exposed to various concentrations of NAAG for 20 minutes at 37° C. NAAG concentrations range from 3 µM to 3 mM, and include 3 µM, 10 µM, 30 µM, 100 µM, 300 µM, 1 mM, and 3 mM. At the end of exposure, the cells are washed once with HEPES buffered saline solution and then replaced with serum free modified Earle's basal medium. The cultures are then returned to the CO$_2$ incubator for 24 hour recovery.

d. Lactate Dehydrogenase Assay

Release of the cytosolic enzyme lactate dehydrogenase (LDH), a standard measure of cell lysis, is used to quantify injury (Koh and Choi, 1987). LDH-activity measurements are normalized to control for variability between culture preparations (Koh and Choi, 1987). Each independent experiment contains a control condition in which no NAALADase inhibitors are added; a small amount of LDH activity is found in these controls. This control measurement is subtracted from each experimental point. These values are normalized within each experiment as a percentage of the injury caused by NAAG/ischemia. Only main effects of NAALADase inhibitors are considered; interactions between dose and condition are not examined statistically.

A measurement of the potency of each compound tested is made by measuring the percentage of LDH release into the growth media after exposure to NAAG/ischemia plus NAALADase inhibitor or NAAG/ischemia plus saline (control). Since high concentrations of glutamate may be toxic to cells in certain circumstances, measurement of glutamate toxicity is observed using LDH as a standard measurement technique.

In Vivo Assay of NAALADase Inhibitors on Cortical Injury following MCAO in SHRSP Rats To examine the effect of NAALADase inhibitors on cortical injury in vivo, the infarct volume was measured in SHRSP rats which had sustained middle cerebral artery occlusion (MCAO) and had subsequently been treated with (i) saline; (ii) 10 mg/kg of 2-(phosphonomethyl) pentanedioic acid followed by 2 mg/kg/hr of 2-(phosphonomethyl)pentanedioic acid for 1 hour; or (iii) 100 mg/kg of 2-(phosphonomethyl)pentanedioic acid followed by 20 mg/kg/hr of 2-(phosphonomethyl)pentanedioic acid for one hour.

The cortical injury volume for each group of rats is provided below in TABLE VIII and graphically presented in FIG. 5.

TABLE VIII

| Cortical Injury Volume (mm$^3$) ± S.E.M. | | |
|---|---|---|
| Control | 184.62 ± 33.52 | (n = 10) |
| 10 mg/kg | 135.00 ± 32.18 | (n = 10) |
| 100 mg/kg | 65.23 ± 32.18 | (n = 10) |
| Cortical Injury Volume (% injury) ± S.E.M. | | |
| Control | 34.44 ± 6.53 | (n = 10) |
| 10 mg/kg$^3$ | 29.14 ± 7.68 | (n = 10) |
| 100 mg/kg | 13.98 ± 6.64 | (n = 10) |
| Cortical Protection (% protection) | | |
| Control | 0% | |
| 10 mg/kg | 27% | |
| 100 mg/kg | 65% | |

The results show that cortical injury volume decreased and cortical protection increased as the amount of NAALADase inhibitor increased, further supporting the neuroprotective effect of the NAALADase inhibitor.

Protocol for In Vivo Assay of NAALADase Inhibitors on Cortical Injury

A colony of SHRSP rats is bred at Johns Hopkins School of Medicine from three pairs of male and female rats obtained from the National Institutes of Health (Laboratory, Sciences Section, Veterinary Resources Program, National Center for Research Resources, Bethesda, Md.). All rats are kept in a virus-free environment and maintained on regular diet (NIH 31, Zeigler Bros, Inc.) with water ad libitum. All groups of rats are allowed to eat and drink water until the morning of the experiment.

Transient occlusion of the middle cerebral artery (MCA) is induced by advancing a 4-0 surgical nylon suture into the internal carotid artery (ICA) to block the origin of the MCA (Koizumi, 1986; Longa, 1989; Chen, 1992). The rats are anesthetized with 4% halothane, and maintained with 1.0% to 1.5% halothane in air enriched oxygen using a face mask. Rectal temperature is maintained at 37.0±0.50° C. throughout the surgical procedure using a heating lamp. The right femoral artery is cannulated for measuring blood gases (pH, oxygen tension [PO$_2$], carbon dioxide tension [PCO$_2$]) before and during ischemia, for monitoring blood pressure during the surgery. The right common carotid artery (CCA) is exposed through a midline incision; a self-retraining retractor is positioned between the digastric and mastoid muscles, and the omohyoid muscle is divided. The right external carotid artery (ECA) is dissected and ligated. The occipital artery branch of the ECA is then isolated and coagulated. Next, the right internal carotid artery (ICA) is isolated until the pterygopalatine artery is exposed, and carefully separated from the adjacent vagus nerve. The pterygopalatine artery is ligated with 4-0 silk suture close to its origin.

After the CCA is ligated with 4-0 silk suture, a 4-0 silk suture to prevent bleeding from a puncture site, through which a 2.5 cm length of 4-0 monofilament nylon suture (Ethilon), its tip rounded by heating near a electric cautery, is introduced into the ICA lumen. A 6-0 silk suture is tightened around the intraluminal nylon suture at the bifurcation to prevent bleeding, and the stretched sutures at the CCA and the ICA are released. The nylon suture is then gently advanced as far as 20 mm.

Anesthesia is terminated after 10 minutes of MCA occlusion in both groups, and the rats were awakened 5 minutes thereafter. After 2 hours of ischemia, anesthesia is reanesthetized, and reperfusion is performed by withdrawing the intraluminal nylon suture until the distal tip became visible at the origin of the ICA.

Arterial pH and PaCO$_2$, and partial pressure of oxygen (PaO$_2$) are measured with a self-calibrating Radiometer electrode system (ABL 3; Copenhagen, Denmark). Hemoglobin and arterial oxygen content are measured with a hemoximeter (Radiometer, Model OSM3; Copenhagen, Denmark). Blood glucose is measured with a glucose analyzer (model 2300A, Yellow Springs Instruments, Yellow Springs, Ohio).

Each group is exposed to 2 hours of right MCA occlusion and 22 hours of reperfusion. All variables but the rectal temperature are measured at baseline, at 15 minutes and 45 minutes of right MCA occlusion. The rectal temperature is measured at baseline, at 0 and 15 min of MCA occlusion, and at 0 and 22 hours of reperfusion.

In Vivo Assay of NAALADase Inhibitors on Brain Injury following MCAO in Sprague-Dawley Rats To examine the neuroprotective effect of NAALADase inhibitors on brain injury in vivo, Sprague-Dawley rats were treated with a vehicle or 2-(phosphonomethyl)pentanedioic acid before and after sustaining a 2 hour transient middle cerebral artery occlusion (MCAO). In the control group (n=8), the rats received an IP injection of saline 30 minutes post-occlusion followed by IV saline infusion at a rate of 0.5 ml/hr. In the drug treated groups, the rats received an IP injection of 2-(phosphonomethyl)pentane-dioic acid at a dose of 100 mg/kg at 20 minutes pre-occlusion (n=5), 30 minutes post-occlusion (n=9), 60 minutes post-occlusion (n=7), or 120 minutes post-occlusion (n=4), followed by a 20 mg/kg/hr IV infusion for 4 hours (infusion rate=0.5 ml/hr). There was a 15 minute delay between IP and IV treatments for each rat. Twenty two hours following the reperfusion, the rats were euthanized and their brains were removed. Seven coronal sections (2 mm thick) were taken and stained with 1% solution of 2,3,5-triphenyltetraxolium chloride (TTC) for 20 minutes and then fixed in 10% formalin. The anterior and posterior surface of the most rostral brain section and the posterior surface of each of the other 6 sections were imaged. The quantification of infarct size of each brain was obtained using a computer aided-digital imaging analysis system (LOATS). The brain regions completely lacking TTC-staining were characterized as representative of infarcted tissue. The total infarct volume for each rat was calculated by numeric integration of the respective sequential brain areas.

The total infarct volume for each group of rats is graphically presented in FIG. 6.

Vehicle treated rats exhibited a mean total brain infarct volume of 293±26 mm$^3$. Rats treated with 2-(phosphonomethyl)pentanedioic acid either before or after the ischemic insult exhibited significantly lower mean total brain infarct volumes of 122±26 mm$^3$ (p=0.003 vs. vehicle) for 20 minute pre-treatment, 208±40 mm$^3$ (p=0.2 vs. vehicle) for 30 minute post-treatment, 125±57 mm$^3$ (p=0.015 vs. vehicle) for 60 minute post-treatment, and 133±35 mm$^3$ (p=0.005 vs. vehicle) for 120 minute post-treatment. These results indicate that 2-(phosphonomethyl) pentanedioic acid is neuroprotective in rat MCAO model of stroke when administered up to 2 hours post-occlusion.

Protocol for In Vivo Assay of NAALADase Inhibitors on Brain Injury

Male Sprague-Dawley rats (260–320 g) were used. Prior to the experiment, the rats were individually housed and allowed free access to food and water. Each rat received two surgeries: jugular vein cannulation for IV infusion and MCAO. During surgeries, the rat was anesthetized with 2% halothane delivered in oxygen via an inhalation mask. The body temperature was monitored and regulated at normothermic level using a homeothermic heating system. First, a PE-50 polyethylene catheter was inserted into the right jugular vein. One hour later, the rat was reanesthetized for MCAO surgery. The MCAO was achieved using the endovascular suture method described by Long et al., Stroke, Vol. 20, pp. 84–91 (1989). Specifically, the right external carotid artery (ECA) was exposed, coagulated and transected. A 3-0 monofilament nylon suture with a blunted tip was introduced into the proximal stump of the ECA via an arteriotomy and advanced 20 mm from the carotid bifurcation until it lodged in the proximal region of the anterior cerebral artery, thereby occluding the origin of the MCA. The rats were allowed to wake up; 2 hours later, the rats were reanesthetized for reperfusion, during which the nylon suture was retracted to the stump of the ECA allowing blood recirculation to the MCA.

In Vivo Assay of NAALADase Inhibitors on Stroke-Induced Rise in Brain Glutamate Levels To examine the effect of NAALADase inhibitors on hyperglutamatergic disorders in vivo, rats with stroke-induced rise in brain glutamate levels were treated with a vehicle or 2-(phosphonomethyl)pentanedioic acid.

The results are graphically presented in FIGS. 7, 8 and 9.

The results show that 2-(phosphonomethyl)pentanedioic acid treatment (100 mg/kg IP followed by 20 mg/kg/hr IV) significantly attenuated stroke-induced extracellular glutamate increases in the striatum (FIG. 7) as compared to vehicle treated rats (p<0.05), and completely prevented concurrent glutamate changes in the parietal cortex (p<0.01; FIG. 8). In contrast, there was no significant effect of the stroke itself on glutamate in the frontal cortex and no subsequent difference between the vehicle and 2-(phosphonomethyl)pentanedioic acid treated groups (FIG. 9). Values are expressed as % baseline where baseline constitutes the mean of three consecutive 20 minute samples preceding stroke. Absolute basal (pretreatment) values for glutamate (mean±SEM) in caudate, parietal and frontal cortices were 0.25+0.1, 1.1+0.3 and 0.6+0.1 $\mu$M, respectively, in the vehicle treated rats, and 0.46+0.1, 2.0+0.7 and 0.9+0.3 $\mu$M, respectively, in the 2-(phosphonomethyl)pentanedioic acid treated rats.

Protocol for In Vivo Assay of NAALADase Inhibitors on Stroke-Induced Rise in Brain Glutamate Levels Male Sprague Dawley rats (270–330 g, n=5–6 per group) were implanted with concentric microdialysis probes similar to previously described procedures (Britton et al., J. Neurochem., Vol. 67, pp. 324–329 (1996)). In brief, under halothane anaesthesia, probes (constructed in-house using Cuprophane capillary membrane; 10K mw cut off; 2 mm dialyzing length) were implanted into the frontal cortex (AP=+3.5; ML=3; DIV=3), caudate nucleus (AP=0; ML=3; DV=6.6), and parietal cortex (AP=−2; ML=5; DV=3) (coordinates in mm relative to bregma and dura, respectively), regions believed to represent core and penumbral areas of ischemia-induced injury. Glutamate levels in dialysate were determined using precolumn o-phthaldialdehyde derivatization, followed by HPLC with fluorometric detection.

Approximately 20 hours after probe implantation, the rats were dialyzed with perfusion fluid (125 mM NaCl, 2.5 mM KCl, 1.18 mM MgCl$_2$ and 1.26 mM CaCl$_2$) at a rate of 2.5 $\mu$l/min. Following a 60 minute stabilization period, dialysis samples were collected every 20 minutes. After collecting 3 baseline samples, the rats were anaesthetized with halothane and subjected to temporary ischemia using the filament method of MCAO (Britton et al., Life Sciences, Vol. 60, No. 20, pp. 1729–1740 (1997)). In brief, the right external carotid artery (ECA) was exposed and its branches coagulated. A 3-0 monofilament nylon suture was introduced into the internal carotid artery via an arteriotomy in the ECA and advanced until it lodged in the proximal region of the anterior cerebral artery, thus occluding the origin of the MCA. The endovascular suture was retracted to allow reperfusion 2 hours after occlusion.

Body temperature was maintained normothermic throughout stroke surgery and reperfusion procedures. The rats were dosed IP with 100 mg/kg 2-(phosphonomethyl) pentanedioic acid at −20 minute preocclusion and IV with 20 mg/kg/hr for 4 hours at the time of occlusion. Dialysis samples were collected every 20 minutes from unanesthetized rats. Following 24 hours of reperfusion, the rats were sacrificed, their brains were removed, and 7 coronal sections (2 mm thick) were taken from the region beginning 1 mm from the frontal pole and ending just rostral to the cortico-cerebellar junction. Analysis of ischemic cerebral damage was achieved using TTC staining and computer assisted image analysis as described by Britton et al. (1997), supra.

In Vivo Assay of NAALADase Inhibitors on Myelin Formation Following Sciatic Nerve Cryolesion It was recently demonstrated that NAALADase is down-regulated in glial cells as they start to form myelin and is absent in myelinating Schwann cells. Based on this data, the inventors hypothesized that inhibition of NAALADase may affect the signaling mechanism between axons and Schwann cells and result in increasing myelination. To test this hypothesis, the inventors examined the effect of 2-(phosphonomethyl)pentanedioic acid on nerve regeneration and myelination following cryolesion of the sciatic nerve in male mice.

The results are provided below in TABLE IX and graphically presented in FIG. 10(a) and FIG. 10(b).

TABLE IX

IN VIVO EFFECT OF NAALADASE INHIBITORS ON MYELIN FORMATION FOLLOWING SCIATIC NERVE CRYOLESION

|  | 2-(phosphonomethyl)-pentanedioic acid | vehicle |
| --- | --- | --- |
| ratio of # of myelinated axons (drug/vehicle) | 1.5 |  |
| # of myelinated lamellae (ave. + SEM) | 16.53 ± 0.65 | 13.77 ± 0.09 |
| % increase of myelinated lamellae over vehicle | 20% |  |
| significance by t-test | p < 0.005 |  |

Figure 10A:
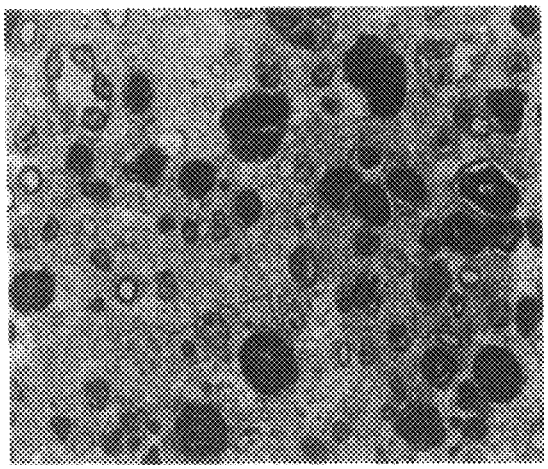
FIG. 10(a) is a photomicrograph of mouse sciatic nerve treated with a vehicle following cryolesion.
Figure 10B:
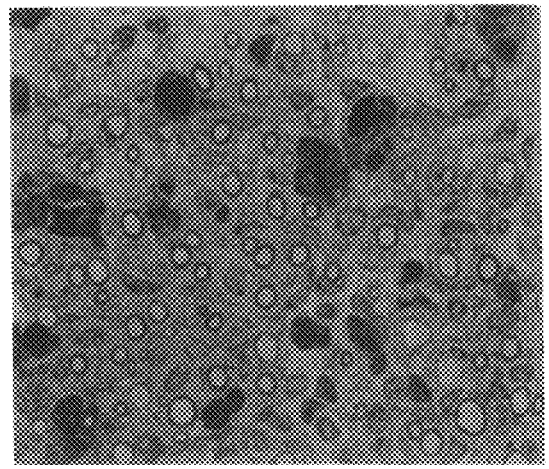
FIG. 10(b) is a photomicrograph of mouse sciatic nerve treated with 2-(phosphonomethyl)pentanedioic acid following cryolesion.

As detailed in FIG. 10(a) and FIG. 10(b), both light and transmission electron microscopy (TEM) examination of the nerve 3 mm distal to the site of cryolesion demonstrated a significant increase in the number of myelinated axons (1.5-fold increase) and myelin thickness (20% increase, p<0.005), as compared to nerves in mice treated with vehicle.

FIG. 10(a) and FIG. 10(b) show a photomicrograph of this effect. Sections were stained with toluidine blue which stains myelin. Sciatic nerves treated with 2-(phosphonomethyl)-pentanedioic acid containing implants, compared with sciatic nerves treated with vehicle containing implants, exhibited an increase in myelinated axon number as well as an increase in myelin thickness.

Protocol for In Vivo Assay of NAALADase Inhibitors on Myelin Formation Following Sciatic Nerve Cryolesion Cryolesion of the mouse sciatic nerve was performed according to Koenig et al., Science, Vol. 268, pp. 1500–1503 (June 1995). In brief, each mouse was anesthetized and its sciatic nerve was exposed in the upper thigh and cryolesioned using a copper cryode (diameter=0.5 mm) that was dipped in liquid nitrogen and repeatedly applied to the upper part of the nerve. The extent of the lesion was approximately 1 mm.

2-(Phosphonomethyl)pentanedioic acid was incorporated into silicone strips according to the method of Connold et al., Developmental Brain Res, Vol. 28, pp. 99–104 (1986), and was implanted at the site of cryolesion on day 0 and replaced on days 3, 6, 9 and 12. Approximately 2.5 µg/day of 2-(phosphonomethyl)pentanedioic acid was released from the silicone implants each day. Both right and left sciatic nerves of each mouse were lesioned; right-side nerves were treated with silicone implant strips containing vehicle alone while left-side nerves were treated with silicone implants containing 2-(phosphonomethyl)pentanedioic acid. Fifteen days after surgery, the mice were sacrificed and their sciatic nerve segments were collected and processed for light microscopy and TEM analysis. Randomly chosen fields 2–3 mm distal to the lesion were qualitatively analyzed by light microscopy using 1-micrometer-thick toluidine blue stained cross sections and photographic images were captured.

In Vivo Assay of NAALADase Inhibitors on Parkinson's Disease

To examine the effect of NAALADase inhibitors on Parkinson's Disease in vivo, MPTP lesioned mice were treated with 2-(phosphonomethyl)pentanedioic acid or a vehicle.

The percent of dopaminergic neurons for each group of mice is provided below in TABLE X and graphically presented in FIG. 11.

TABLE X

IN VIVO EFFECT OF NAALADASE INHIBITORS ON PARKINSON'S DISEASE

|  | Percent Strial TH Innervation Density (mean ± SEM) |
| --- | --- |
| vehicle/vehicle | 24.74 ± 1.03 |
| MPTP/vehicle | 7.82 ± 0.68 |
| MPTP/2-(phosphonomethyl)-pentanedioic acid | 16.28 ± 0.98 |

Mice treated with MPTP and vehicle exhibited a substantial loss of functional dopaminergic terminals as compared to non-lesioned mice (approximately 68% loss). Lesioned mice receiving 2-(phosphonomethyl)pentanedioic acid (10 mg/kg) showed a significant recovery of TH-stained dopaminergic neurons (p<0.001). These results indicate that 2-(phosphonomethyl)pentanedioic acid protects against MPTP-toxicity in mice.

Protocol for In Vivo Assay of NAALADase Inhibitors on Parkinson's Disease

MPTP lesioning of dopaminergic neurons in mice was used as an animal model of Parkinson's Disease, as described by Steiner, Proc. Natl. Acad. Sci., Vol. 94, pp. 2019–2024 (March 1997). In brief, four week old male CD1 white mice were dosed IP with 30 mg/kg of MPTP for 5 days. 2-(Phosphonomethyl)pentanedioic acid (10 mg/kg) or a vehicle was administered SC along with the MPTP for 5 days, as well as for an additional 5 days following cessation of MPTP treatment. At 18 days following MPTP treatment, the mice were sacrificed and their brains were removed and sectioned. Immunostaining was performed on saggital and coronal brain sections using anti-tyrosine hydroxylase (TH) antibodies to quantitate survival and recovery of dopaminergic neurons.

In Vivo Assay of NAALADase Inhibitors on Dynorphin-Induced Spinal Cord Injury

To examine the neuroprotective effect of NAALADase inhibitors on excitotoxic spinal cord injury in vivo, rats which had sustained dynorphin-induced spinal cord injury were treated with a vehicle or 2-(phosphonomethyl)pentanedioic acid.

The results are graphically presented in FIG. 12.

When co-administered with dynorphin A, 2-(phosphonomethyl)pentanedioic acid (4 µmoles) caused significant improvement in motor scores by 24-hour post-injection, as compared to vehicle treated rats (p<0.05, Kruskal-Wallis comparison). The rats were characterized as ambulatory or not on the basis of their assigned neurological scores (0 to 4). At 24 hours post-injection, 73% of the 15 rats co-treated with 2-(phosphonomethyl)pentanedioic acid were ambulatory, in contrast to 14% of the 14 vehicle co-treated rats (p<0.05). These results indicate that 2-(phosphonomethyl)pentanedioic acid provides effective protection against dynorphin-induced spinal cord injury.

Protocol for In Vivo Assay of NAALADase Inhibitors on Dynorphin-Induced Spinal Cord Injury Spinal Subarachnoid Injections Dynorphin-induced spinal cord injury was performed according to Long et al., *JPET*, Vol. 269, No. 1, pp. 358–366 (1993). In brief, spinal subarachnoid injections were delivered using 30-gauge needles inserted between the L4–L5 vertebrae of male Sprague-Dawley rats (300–350 g). The rats were anesthetized with halothane and dorsal midline incisions were made immediately rostral to the pelvic girdle. By using the vertebral processes as guides, the needle was advanced to pass into the subarachnoid space surrounding the cauda equina. Correct needle placement was verified by CSF flow from the needle after its insertion. Injections were delivered using a Hamilton microsyringe in a total volume of 20 $\mu$l which contained dynorphin (20 nmol), the cannula flush and 2-(phosphonomethyl)pentanedioic acid or vehicle. After injections, the incisions were treated with the topical antibacterial furazolidone and closed with wound clips. Rapid recovery from the halothane anesthesia enabled neurological evaluations to be made within 5 minutes of injections.

Neurological Evaluations

Neurological function was evaluated using a 5-point ordinal scale, with scores being assigned as follows: 4=normal motor function; 3=mild paraparesis, with the ability to support weight and walk with impairment; 2=paraparesis, with the ability to make walking movements without fully supporting weight; 1=severe paraparesis, in which rats could make limited hind limb movement, but not walking movement; and 0=flaccid paralysis, with complete absence of any hind limb movement. Neurological evaluations were made 24 hours after dynorphin A injection.

Statistics

Differences in the neurological scores among treatment groups were determined by means of the Mann-Whitney U test or the Kruskal-Wallis test.

In Vitro Assay of NAALADase Inhibitors on Amyotrophic Lateral Sclerosis (ALS)

To examine the neuroprotective effect of NAALADase inhibitors on Amyotrophic Lateral Sclerosis (ALS), spinal cord organotypic cultures were treated with threohydroxyaspartate (THA), 2-(phosphonomethyl)pentanedioic acid, or THA combined with 2-(phosphonomethyl)pentanedioic acid, and assayed for choline acetyltransferase (ChAT) activity.

The ChAT activity for each treatment of the spinal cord organotypic cultures is provided below in TABLE XI and graphically presented in FIG. 13.

TABLE XI

NEUROPROTECTIVE EFFECT OF NAALADASE INHIBITORS IN SPINAL CORD CULTURE MODEL OF ALS

| Treatment | ChAT Activity (% of Control) |
| --- | --- |
| control | 100 ± 22.1 |
| 2-(phosphonomethyl)-pentanedioic acid alone | 108 ± 18.4 |
| THA alone | 36 ± 12.1 |
| 2-(phosphonomethyl)-pentanedioic acid and THA | 121 ± 18.8 |

As shown in FIG. 13, treatment of the spinal cord organotypic cultures with 100 $\mu$M THA resulted in a reduction of ChAT activity to approximately 36% of control cultures. Co-incubation of the cultures with THA and 2-(phosphonomethyl)pentanedioic acid (100 nM–10 $\mu$M) significantly protected the cultures from THA toxicity.

The dose-response of this effect is provided below in TABLE XII and graphically presented in FIG. 14.

TABLE XII

NEUROPROTECTIVE EFFECT OF NAALADASE INHIBITORS IN SPINAL CORD CULTURE MODEL OF ALS

| | ChAT Activity (% of Control) |
| --- | --- |
| control | 100.0 |
| THA | 0 |
| THA and 1 nM 2-(phosphonomethyl)-pentanedioic acid | −23.9 ± 18.6 |
| THA and 10 nM 2-(phosphonomethyl)-pentanedioic acid | 23.1 ± 12.5 |
| THA and 100 nM 2-(phosphonomethyl)-pentanedioic acid | 87.5 ± 21.7 |
| THA and 1 $\mu$M 2-(phosphonomethyl)-pentanedioic acid | 187.7 ± 32.8 |
| THA and 10 $\mu$M 2-(phosphonomethyl)-pentanedioic acid | 128.7 ± 17.2 |

Spinal cord cultures were incubated with various doses of 2-(phosphonomethyl)pentanedioic acid (1 nM to 10 $\mu$M) in the presence of THA (100 $\mu$M) for 14 days. As shown in FIG. 14, 2-(phosphonomethyl)pentanedioic acid exhibited dose-dependent protection against THA-induced toxicity with maximal effects at 1 $\mu$M.

Protocol for In Vivo Assay of NAALADase Inhibitors on Amyotrophic Lateral Sclerosis (ALS)

Spinal Cord Organotypic Cultures

Organotypic cultures were prepared from lumbar spinal cord of 8 day old rats, as described by Rothstein et al., *J. Neurochem.*, Vol. 65, No. 2 (1995), and Rothstein et al., *Proc. Natl. Acad. Sci. USA*, Vol. 90, pp. 6591–6595 (July 1993). In brief, lumbar spinal cords were removed and sliced into 300 $\mu$M-thick-dorsal-ventral sections, and five slices were placed on Millipore CM semipermeable 30-mm-diameter membrane inserts. The inserts were placed on 1 ml of culture medium in 35-mm-diameter culture wells. Culture medium consisted of 50% minimal essential medium and phosphate-free HEPES (25 mM), 25% heat-inactivated horse serum, and 25% Hanks' balanced salt solution (GIBCO) supplemented with D-glucose (25.6 mg/ml) and glutamine (2 mM), at a final pH of 7.2. Antibiotic and antifungal agents were not used. Cultures were incubated at 37° C. in 5% $CO_2$ containing humidified environment (Forma Scientific). Culture medium, along with any added pharmacological agents, was changed twice weekly.

Chronic Toxicity Model with THA

For all experiments, cultures were used 8 days after preparation at which time threohydroxyaspartate (THA; 100 $\mu$M), 2-(phosphonomethyl)pentanedioic acid (100 pM–10 $\mu$M), or THA (100 $\mu$M) ±2-(phosphonomethyl)pentanedioic acid (100 pM–10 $\mu$M) were added to the culture medium. Drugs were incubated for an additional 13 to 20 days with the 100 $\mu$M THA. At the end of this period, cultures were collected assayed for ChAT activity as described below.

ChAT Assays

To determine choline acetyltransferase (ChAT) activity, the spinal cord tissues in each dish (five slices) were pooled and frozen (−75° C.) until assay. ChAT activity was measured radiometrically by described methods using [$^3$H] acetyl-CoA (Amersham; Fonnum, 1975). Protein content of tissue homogenate was determined by a Coomassi Protein Assay kit (Pierce, Rockford, Ill.).

EXAMPLES

The following examples are illustrative of the present invention and are not intended to be limitations thereon. Unless otherwise indicated, all percentages are based upon 100% by weight of the final composition.

EXAMPLE 1

Preparation of 2-[(methylhydroxyphosphinyl) methyl]pentanedioic acid

Scheme IV: R=$CH_3$, $R_1$=$CH_2Ph$

Methyl-O-benzylphosphinic acid

Dichloromethylphosphite (10.0 g, 77 mmol) in 80 mL of dry diethyl ether was cooled to −20° C. under an atmosphere of nitrogen. A solution of benzyl alcohol (23 g, 213 mmol) and triethylamine (10.2 g, 100 mmol) in 40 mL of diethyl ether was added dropwise over 1 hour while maintaining an internal temperature range of 0° C. to 10° C. Once addition was complete the mixture was warmed to room temperature and stirred overnight. The mixture was filtered and the solid cake washed with 200 mL of diethyl ether. The organics were combined and evaporated under reduced pressure to give 25 g of a clear and colorless liquid. The liquid was purified by flash chromatography and eluted with a 1:1 hexane/ethyl acetate to ethyl acetate gradient. The desired fractions were collected and evaporated to give methyl-o-benzylphosphinic acid (1, R=$CH_3$, $R_1$=$CH_2Ph$, 6.5 g, 50%) as a clear and colorless oil. R$f$0.1 (1:1, Hexane/EtOAc).

$^1$H NMR (d6-DMSO): 7.4 ppm (m, 5H), 7.1 ppm (d, 1H), 5.0 ppm (dd, 2H), 1.5 ppm (d, 3H).

2,4-Di(benzyloxycarbonyl)butyl(methyl)-O-benzylphosphinic acid

Methyl-O-benzylphosphinic acid (3.53 g, 20.7 mmol) in 200 mL of dichloromethane was cooled to −5° C. under an atmosphere of nitrogen. Triethylamine (3.2 g, 32 mmol) was added via syringe followed by trimethylsilyl chloride (2.9 g, 27 mmol). The reaction mixture was stirred and warmed to room temperature over 1 hour. Dibenzyl 2-methylenepentanedioate (2, 6.0 g, 18.5 mmol) in 10 mL of dichloromethane was added. The mixture was then stirred at room temperature overnight. The reaction mixture was cooled to 0° C. and trimethylaluminum (9 mL, 18 mmol, 2.0 M in dichloromethane) was added. The flask was warmed and stirred for 72 hours. The clear light yellow solution was cooled to 5° C. and quenched by the slow addition of 5% hydrochloric acid. The quenched reaction mixture was warmed to room temperature and the organic layer removed. The organic layer was washed with 5% hydrochloric acid and with water. The organics were dried ($MgSO_4$) and evaporated under reduced pressure to give 8 g of a clear light yellow oil. The oil was purified on silica gel and eluted with a gradient of 1:1 hexanes/ethyl acetate to 100% ethyl acetate. The desired fractions were collected and evaporated to give 2,4-di(benzyloxycarbonyl)butyl(methyl)-O-benzylphosphinic acid (3, R=$CH_3$, $R_1$=$CH_2Ph$, 0.8 g, 8%) as a clear and colorless oil. R$f$0.5 (ethyl acetate).

$^1$H NMR (CDCl$_3$): 7.4 ppm (m, 15H), 5.1 ppm (m, 6H), 3.0 ppm (m, 1H), 2.4 ppm (m, 3H), 2.1 ppm (m, 3H), 1.5 ppm (dd, 3H). Elemental Analysis; Calculated $C_{28}H_{31}O_6P$, 0.5 $H_2O$: C, 68.01; H, 6.32. Found: C, 66.85; H, 6.35.

2-[(Methylhydroxyphosphinyl)methyl]pentanedioic acid 2,4-di(benzyloxycarbonyl)butyl(methyl)-O-benzylphosphinic acid (0.8 g, 1.6 mmol) in 20 mL of water containing 100 mg of 10% Pd/C was hydrogenated at 40 psi for 4 hours. The mixture was filtered over a pad of Celite and evaporated at high vacuum to give 2-[(methylhydroxyphosphinyl)methyl]pentanedioic acid (4, R=$CH_3$, 0.28 g), 78% as a clear and colorless viscous oil.

$^1$H NMR (D$_2$O): 2.5 ppm (m, 1H), 2.2 ppm (t, 2H), 2.0 ppm (m, 1H), 1.7 ppm (m, 3H), 1.3 ppm (d, 3H). Elemental Analysis; Calculated $C_7H_{13}O_6P$, 0.2 $H_2O$: C, 36.92; H, 5.93. Found: C, 37.06; H, 6.31.

EXAMPLE 2

Preparation of 2-[(butylhydroxyphosphinyl)methyl] pentanedioic acid

Scheme IV: R=n-butyl, $R_1$=H

Butylphosphinic Acid

Diethyl chlorophosphite (25 g, 0.16 mol) in 60 mL of dry ether was cooled to 0° C. under an atmosphere of nitrogen. Butylmagnesium chloride (80 mL, 0.16 mol, 2.0 M solution in ether) was added dropwise over a period of 2 hours while maintaining the internal temperature at 0° C. Once addition was complete the thick white slurry was heated to 30° C. for 1 hour. The suspension was filtered under a nitrogen atmosphere and the filtrate evaporated under reduced pressure. The clear light yellow liquid was then brought up in 15 mL of water and stirred at room temperature. Concentrated hydrochloric acid (0.5 mL) was then added and an exothermic reaction was observed. The mixture was stirred an additional 15 minutes and extracted with two 75 mL portions of ethyl acetate. The organics were combined, dried ($MgSO_4$) and evaporated to give a clear and colorless liquid. The liquid was treated with NaOH (40 mL, 2.0 M) and stirred for 1 hour. The mixture was then washed with diethyl ether and acidified to pH 1.0. The desired material was extracted from the acidified extract with two 100 mL portions of ethyl acetate. The organics were combined, dried ($MgSO_4$) and evaporated under reduced pressure to give butylphosphinic acid (1, R=n-butyl, $R_1$=H, 10 g, 51%) as a clear and colorless liquid.

$^1$H NMR (d6-DMSO): 6.9 ppm (d, 1H), 1.6 ppm (m, 2H), 1.4 ppm (m, 4H), 0.9 ppm (t, 3H).

Butyl[2,4-di(benzyloxycarbonyl)butyl]phosphinic acid

Butylphosphinic acid (2.0 g, 16 mmol) in 80 mL of dry dichloromethane was cooled to 0° C. under an atmosphere of nitrogen. Triethylamine (6.7 g, 66 mmol) was added followed by trimethylsilyl chloride (58 mL, 58 mmol, 1.0 M in dichloromethane). The mixture was stirred at 0° C. for 10 minutes and dibenzyl 2-methylenepentanedioate (2) (6.4 g, 20 mmol) in 20 mL of dichloromethane was added. The cold bath was removed and the reaction warmed to room temperature and stirred overnight. The mixture was then cooled to 0° C. and quenched by the slow addition of 5% hydrochloric acid (50 mL). The dichloromethane layer was then removed and washed with 5% hydrochloric acid and with brine. The organic layer was dried (MgSO$_4$) and evaporated to give a clear light golden liquid. The liquid was purified by flash chromatography and eluted with 3:1 hexane/ethyl acetate containing 5% acetic acid. The desired fractions were combined and evaporated to give butyl[2,4-di(benzyloxycarbonyl)butyl]phosphinic acid (3, R=n-butyl, R$_1$=H) (2.9 g, 40%) as a clear and colorless oil. R$f$0.12 (3:1 Hexane/EtOAc, 5% AcOH).

$^1$H NMR (d6-DMSO): 7.3 ppm (m, 10H), 5.0 ppm (s, 4H), 2.7 ppm (m, 1H), 2.3 ppm (t, 2H), 1.8 ppm (m, 2H), 1.3 ppm (m, 4H), 0.8 ppm (t, 3H).

2-[(Butylhydroxyphosphinyl)methyl]pentanedioic acid

Butyl[2,4-di(benzyloxycarbonyl)butyl]phosphinic acid (2.9 g, 6.5 mmol) in 30 mL of water containing 0.32 g 10% Pd/C was hydrogenated at 40 psi for 4.5 hours. The mixture was filtered through a pad of Celite and evaporated under high vacuum to give 2-[(butylhydroxyphosphinyl)methyl]-pentanedioic acid (4, R=n-butyl) (0.75 g, 43%) as a clear and colorless viscous oil.

$^1$H NMR (D$_2$O): 2.4 ppm (m, 1H), 2.1 ppm (t, 2H), 1.9 ppm (m, 1H), 1.6 ppm (m, 3H), 1.4 ppm (m, 2H), 1.1 ppm (m, 4H), 0.6 ppm (t, 3H). Elemental Analysis; Calculated C$_{10}$H$_{19}$O$_6$P, 0.5 H$_2$O: C, 43.64; H, 7.32. Found: C, 43.25; H, 7.12.

EXAMPLE 3

Preparation of 2-[(benzylhydroxyphosphinyl)methyl]pentanedioic acid

Scheme IV: R=CH$_2$Ph, R$_1$=H
Benzylphosphinic acid

Diethylchlorophosphite (25 g, 0.16 mol) in 100 mL of dry diethyl ether was cooled to 0° C. under an atmosphere of nitrogen. Benzylmagnesium chloride (80 mL, 0.16 mol, 2.0 M solution in Et$_2$O) was added dropwise over two hours while maintaining a temperature below 10° C. A thick white slurry formed and stirring was continued at room temperature for 1 hour. The mixture was filtered under a nitrogen atmosphere and the filtrate evaporated under reduced pressure to give a clear and colorless liquid. The liquid was stirred as 15 mL of water was added followed by 0.5 ml concentrated hydrochloric acid. An exothermic reaction was observed and stirring was continued for an additional 30 minutes followed by extraction with ethyl acetate. The organics were combined, washed with brine, dried (MgSO$_4$) and evaporated. The clear light golden liquid was added to sodium hydroxide (50 mL, 2.0 M NaOH), stirred for 1 hour and washed with diethyl ether. The aqueous layer was acidified to pH 1.0 with concentrated hydrochloric acid and extracted with ethyl acetate. The organics were combined, dried (MgSO$_4$) and evaporated to give benzylphosphinic acid (1, R=CH$_2$Ph, R$_1$=H) (8 g, 32%) as a clear light golden oil.

$^1$H NMR (d6-DMSO): 7.3 ppm (m, 5H), 6.9 ppm (d, 1H), 3.1 ppm (d, 2H).

Benzyl[2,4-di(benzyloxycarbonyl)butyl]phosphinic acid

Benzylphosphinic acid (2.3 g, 15 mmol) in 150 mL of dry dichloromethane was cooled to 0° C. under a nitrogen atmosphere. Triethylamine (6.5 g, 65 mmol) was added followed by trimethylsilyl chloride (5.8 g, 54 mmol) while the reaction temperature was maintained at 0° C. After 30 minutes dibenzyl 2-methylene-pentanedioate (2) (4.4 g, 13.6 mmol) in 20 mL of dichloromethane was added over 5 minutes. The reaction mixture was allowed to warm to room temperature and stirred overnight. The clear solution was cooled to 0° C. and quenched with 5% hydrochloric acid followed by removal of the organic layer. The organic layer was washed with 5% hydrochloric acid and with brine, dried (MgSO$_4$) and evaporated to give a clear yellow liquid. Purification by flash chromatography and elution with 1:1 hexane/ethyl acetate containing 10% acetic acid yielded 2.0 g (28%) of benzyl[2,4-di(benzyloxycarbonyl)butyl]-phosphinic acid (3, R=CH$_2$Ph, R$_1$=H) as a clear light yellow oil. R$f$ 0.37 (1:1 Hexane/EtOAc, 10% AcOH).

$^1$H NMR (d6-DMSO): 7.2 ppm (m, 15H), 5.0 ppm (s, 4H), 3.0 (d, 2H), 2.8 ppm (m, 1H), 2.3 ppm (t, 2H), 1.9 ppm (m, 2H), 1.7 ppm (t, 1H).

2-[(Benzylhydroxyphosphinyl)methyl]pentanedioic acid

Benzyl[2,4-di(benzyloxycarbonyl)butyl]phosphinic acid (0.5 g, 1.0 mmol) in 20 mL of water containing 120 mg of 10% Pd/C was hydrogenated at 40 psi for 6 hours. Filtration through a Celite pad followed by evaporation on high vacuum gave 0.17 g (57%) of 2-[(benzylhydroxyphosphinyl)methyl]-pentanedioic acid (4, R=CH$_2$Ph) as a white solid.

$^1$H NMR (D$_2$O): 7.1 ppm (m, 5H), 2.9 ppm (d, 2H), 2.4 ppm (m, 1H), 2.1 ppm (t, 2H), 1.8 ppm (m, 1H), 1.6 ppm (m, 3H). Elemental Analysis; Calculated C$_{13}$H$_{17}$O$_6$P: C, 52.00; H, 5.71. Found: C, 51.48; H, 5.70.

EXAMPLE 4

Preparation of 2-[phenylethylhydroxyphosphinyl)methyl]pentanedioic acid

Scheme IV: R=CH$_2$CH$_2$Ph, R$_1$=H
Phenethylphosphinic acid

Diethylchlorophosphite (15.6 g, 0.1 mol) in 100 mL of dry diethyl ether was cooled to 5° C. under an atmosphere of nitrogen. Phenethylmagnesium chloride (100 mL, 0.1 mol, 1.0 M in THF) was added dropwise over 2 hours while maintaining a temperature between 0–10° C. A thick white slurry formed and stirred at room temperature overnight. The mixture was filtered under a nitrogen atmosphere and the filtrate evaporated under reduced pressure to give a clear and colorless liquid. The liquid was stirred as 15 mL of water was added followed by 0.5 mL of concentrated hydrochloric acid. An exothermic reaction was observed and stirring continued for 15 minutes followed by extraction with ethyl acetate. The organics were combined, washed with brine, dried (MgSO$_4$) and evaporated. The clear liquid was brought up in sodium hydroxide (40 mL, 2.0 M NaOH), stirred for 1 hour and washed once with diethyl ether. The aqueous layer was acidified to pH 1.0 with concentrated hydrochloric acid and extracted with ethyl acetate. The organics were combined, dried (MgSO$_4$) and evaporated to give phenethylphosphinic acid (1, R=CH$_2$CH$_2$Ph, R$_1$=H) (9.8 g, 58%) as a clear light yellow oil. $^1$H NMR (d6-DMSO): 7.2 ppm (m, 5H), 6.9 ppm (d, 1H), 2.8 ppm (m, 2H), 1.9 ppm (m, 2H).

2,4-Di(benzyloxycarbonyl)butyl(phenethyl) phosphinicacid

Phenethylphosphinic acid (1.0 g, 5.9 mmol) in 50 mL of dry dichloromethane was cooled to −5° C. under a nitrogen atmosphere. Triethylamine (2.3 g, 23 mmol) was added followed by trimethylsilyl chloride (2.2 g, 21 mmol) while the reaction temperature was maintained at 0° C. After 10 minutes dibenzyl 2-methylenepentane-dioate (2) (1.7 g, 5.2 mmol) in 10 mL of dichloromethane was added over 10 minutes. The reaction mixture was left to warm to room temperature and stirred overnight. The clear solution was cooled to 0° C. and quenched with 5% hydrochloric acid followed by removal of the organic layer. The organic layer was washed with brine, dried (MgSO4) and evaporated to give a clear light golden liquid. Purification by flash chromatography and elution with 1:1 Hexane/EtOAc containing 5% AcOH yielded 1.2 g (41%) of 2,4-di(benzyloxycarbonyl)butyl(phenethyl)phosphinic acid (3, R=CH$_2$CH$_2$Ph, R$_1$=H) as a clear and colorless oil.

$^1$H NMR (d6-DMSO): 7.2 ppm (m, 15H), 5.0 ppm (s, 4H), 3.3 ppm (m, 1H), 2.8 ppm (m, 4H), 2.3 ppm (m, 2H), 1.8 ppm (m, 4H).

2-[(Phenethylhydroxyphosphinyl)methyl] pentanedioic acid 2,4-Di(benzyloxycarbonyl)butyl(phenethyl)-phosphinic acid (1.1 g, 2.2 mmol) in 20 mL of water containing 120 mg of 10% Pd/C was hydrogenated at 40 psi overnight. Filtration through a Celite pad followed by evaporation on high vacuum gave 0.8 g (114%) of 2-[(phenethylhydroxyphosphinyl)methyl]pentanedioic acid (4, R=CH$_2$CH$_2$Ph) as a white solid.

$^1$H NMR (D$_2$O): 7.2 ppm (m,5H), 2.7 ppm (m,2H), 2.5 ppm (m,1H), 2.3 ppm (t,2H), 1.9 ppm (m,6H), 1.5 ppm (t,1H) Elemental Analysis; Calculated C$_{14}$H$_{19}$O$_6$P, 0.75H$_2$O, 0.5 AcOH: C, 50.35; H, 6.34. Found: C, 50.26; H, 5.78.

EXAMPLE 5

Preparation of 2-[(3-phenylpropylhydroxyphosphinl)methyl]pentanedioic acid

Scheme IV: R=CH$_2$CH$_2$CH$_2$Ph, R$_1$=H
3-Phenylpropylphosphinic acid

To magnesium turnings (2.44 g, 0.10 mol) in 20 mL of dry diethyl ether under an atmosphere of nitrogen was added several iodine crystals. Phenylpropyl bromide (20.0 g, 0.10 mol) in 80 mL of diethyl ether was placed in a dropping funnel. Approximately 10 mL of the bromide solution was added to the magnesium turnings and stirring was initiated. After several minutes the iodine was consumed and additional phenylpropyl bromide was added while maintaining a temperature of 35° C. Once addition was complete (1.5 hours) the mixture was sealed and stored at 5° C.

Diethylchlorophosphite (15.7 g, 0.1 mol) in 50 mL of dry diethyl ether was cooled to 5° C. under an atmosphere of nitrogen. Phenethylmagnesium bromide (100 mL, 0.1 mol, 1.0 M solution of in Et$_2$O) was added dropwise over 2 hours while maintaining a temperature between 0–10° C. A thick white slurry formed and was stirred for an additional 30 minutes. The mixture was filtered under a nitrogen atmosphere and the filtrate evaporated under reduced pressure to give a clear and colorless liquid. To the liquid was added 20 mL of water followed by 0.5 ml of concentrated hydrochloric acid. An exothermic reaction was observed and stirring continued for 20 minutes followed by extraction with ethyl acetate. The organics were combined, washed with brine, dried (MgSO$_4$) and evaporated. To the clear liquid was added sodium hydroxide (40 mL, 2.0 M NaOH), the resulting solution stirred for 1 hour and then washed with diethyl ether. The aqueous layer was acidified to pH 1.0 with concentrated hydrochloric acid and extracted twice with ethyl acetate. The organics were combined, dried (MgSO$_4$) and evaporated to give 3-phenylpropylphosphinic acid (1, R=CH$_2$CH$_2$CH$_2$Ph, R$_1$=H) (9.8 g, 53%) as a clear and colorless oil.

$^1$H NMR (d6-DMSO): 7.2 ppm (m, 5H), 6.9 ppm (d, 1H), 2.6 ppm (t, 2H), 1.7 ppm (m, 2H), 1.6 ppm (m, 2H).

2,4-Di(benzyloxycarbonyl)butyl(3-phenylpropyl)-phosphinic acid 3-phenylpropylphosphinic acid (1.0 g, 5.4 mmol) in 50 mL of dry dichloromethane was cooled to −5° C. under a nitrogen atmosphere. Triethylamine (2.2 g, 22 mmol) was added followed by trimethylsilyl chloride (2.1 g, 19 mmol) while the reaction temperature was maintained at 0° C. After 10 minutes dibenzyl 2-methylenepentanedioate (2) (1.6 g, 4.9 mmol) in 10 mL of dichloromethane was added over 10 minutes. The reaction mixture was warmed to room temperature and stirred overnight. The clear solution was cooled to 0° C. and quenched with 5% hydrochloric acid followed by removal of the organic layer. The organic layer was washed with brine, dried (MgSO$_4$) and evaporated to give a clear yellow liquid. Purification by flash chromatography and elution with 4:1 hexane/ethyl acetate containing 5% acetic acid resulted in 1.5 g (56%) of 2,4-di (benzyloxycarbonyl)-butyl(3-phenylpropyl)phosphinic acid (3, R=CH$_2$CH$_2$CH$_2$Ph, R$_1$=H) as a clear light yellow oil. Rf0.58 (1:1 Hexane/EtOAc, 5% AcOH).

$^1$H NMR (d6-DMSO): 7.2 ppm (m, 15H), 5.0 ppm (s, 4H), 2.7 ppm (m, 1H), 2.5 ppm (m, 5H), 2.2 ppm (m, 2H), 1.8 ppm (m, 3H), 1.6 ppm (m, 2H). Elemental Analysis; Calculated C$_{29}$H$_{33}$O$_6$P, 1.3 H$_2$O: C, 65.48; H 6.75. Found: C, 65.24; H, 6.39.

2-[(3-Phenylpropylhydroxyphosphinyl)methyl] pentanedioic acid 2,4-Di(benzyloxycarbonyl)butyl(3-phenylpropyl) phosphinic acid (15) (1.4 g, 2.8 mmol) in 20 mL of water containing 150 mg of 10% Pd/C was hydrogenated at 40 psi overnight. Filtration through a Celite pad followed by evaporation on high vacuum gave 0.8 g (89%) of 2-[(3-phenylpropylhydroxyphosphinyl)methyl]pentanedioic acid (4, R=CH$_2$CH$_2$CH$_2$Ph) as a light yellow viscous oil.

$^1$H NMR (D$_2$O): 7.4 ppm (m, 5H), 2.7 ppm (m, 3H), 2.4 ppm (t, 3H), 1.8 ppm (m, 7H). Elemental Analysis; Calculated C$_{15}$H$_{21}$O$_6$P, 0.75 H$_2$O, 0.75 AcOH: C, 51.23; H, 6.64. Found: C, 50.85; H, 6.02.

EXAMPLE 6

Preparation of 2-[[(4-methylbenzyl) hydroxyphosphinyl]methyl]pentanedioic acid Scheme V: Compound 5, R=4-methylbenzyl Hexamethyldisilazane (21.1 mL, 100 mmol) was added to vigorously stirred ammonium phosphinate (8.30 g, 100 mmol), and the resulting suspension was stirred at 105° C. for 2 hours. A solution of 4-methylbenzyl bromide (5.0 g, 27.0 mmol) was then added dropwise to the suspension at 0° C. The mixture was stirred at room temperature for 19 hours. The reaction mixture was then diluted with dichloromethane (50 mL) and washed with 1 N HCl (50 mL). The organic layer was separated, dried over $Na_2SO_4$, and concentrated to give 4.72 g of a white solid. This was dissolved in dichloromethane (50 mL) and benzyl alcohol (3.24 g, 30 mmol) was added to the solution. 1,3-Dicyclohexylcarbodiimide (DCC) (6.19 g, 30 mmol) was then added to the solution at 0° C., and the suspension was stirred at room temperature for 14 hours. The solvent was removed under reduced pressure and the residue was suspended in EtOAc. The resulting suspension was filtered and the filtrate was concentrated. The residue was purified by silica gel chromatography (hexanes: EtOAc, 4:1 to 1:1) to give 2.40 g of 4-methylbenzyl-O-benzylphosphinic acid (2, R=4-methylbenzyl) as a white solid (34% yield). R$f$0.42 (EtOAc).

$^1$H NMR (DMSO-d$_6$): δ 2.30 (s, 3H), 3.29 (d, 2H), 5.2 (m, 2H), 7.0 (d, 1H), 7.1–7.2 (m, 4H), 7.3–7.4 (m, 5H).

2,4-Di(benzyloxycarbonyl)-butyl(4-methylbenzyl)-o-benzylphosphinic acid

To a solution of 4-methylbenzyl-O-benzylphosphinic acid (2, R=4-methylbenzyl) (2.16 g, 8.3 mmol) in THF (15 mL) was added sodium hydride (0.10 g, 60% dispersion in oil) followed by dibenzyl 2-methylenepentanedioate (3) (3.24 g) at 0° C., and the mixture was stirred at room temperature for 4 hours. The reaction mixture was then diluted with EtOAc (50 mL) and poured into 1N HCl (50 mL). The organic layer was separated, dried over $Na_2SO_4$, and concentrated. This material was purified by silica gel chromatography (hexanes: EtOAc, 4:1 to 1:1) to give 3.41 g of 2,4-di(benzyloxycarbonyl)-butyl(4-methylbenzyl)-o-benzylphosphinic acid (4, R=4-methylbenzyl) as colorless oil (70% yield). R$f$0.61 (EtOAc).

$^1$H NMR (CDCl$_3$): δ 1.6–1.8 (m, 1H), 1.9–2.0 (m, 2H), 2.1–2.4 (m, 6H), 2.7–2.9 (m, 1H), 3.05 (dd, 2H), 4.8–5.1 (m, 6H), 7.0–7.1 (m, 4H), 7.2–7.4 (m, 15H).

2-[[(4-Methylbenzyl)hydroxyphosphinyl]methyl] pentanedioic acid

To a solution of 2,4-di(benzyloxycarbonyl)butyl(4-methylbenzyl)-o-benzylphosphinic acid (0.70 g, 1.2 mmol) in ethanol (30 mL) was added Pd/C (5%, 0.10 g) and the suspension was shaken under hydrogen (50 psi) for 18 hours. The suspension was then filtered through a pad of Celite and concentrated under reduced pressure. The resulting residue was dissolved in distilled water (5 mL), passed through a column of AG 50W-X8 resin (H$^+$ form), and lyophilized to give 0.21 g of 2-[[(4-methylbenzyl)hydroxyphosphinyl]methyl]-pentanedioicacid (5, R=4-methylbenzyl) as a white solid (55% yield). R$f$ 0.62 (i-PrOH: H$_2$O, 7:3).

$^1$H NMR (D$_2$O): δ 1.7–1.9 (m, 3H), 2.0–2.2 (m, 1H), 2.33 (dt, 7.4 Hz, 2H), 2.55–2.70 (m, 1H), 3.12 (d, 2H), 7.0–7.1 (m, 2H), 7.2–7.3 (m, 2H). Elemental Analysis Calculated $C_{13}H_{17}O_6P$, 0.30 H$_2$O: C, 52.60; H, 6.18. Found: C, 52.60; H, 6.28.

EXAMPLE 7

Preparation of 2-[[(4-Fluorobenzyl) hydroxyphosphinyl]methyl]pentanedioic acid
Scheme V: R=4-fluorobenzyl
Prepared as described in the above example where R=methylbenzyl. R$f$0.64 (i-PrOH:H$_2$O, 7:3).

$^1$H NMR (D$_2$O): δ 1.7–1.9 (m, 3H), 2.0–2.2 (m, 1H), 2.3–2.4 (m, 2H), 2.55–2.70 (m, 1H), 3.12 (d, 2H), 7.0–7.1 (m, 2H), 7.2–7.3 (m, 2H). Elemental Analysis; Calculated $C_{13}H_{16}FO_6P$, 0.25 H$_2$O: C, 48.38; H, 5.15. Found: C, 48.38; H, 5.15.

EXAMPLE 8

Preparation of 2-[[(4-Methoxybenzyl) hydroxyphosphinyl]methyl]pentanedioic acid
Scheme V: R=4-methoxybenzyl
Prepared as described in the above example where R=methylbenzyl. R$f$0.56 (i-PrOH: H$_2$O, 7:3).

$^1$H NMR (D$_2$O): δ 1.8–1.9 (m, 3H), 2.0–2.2 (m, 1H), 2.3–2.4 (m, 2H), 2.55–2.70 (m, 1H), 3.16 (d, 2H), 3.81 (s, 3H), 6.98 (d, 2H), 7.25 (d, 2H). Elemental Analysis; Calculated $C_{14}H_{19}O_7P$, 0.30 H$_2$O: C, 50.09; H, 5.89. Found: C, 49.98; H, 5.80.

EXAMPLE 9

Preparation of 2-[[(2-Fluorobenzyl) hydroxyphosphinyl]methyl]pentanedioic acid
Scheme V: R=2-fluorobenzyl)
Prepared as described in the above example where R=methylbenzyl. R$f$0.67 (i-PrOH: H$_2$O, 7:3).

$^1$H NMR (D$_2$O): δ 1.8–1.9 (m, 3H), 2.0–2.2 (m, 1H), 2.3–2.4 (m, 2H), 2.55–2.70 (m, 1H), 3.28 (d, 2H), 7.1–7.5 (m, 4H). Elemental Analysis; Calculated $C_{13}H_{16}FO_6P$, 0.10 H$_2$O: C, 48.79; H, 5.10. Found: C, 48.84; H, 5.14.

EXAMPLE 10

Preparation of 2-[[(Pentafluorobenzyl) hydroxyphosphinyl]methyl]pentanedioic acid
Scheme V: R=pentafluorobenzyl
Prepared as described in the above example where R=methylbenzyl. R$f$0.69 (i-PrOH: H$_2$O, 7:3).

$^1$H NMR (D$_2$O): δ 1.8–2.0 (m, 3H), 2.1–2.3 (m, 1H), 2.3–2.5 (m, 2H), 2.7–2.9 (m, 1H), 3.29 (d, 2H). Elemental Analysis; Calculated $C_{13}H_{12}F_5O_6P$, 0.45 H$_2$O: C, 39.20; H, 3.26. Found: C, 39.17; H, 3.28.

EXAMPLE 11

Preparation of 2-[(methylhydroxyphosphinyl) methyl]pentanedioic acid
Scheme VI, Compound 9

2,4-Di(benzyloxycarbonyl)butylphosphinic acid (6)

Ammonium phosphinate (10 g, 0.12 mol) was placed in a round bottom flask with stirring under an atmosphere of nitrogen. Hexamethyldisilazane (HMDS, 25.5 mL, 0.12 mol) was added and the mixture heated to 110° C. After two hours the mixture was cooled to 0° C. and dichloromethane (120 ml) was added. After this was complete, dibenzyl-2-methylene pentanedioate (41 g, 0.13 mol) was added dropwise. The mixture was allowed to warm to room temperature and stirred for 16 hours. The mixture was then quenched with 5% HCl (75 ml) and the organic layer removed. The organics were dried (MgSO$_4$) and evaporated under reduced pressure to give 42 g (90%) of a clear and colorless oil.

$^1$H NMR (CDCl$_3$): 7.36 ppm (m, 10H), 7.1 ppm (d, 1H), 5.19 ppm (s, 2H), 5.15 ppm (s, 2H), 2.92 ppm (m, 1H), 2.21 ppm (m, 6H).

2,4-Di(benzyloxycarbonyl)butylbenzylphosphinic acid (7)

To a solution of 2,4-di-(benzyloxycarbonyl)butyl-phosphinic acid (6) (19.3 g, 49.4 mmol) in tetrahydrofuran was added benzyl alcohol (5.3 g, 49.3 mmol) and dimethylamino pyridine (0.5 g). Dicyclohexylcarbodiimide (DCC, 12 g, 58 mmol) was added and a white precipitate formed. After 30 minutes the white suspension was filtered and the filtrate evaporated under reduced pressure. The clear and colorless oil was purified by flash chromatography and eluted with 1:1 Hexane/EtOAc to give 2,4-di(benzyloxycarbonyl)butylbenzylphosphinic acid (7) (11.5 g, 47%) as a clear and colorless oil. R$f$0.16 (1:1 Hexane/EtOAc).

$^1$H NMR (CDCl$_3$): 7.3 ppm (m, 15H), 7.2 ppm (d, 1H), 5.0 ppm (m, 6H), 2.9 ppm (m, 1H), 2.2 ppm (m, 3H), 1.9 ppm (m, 3H).

2,4-Di(benzyloxycarbonyl)butyl[hydroxy(phenyl)methyl]benzylphosphinic acid (8)

2,4-Di(benzyloxycarbonyl)butylbenzylphosphinicacid (7) in 5 mL of dry THF was added dropwise to a stirring cooled (0° C.) mixture of sodium hydride (0.09 g, 2.3 mmol) in 15 mL of THF. After 15 minutes benzaldehyde (0.23 g, 2.2 mmol) was added via syringe while maintaining a temperature of 0° C. After 30 minutes the mixture was quenched with water and extracted with two portions of dichloromethane. The organics were combined and evaporated to give a clear colorless oil. The oil was chromatographed on silica and eluted with a 1:1 Hexane/EtOAc solvent system. The desired fractions were collected and evaporated to give 0.4 g (33%) of 2,4-di(benzyloxycarbonyl)butyl -[hydroxy(phenyl)methyl]benzylphosphinic acid (6) as a clear and colorless oil. R$f$0.18 (1:1 Hexane/EtOAc).

$^1$H NMR (CDCl$_3$): 7.3 ppm (m, 20H), 5.2 ppm (m, 1H), 4.9 ppm (m, 6H), 2.8 ppm (dm, 1H), 2.2 ppm (m, 3H), 1.9 ppm (m, 3H).

2-([Hydroxy(phenyl)methyl]hydroxyphosphinylmethyl)-pentanedioic acid (9)

2,4-Di(benzyloxycarbonyl)butyl[hydroxy(phenyl)methyl]benzylphosphinic acid (6) (0.37 g, 0.6 mmol) in 25 mL of water containing 0.10 g of 10% Pd/C was hydrogenated at 40 psi for 6 hours. The mixture was filtered through a pad of Celite and lyophilized to give 2-([hydroxy(phenyl)methyl]hydroxyphosphinylmethyl)pentanedioic acid (9) (0.14 g, 70%) as a white solid.

$^1$H NMR (D$_2$O): 7.4 ppm (m, 5H), 5.0 ppm (d, 1H), 2.7 ppm (m, 1H), 2.4 ppm (m, 2H), 2.2 ppm (m, 1H), 1.9 ppm (m, 3H). Elemental Analysis: Calculated C$_{13}$H$_{17}$O$_7$P, 0.6 H$_2$O: C, 47.74; H, 5.61. Found: C, 47.73; H, 5.68.

EXAMPLE 12

Preparation of dibenzyl 2-methylenepentanedioate Using Scheme III

Benzyl acrylate (500 g, 3.0 mol) was heated in an oil bath to 100° C. Heating was stopped and HMPT (10 g, 61 mmol) was added dropwise while maintaining an internal temperature below 140° C. Once addition was complete, the mixture was stirred and cooled to room temperature. A slurry of silica (5:1 Hexane/EtOAc) was added and the mixture was placed in a column containing a plug of dry silica. The column was washed with 1:1 Hexane/EtOAc and the fractions were combined and evaporated to give 450 g of clear light golden liquid. The liquid was distilled under high vacuum (200 μHg) at 185° C. to give 212 g (42%) of a clear and colorless liquid.

$^1$H NMR (CDCl$_3$): 7.3 ppm (m, 10H), 6.2 ppm (s, 1H), 5.6 ppm (s, 1H), 5.2 ppm (s, 2H), 5.1 ppm (s, 2H), 2.6 ppm (m, 4H).

EXAMPLE 13

Preparation of dibenzyl 2-[[bis(benzyloxy)phosphoryl]methyl]pentanedioate Using Scheme III Dibenzyl phosphite (9.5 g, 36 mmol) in 350 ml of dichloromethane was cooled to 0° C. To this stirring solution was added trimethyl aluminum (18.2 ml, 2.0 M solution in hexane, 36.4 mmol). After 30 minutes, dibenzyl 2-methylenepentanedioate (2) (6.0 g, 37 mmol) in 90 ml of dichloromethane was added dropwise over 10 minutes. The clear and colorless solution was then warmed to room temperature and left to stir overnight. The mixture was then quenched by the slow addition of 5% HCl. After stirring an additional 1.5 hours the lower organic layer was removed and the aqueous layer extracted once with 100 ml of dichloromethane. The organics were combined, dried (MgSO$_4$), and evaporated to give a clear light golden liquid. The liquid was chromatographed on silica gel (4 cm*30 cm) and eluted with a gradient (4:1-1:1) solvent system (Hexane/EtOAc). The fractions containing the desired product were combined and evaporated to yield dibenzyl 2-[[bis(benzyloxy)phosphoryl]methyl]pentanedioate (7.1 g, 42%) as a clear and colorless liquid. The liquid was then distilled on a Kughleror apparatus at 0.5 mm Hg and 195–200° C. The distillate was discarded and the remaining light golden oil was chromatographed on silica gel (1:1, Hexane/EtOAc) to give 2.9 g of dibenzyl 2-[[bis(benzyloxy)phosphoryl]methyl]pentanedioate as a clear and colorless oil. TLC R$f$0.5 (1:1 Hexane/EtOAc).

$^1$H NMR (CDCl$_3$) 7.1–7.4 (m, 20H), 5.05 (s, 2H), 4.8–5.03 (m, 6H), 2.8 (1H), 2.22–2.40 (m, 3H), 1.80–2.02 (m, 3H).

EXAMPLE 14

Preparation of 2-(phosphonomethyl)pentanedioic acid (Compound 3) Using Scheme III Benzyl pentanedioate 2(2.9 g, 4.9 mmol) was added to a mixture of 20 ml of methanol containing 0.29 g (6 mol %) of 10% Pd/C. This mixture was hydrogenated at 40 psi for 24 hours, filtered and evaporated to give 3(1.0 g, 90%) as a clear slightly golden viscous oil.

$^1$H NMR (D$_2$O): 2.6–2.78 (m, 1H), 2.25–2.40 (m, 2H), 1.75–2.15 (m, 4H).

EXAMPLE 15

A patient is at risk of injury from an ischemic event. The patient may be pretreated with an effective amount of a NAALADase inhibitor or a pharmaceutical composition of the present invention. It is expected that after the pretreatment, the patient would be protected from any injury due to the ischemic event.

EXAMPLE 16

A patient is suffering from an ischemic event. The patient may be administered during or after the event, an effective amount of a NAALADase inhibitor or a pharmaceutical composition of the present invention. It is expected that after the treatment, the patient would recover or would not suffer any significant injury due to the ischemic event.

EXAMPLE 17

A patient has suffered injury from an ischemic event. The patient may be administered an effective amount of a NAALADase inhibitor or a pharmaceutical composition of the present invention. It is expected that after the treatment, the patient would recover from the injury due to the ischemic event.

EXAMPLE 18

A patient is suffering from a glutamate abnormality. The patient may then be administered an effective amount of a NAALADase inhibitor or a pharmaceutical composition of the present invention. It is expected that after the treatment, the patient would be protected from further injury due to the glutamate abnormality or would recover from the glutamate abnormality.

EXAMPLE 19

A patient is suffering from or has suffered from a nervous insult, such as that arising from a neurodegenerative disease or a neurodegenerative process. The patient may then be administered an effective amount of a NAALADase inhibitor or a pharmaceutical composition of the present invention. It is expected that after the treatment, the patient would be protected from further injury due to the nervous insult or would recover from the nervous insult.

EXAMPLE 20

A patient is suffering from Parkinson's disease. The patient may then be administered an effective amount of a NAALADase inhibitor or a pharmaceutical composition of the present invention. It is expected that after the treatment, the patient would be protected from further neurodegeneration or would recover from Parkinson's disease.

EXAMPLE 21

A patient is suffering from ALS. The patient may then be administered an effective amount of a NAALADase inhibitor or a pharmaceutical composition of the present invention. It is expected that after the treatment, the patient would be protected from further neurodegeneration or would recover from ALS.

EXAMPLE 22

A patient is suffering from epilepsy. The patient may then be administered an effective amount of a NAALADase inhibitor or a pharmaceutical composition of the present invention. It is expected that after the treatment, the patient would be protected from further neurodegeneration or would recover from epilepsy.

EXAMPLE 23

A patient is suffering from abnormalities in myelination/demyelination processes. The patient may then be administered an effective amount of a NAALADase inhibitor or a pharmaceutical composition of the present invention. It is expected that after the treatment, the patient would be protected from further neurodegeneration or would recover from the abnormalities in myelination/demyelination processes.

EXAMPLE 24

A patient is suffering from or has suffered from a cerebrovascular accident, such as stroke. The patient may then be administered an effective amount of a NAALADase inhibitor or a pharmaceutical composition of the present invention. It is expected that after the treatment, the patient would be protected from or would recover from any injury due to the cerebrovascular accident.

EXAMPLE 25

A patient is suffering from a head trauma. The patient may then be administered an effective amount of a NAALADase inhibitor or a pharmaceutical composition of the present invention. It is expected that after the treatment, the patient would be protected from or would recover from any ischemic brain, spinal or peripheral injury resulting from the head trauma.

EXAMPLE 26

A patient is suffering from a spinal trauma. The patient may then be administered an effective amount of a NAALADase inhibitor or a pharmaceutical composition of the present invention. It is expected that after the treatment, the patient would be protected from or would recover from any ischemic injury resulting from the spinal trauma.

EXAMPLE 27

A patient is about to undergo surgery. The patient may be administered an effective amount of a NAALADase inhibitor or a pharmaceutical composition of the present invention. It is expected that after the treatment, the patient would not develop any ischemic brain, spinal or peripheral injury resulting from or associated with the surgery.

EXAMPLE 28

A patient is suffering from focal ischemia, such as that associated with thromboembolytic occlusion of a cerebral vessel, traumatic head injury, edema or brain tumors. The patient may then be administered an effective amount of a NAALADase inhibitor or a pharmaceutical composition of the present invention. It is expected that after the treatment, the patient would be protected from or would recover from any brain, spinal or peripheral injury resulting from the focal ischemia.

EXAMPLE 29

A patient is suffering from global ischemia. The patient may then be administered an effective amount of a NAALADase inhibitor or a pharmaceutical composition of the present invention. It is expected that after the treatment, the patient would be protected from or would recover from any brain, spinal or peripheral injury resulting from the global ischemia.

EXAMPLE 30

A patient is suffering from a cardiac arrest. The patient may then be administered an effective amount of a NAALADase inhibitor or a pharmaceutical composition of the present invention. It is expected that after the treatment, the patient would be protected from or would recover from any ischemic brain, spinal or peripheral injury associated with the cardiac arrest.

EXAMPLE 31

A patient is suffering from hypoxia, asphyxia or perinatal asphyxia. The patient may then be administered an effective amount of a NAALADase inhibitor or a pharmaceutical composition of the present invention. It is expected that after the treatment, the patient would be protected from or would recover from any ischemic brain, spinal or peripheral injury associated with the hypoxia, asphyxia or perinatal asphyxia.

EXAMPLE 32

A patient is suffering from a cerebro-cortical injury. The patient may then be administered an effective amount of a NAALADase inhibitor or a pharmaceutical composition of the present invention. It is expected that after the treatment, the patient would be protected from or would recover from any ischemic brain injury resulting from the cerebro-cortical injury.

EXAMPLE 33

The patient is suffering from an injury to the caudate nucleus. The patient may then be administered an effective amount of a NAALADase inhibitor or a pharmaceutical composition of the present invention. It is expected that after the treatment, the patient would be protected from or would recover from any ischemic brain injury resulting from the injury to the caudate nucleus.

EXAMPLE 34

A patient is diagnosed with a condition as identified in these examples. An effective amount of a NAALADase inhibitor or a pharmaceutical composition of the present invention may then be administered to the patient intravenously, intramuscularly, intraventricularly to the brain, rectally, subcutaneously, intranasally, through a catheter with or without a pump, orally, through a transdermal patch, topically, or through a polymer implant. After the treatment, the patient's condition would be expected to improve.

EXAMPLE 35

A patient is diagnosed with a condition as identified in these examples. A NAALADase inhibitor or a pharmaceutical composition of the present invention may then be administered to the patient in the form of a 100 mg/kg bolus, optionally followed by a 20 mg/kg per hour intravenous infusion over a two-hour period. After the treatment, the patient's condition would be expected to improve.

EXAMPLE 36

A patient is suffering from a cortical injury due to a condition identified in these examples. The patient may then be administered an effective amount of a NAALADase inhibitor or a pharmaceutical composition of the present invention. It is expected that after the treatment, the patient would be protected from further injury, or would exhibit at least 65% to at least 80% recovery from the cortical injury.

EXAMPLE 37

A patient is suffering from multiple sclerosis. The patient may then be administered an effective amount of a NAALADase inhibitor or a pharmaceutical composition of the present invention. It is expected that after the treatment, the patient would be protected from further demyelination or would recover from multiple sclerosis.

EXAMPLE 38

A patient is suffering from a peripheral neuropathy caused by Guillain-Barre syndrome. The patient may then be administered an effective amount of a NAALADase inhibitor or a pharmaceutical composition of the present invention. It is expected that after the treatment, the patient would be protected from further demyelination or would recover from the peripheral neuropathy.

The invention being thus described, it will be obvious that the same may be varied in many ways. Such variations are not to be regarded as a departure from the spirit and scope of the invention and all such modifications are intended to be included within the scope of the following claims.

We claim:

1. A method of treating a glutamate abnormality in an animal, comprising administering an effective amount of a NAALADase inhibitor to said animal, provided that said NAALADase inhibitor is neither quisqualic acid nor beta-NAAG.

2. The method of claim 1, wherein the glutamate abnormality is selected from the group consisting of stroke, Alzheimer's disease, Parkinson's Disease, Amyotrophic Lateral Sclerosis (ALS), Huntington's Disease, schizophrenia, chronic pain, ischemia, peripheral neuropathy, traumatic brain injury and physical damage to the spinal cord.

3. The method of claim 2, wherein the glutamate abnormality is stroke.

4. The method of claim 2, wherein the glutamate abnormality is Parkinson's Disease.

5. The method of claim 2, wherein the glutamate abnormality is Amyotrophic Lateral Sclerosis (ALS).

6. The method of claim 2, wherein the glutamate abnormality is ischemic spinal cord injury.

7. The method of claim 1, wherein the NAALADase inhibitor is administered in combination with at least one additional therapeutic agent.

8. The method of claim 1, wherein the NAALADase inhibitor is a glutamate-derived hydroxyphosphinyl derivative, an acidic peptide analog or a mixture thereof.

9. The method of claim 8, wherein the NAALADase inhibitor is an acidic peptide analog selected from the group consisting of Asp-Glu, Glu-Glu, Gly-Glu, gamma-Glu-Glu and Glu-Glu-Glu.

10. A method of treating a glutamate abnormality in an animal, comprising administering to said animal an effective amount compound of formula I:

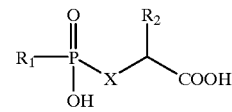

or a pharmaceutically acceptable salt or hydrate thereof, wherein:

$R_1$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_9$ alkoxy, $C_2$–$C_9$ alkenyloxy, phenoxy, benzyloxy, amino, Ar or mixtures thereof;

X is $CR_3R_4$, O or $NR_1$;

$R_3$ and $R_4$ are independently selected from the group consisting of hydrogen, $C_1$–$C_6$ straight or branched chain alkyl, $C_2$–$C_6$ straight or branched chain alkenyl, $C_3$–$C_8$ cycloalkyl, $C_5$–$C_7$ cycloalkenyl, Ar, halo and mixtures thereof;

$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl and Ar, wherein said $R_2$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, Ar or mixtures thereof;

Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, benzyl and phenyl, wherein said Ar is unsubstituted or substituted with halo, hydroxy, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino or mixtures thereof.

11. The method of claim 10, wherein X is $CH_2$.

12. The method of claim 11, wherein $R_2$ is substituted with carboxy.

13. The method of claim 12, wherein:

$R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof; and $R_2$ is $C_1$–$C_2$ alkyl.

14. The method of claim 13, wherein the glutamate-derived hydroxyphosphinyl derivative is selected from the group consisting of:
2-(phosphonomethyl)pentanedioic acid;
2-(phosphonomethyl)succinic acid;
2-[[(2-carboxyethyl)hydroxyphosphinyl]methyl] pentanedioic acid;
2-[[methylhydroxyphosphinyl]methyl]pentanedioic acid;
2-[[ethylhydroxyphosphinyl]methyl]pentanedioic acid;
2-[[propylhydroxyphosphinyl]methyl]pentanedioic acid;
2-[[butylhydroxyphosphinyl]methyl]pentanedioic acid;
2-[[cyclohexylhydroxyphosphinyl]methyl]pentanedioic acid;
2-[[(cyclohexyl)methylhydroxyphosphinyl]methyl] pentanedioic acid;
2-[[phenylhydroxyphosphinyl]methyl]pentanedioic acid;
2-[(benzylhydroxyphosphinyl)methyl]pentanedioic acid;
2-[[(phenylmethyl)hydroxyphosphinyl]methyl]pentanedioic acid;
2-[[(phenylethyl)hydroxyphosphinyl]methyl]pentanedioic acid;
2-[[(phenylpropyl)hydroxyphosphinyl]methyl]pentanedioic acid;
2-[[(phenylbutyl)hydroxyphosphinyl]methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(methoxybenzyl)hydroxyphosphinyl]methyl] pentanedioic acid;
2-[[(2,3,4-trimethoxyphenyl)hydroxyphosphinyl]methyl] pentanedioic acid;
2-[[(phenylprop-2-enyl)hydroxyphosphinyl]methyl] pentanedioic acid;
2-[[(2-fluorobenzyl)hydroxyphosphinyl]methyl] pentanedioic acid;
2-[[((hydroxy)phenylmethyl)hydroxyphosphinyl]methyl] pentanedioic acid;
2-[[(3-methylbenzyl)hydroxyphosphinyl]methyl] pentanedioic acid;
2-[[(4-fluorophenyl)hydroxyphosphinyl]methyl] pentanedioic acid;
2-[[(3-trifluoromethylbenzyl)hydroxyphosphinyl]methyl] pentanedioic acid; and pharmaceutically acceptable salts and hydrates thereof.

15. The method of claim 14, wherein the glutamate-derived hydroxyphosphinyl derivative is selected from the group consisting of:
2-(phosphonomethyl)pentanedioic acid;
2-(phosphonomethyl)succinic acid;
2-[[(2-carboxyethyl)hydroxyphosphinyl]methyl] pentanedioic acid;
2-[(benzylhydroxyphosphinyl)methyl]pentanedioic acid;
2-[(phenylhydroxyphosphinyl)methyl]pentanedioic acid;
2-[[((hydroxy)phenylmethyl)hydroxyphosphinyl]methyl] pentanedioic acid;
2-[(butylhydroxyphosphinyl)methyl]pentanedioic acid;
2-[[(3-methylbenzyl)hydroxyphosphinyl]methyl] pentanedioic acid;
2-[(3-phenylpropylhydroxyphosphinyl)methyl]pentanedioic acid;
2-[[(4-fluorophenyl)hydroxyphosphinyl]methyl] pentanedioic acid;
2-[(methylhydroxyphosphinyl)methyl]pentanedioic acid;
2-[(phenylethylhydroxyphosphinyl)methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(4-methoxybenzyl)hydroxyphosphinyl]methyl] pentanedioic acid;
2-[[(3-trifluoromethylbenzyl)hydroxyphosphinyl]methyl] pentanedioic acid;
2-[[(2-fluorobenzyl)hydroxyphosphinyl]methyl] pentanedioic acid;
2-[[(pentafluorobenzyl)hydroxyphosphinyl]methyl] pentanedioic acid;
2-[[(phenylprop-2-enyl)hydroxyphosphinyl]methyl] pentanedioic acid;
2-[[(aminomethyl)hydroxyphosphinyl]methyl]pentanedioic acid;
2-[[(aminoethyl)hydroxyphosphinyl]methyl]pentanedioic acid;
2-[[(aminopropyl)hydroxyphosphinyl]methyl]pentanedioic acid; and
pharmaceutically acceptable salts and hydrates thereof.

16. The method of claim 15, wherein the glutamate-derived hydroxyphosphinyl derivative is 2-(phosphonomethyl)pentanedioic acid or a pharmaceutically acceptable salt or hydrate thereof.

17. The method of claim 12, wherein:

$R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof; and $R_2$ is $C_3$–$C_9$ alkyl.

18. The method of claim 17, wherein the glutamate-derived hydroxyphosphinyl derivative is selected from the group consisting of:

2-[(methylhydroxyphosphinyl)methyl]hexanedioic acid;
2-[(benzylhydroxyphosphinyl)methyl]hexanedioic acid;
2-[(methylhydroxyphosphinyl)methyl]heptanedioic acid;
2-[(benzylhydroxyphosphinyl)methyl]heptanedioic acid;
2-[(methylhydroxyphosphinyl)methyl]octanedioic acid;
2-[(benzylhydroxyphosphinyl)methyl]octanedioic acid;
2-[(methylhydroxyphosphinyl)methyl]nonanedioic acid;
2-[(benzylhydroxyphosphinyl)methyl]nonanedioic acid;
2-[(methylhydroxyphosphinyl)methyl]decanedioic acid;
2-[(benzylhydroxyphosphinyl)methyl]decanedioic acid; and
  pharmaceutically acceptable salts and hydrates thereof.

19. The method of claim 12, wherein $R_1$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl or $C_1$–$C_4$ straight or branched chain alkyl substituted with 2-indolyl, 3-indolyl, 4-indolyl, 2-furyl, 3-furyl, tetrahydrofuranyl, 2-thienyl, 3-thienyl, 2-pyridyl, 3-pyridyl or 4-pyridyl.

20. The method of claim 19, wherein the glutamate-derived hydroxyphosphinyl derivative is selected from the group consisting of:

2-[[(2-pyridyl)methylhydroxyphosphinyl]methyl] pentanedioic acid;
2-[[(3-pyridyl)methylhydroxyphosphinyl]methyl] pentanedioic acid;
2-[[(4-pyridyl)methylhydroxyphosphinyl]methyl] pentanedioic acid;
2-[[(3-pyridyl)ethylhydroxyphosphinyl]methyl] pentanedioic acid;
2-[[(3-pyridyl)propylhydroxyphosphinyl]methyl] pentanedioic acid;
2-[[(tetrahydrofuranyl)methylhydroxyphosphinyl]methyl] pentanedioic acid;
2-[[(tetrahydrofuranyl)ethylhydroxyphosphinyl]methyl] pentanedioic acid;
2-[[(tetrahydrofuranyl)propylhydroxyphosphinyl]methyl] pentanedioic acid;
2-[[(2-tetrahydropyranyl)hydroxyphosphinyl]methyl] pentanedioic acid;
2-[[(3-tetrahydropyranyl)hydroxyphosphinyl]methyl] pentanedioic acid;
2-[[(4-tetrahydropyranyl)hydroxyphosphinyl]methyl] pentanedioic acid;
2-[[(2-indolyl)methylhydroxyphosphinyl]methyl] pentanedioic acid;
2-[[(3-indolyl)methylhydroxyphosphinyl]methyl] pentanedioic acid;
2-[[(4-indolyl)methylhydroxyphosphinyl]methyl] pentanedioic acid;
2-[[(3-indolyl)ethylhydroxyphosphinyl]methyl] pentanedioic acid;
2-[[(3-indolyl)propylhydroxyphosphinyl]methyl] pentanedioic acid;
2-[[(2-thienyl)methylhydroxyphosphinyl]methyl] pentanedioic acid;
2-[[(3-thienyl)methylhydroxyphosphinyl]methyl] pentanedioic acid;
2-[[(4-thienyl)methylhydroxyphosphinyl]methyl] pentanedioic acid;
2-[[(3-thienyl)ethylhydroxyphosphinyl]methyl] pentanedioic acid;
2-[[(3-thienyl)propylhydroxyphosphinyl]methyl] pentanedioic acid;
2-[[(2-pyridyl)hydroxyphosphinyl]methyl]pentanedioic acid;
2-[[(3-pyridyl)hydroxyphosphinyl]methyl]pentanedioic acid;
2-[[(4-pyridyl)hydroxyphosphinyl]methyl]pentanedioic acid;
2-[[(tetrahydrofuranyl)hydroxyphosphinyl]methyl] pentanedioic acid;
2-[[(2-indolyl)hydroxyphosphinyl]methyl]pentanedioic acid;
2-[[(3-indolyl)hydroxyphosphinyl]methyl]pentanedioic acid;
2-[[(4-indolyl)hydroxyphosphinyl]methyl]pentanedioic acid;
2-[[(2-thienyl)hydroxyphosphinyl]methyl]pentanedioic acid;
2-[[(3-thienyl)hydroxyphosphinyl]methyl]pentanedioic acid;
2-[[(4-thienyl)hydroxyphosphinyl]methyl]pentanedioic acid; and
pharmaceutically acceptable salts and hydrates thereof.

21. The method of claim 12, wherein $R_1$ is 1-naphthyl, 2-naphthyl, or $C_1$–$C_4$ straight or branched chain alkyl substituted with 1-naphthyl or 2-naphthyl.

22. The method of claim 21, wherein the glutamate-derived hydroxyphosphinyl derivative is selected from the group consisting of:

2-[[(1-naphthyl)hydroxyphosphinyl]methyl]pentanedioic acid;
2-[[(2-naphthyl)hydroxyphosphinyl]methyl]pentanedioic acid;
2-[[(1-naphthyl)methylhydroxyphosphinyl]methyl] pentanedioic acid;
2-[[(2-naphthyl)methylhydroxyphosphinyl]methyl] pentanedioic acid;
2-[[(1-naphthyl)ethylhydroxyphosphinyl]methyl] pentanedioic acid;
2-[[(2-naphthyl)ethylhydroxyphosphinyl]methyl] pentanedioic acid;
2-[[(1-naphthyl)propylhydroxyphosphinyl]methyl] pentanedioic acid;
2-[[(2-naphthyl)propylhydroxyphosphinyl]methyl] pentanedioic acid;
2-[[(1-naphthyl)butylhydroxyphosphinyl]methyl] pentanedioic acid;
2-[[(2-naphthyl)butylhydroxyphosphinyl]methyl] pentanedioic acid; and
pharmaceutically acceptable salts and hydrates thereof.

23. The method of claim 11, wherein:

$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

24. The method of claim 23, wherein:

$R_1$ is hydrogen, $C_1$–$C_4$ straight or branched chain alkyl, $C_2$–$C_4$ straight or branched chain alkenyl, $C_3$–$C_8$ cycloalkyl, $C_5$–$C_7$ cycloalkenyl, benzyl or phenyl, wherein said $R_1$ is unsubstituted or substituted with carboxy, $C_3$–$C_8$ cycloalkyl, $C_5$–$C_7$ cycloalkenyl, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, amino, benzyl, phenyl or mixtures thereof.

25. The method of claim 24, wherein the glutamate-derived hydroxyphosphinyl derivative is selected from the group consisting of:
3-(methylhydroxyphosphinyl)-2-phenylpropanoic acid;
3-(ethylhydroxyphosphinyl)-2-phenylpropanoic acid;
3-(propylhydroxyphosphinyl)-2-phenylpropanoic acid;
3-(butylhydroxyphosphinyl)-2-phenylpropanoic acid;
3-(cyclohexylhydroxyphosphinyl)-2-phenylpropanoic acid;
3-((cyclohexyl)methylhydroxyphosphinyl)-2-phenylpropanoic acid;
3-(phenylhydroxyphosphinyl)-2-phenylpropanoic acid;
3-(benzylhydroxyphosphinyl)-2-phenylpropanoic acid;
3-(phenylethylhydroxyphosphinyl)-2-phenylpropanoic acid;
3-(phenylpropylhydroxyphosphinyl)-2-phenylpropanoic acid;
3-(phenylbutylhydroxyphosphinyl)-2-phenylpropanoicacid;
3-((2,3,4-trimethoxyphenyl)-3-hydroxyphosphinyl)-2-phenylpropanoic acid;
3-(phenylprop-2-enylhydroxyphosphinyl)-2-phenylpropanoic acid;
3-(benzylhydroxyphosphinyl)-2-ethylpropanoic acid;
3-(benzylhydroxyphosphinyl)-2-propylpropanoic acid;
3-(benzylhydroxyphosphinyl)-2-butylpropanoic acid;
3-(benzylhydroxyphosphinyl)-2-cyclohexylpropanoic acid;
3-(benzylhydroxyphosphinyl)-2-(cyclohexyl)methylpropanoic acid;
3-(benzylhydroxyphosphinyl)-2-phenylpropanoic acid;
3-(benzylhydroxyphosphinyl)-2-benzylpropanoic acid;
3-(benzylhydroxyphosphinyl)-2-phenylethylpropanoicacid;
3-(benzylhydroxyphosphinyl)-2-phenylpropylpropanoic acid;
3-(benzylhydroxyphosphinyl)-2-phenylbutylpropanoicacid;
3-(benzylhydroxyphosphinyl)-2-(2,3,4-trimethoxyphenyl)propanoic acid;
3-(benzylhydroxyphosphinyl)-2-phenylprop-2-enylpropanoic acid; and
pharmaceutically acceptable salts and hydrates thereof.

26. The method of claim 11, wherein at least one of $R_1$ and $R_2$ is 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl, or $C_1$–$C_4$ straight or branched chain alkyl substituted with 2-indolyl 3-indolyl, 4-indolyl, 2-furyl, 3-furyl, tetrahydrofuranyl, 2-thienyl, 3-thienyl, 2-pyridyl, 3-pyridyl or 4-pyridyl.

27. The method of claim 26, wherein the glutamate-derived hydroxyphosphinyl derivative is selected from the group consisting of:
3-[(2-pyridyl)methylhydroxyphosphinyl]-2-phenylpropanoic acid;
3-[(3-pyridyl)methylhydroxyphosphinyl]-2-phenylpropanoic acid;
3-[(4-pyridyl)methylhydroxyphosphinyl]-2-phenylpropanoic acid;
3-[(3-pyridyl)ethylhydroxyphosphinyl]-2-phenylpropanoic acid;
3-[(3-pyridyl)propylhydroxyphosphinyl]-2-phenylpropanoic acid;
3-[(tetrahydrofuranyl)methylhydroxyphosphinyl]-2-phenylpropanoic acid;
3-[(tetrahydrofuranyl)ethylhydroxyphosphinyl]-2-phenylpropanoic acid;
3-[(tetrahydrofuranyl)propylhydroxyphosphinyl]-2-phenylpropanoic acid;
3-[(2-indolyl)methylhydroxyphosphinyl]-2-phenylpropanoic acid;
3-[(3-indolyl)methylhydroxyphosphinyl]-2-phenylpropanoic acid;
3-[(4-indolyl)methylhydroxyphosphinyl]-2-phenylpropanoic acid;
3-[(3-indolyl)ethylhydroxyphosphinyl]-2-phenylpropanoic acid;
3-[(3-indolyl)propylhydroxyphosphinyl]-2-phenylpropanoic acid;
3-[(2-thienyl)methylhydroxyphosphinyl]-2-phenylpropanoic acid;
3-[(3-thienyl)methylhydroxyphosphinyl]-2-phenylpropanoic acid;
3-[(4-thienyl)methylhydroxyphosphinyl]-2-phenylpropanoic acid;
3-[(3-thienyl)ethylhydroxyphosphinyl]-2-phenylpropanoic acid;
3-[(3-thienyl)propylhydroxyphosphinyl]-2-phenylpropanoic acid;
3-(benzylhydroxyphosphinyl)-2-(2-pyridyl)methylpropanoic acid;
3-(benzylhydroxyphosphinyl)-2-(3-pyridyl)methylpropanoic acid;
3-(benzylhydroxyphosphinyl)-2-(4-pyridyl)methylpropanoic acid;
3-(benzylhydroxyphosphinyl)-2-(3-pyridyl)ethylpropanoic acid;
3-(benzylhydroxyphosphinyl)-2-(3-pyridyl)propylpropanoic acid;
3-(benzylhydroxyphosphinyl)-2-(tetrahydrofuranyl)methylpropanoic acid;
3-(benzylhydroxyphosphinyl)-2-(tetrahydrofuranyl)ethylpropanoic acid;
3-(benzylhydroxyphosphinyl)-2-(tetrahydrofuranyl)propylpropanoic acid;
3-(benzylhydroxyphosphinyl)-2-(2-indolyl)methylpropanoic acid;
3-(benzylhydroxyphosphinyl)-2-(3-indolyl)methylpropanoic acid;
3-(benzylhydroxyphosphinyl)-2-(4-indolyl)methylpropanoic acid;
3-(benzylhydroxyphosphinyl)-2-(3-indolyl)ethylpropanoic acid;
3-(benzylhydroxyphosphinyl)-2-(3-indolyl)propylpropanoic acid;
3-(benzylhydroxyphosphinyl)-2-(2-thienyl)methylpropanoic acid;
3-(benzylhydroxyphosphinyl)-2-(3-thienyl)methylpropanoic acid;
3-(benzylhydroxyphosphinyl)-2-(4-thienyl)methylpropanoic acid;
3-(benzylhydroxyphosphinyl)-2-(3-thienyl)ethylpropanoic acid;
3-(benzylhydroxyphosphinyl)-2-(3-thienyl)propylpropanoic acid; and
pharmaceutically acceptable salts and hydrates thereof.

28. The method of claim 23, wherein $R_1$ is 1-naphthyl, 2-naphthyl, or $C_1$–$C_4$ straight or branched chain alkyl substituted with 1-naphthyl or 2-naphthyl.

29. The method of claim 28, wherein the glutamate-derived hydroxyphosphinyl derivative is selected from the group consisting of:
3-((1-naphthyl)hydroxyphosphinyl)-2-phenylpropanoic acid;
3-((2-naphthyl)hydroxyphosphinyl)-2-phenylpropanoic acid;
3-((1-naphthyl)methylhydroxyphosphinyl)-2-phenylpropanoic acid;

3-((2-naphthyl)methylhydroxyphosphinyl)-2-phenylpropanoic acid;
3-((1-naphthyl)ethylhydroxyphosphinyl)-2-phenylpropanoic acid;
3-((2-naphthyl)ethylhydroxyphosphinyl)-2-phenylpropanoic acid;
3-((1-naphthyl)propylhydroxyphosphinyl)-2-phenylpropanoic acid;
3-((2-naphthyl)propylhydroxyphosphinyl)-2-phenylpropanoic acid;
3-((1-naphthyl)butylhydroxyphosphinyl)-2-phenylpropanoic acid;
3-((2-naphthyl)butylhydroxyphosphinyl)-2-phenylpropanoic acid; and
pharmaceutically acceptable salts and hydrates thereof.

30. The method of claim 10, wherein X is O.

31. The method of claim 30, wherein $R_2$ is substituted with carboxy.

32. The method of claim 31, wherein the glutamate-derived hydroxyphosphinyl derivative is selected from the group consisting of:
2-[[methylhydroxyphosphinyl]oxy]pentanedioic acid;
2-[[ethylhydroxyphosphinyl]oxy]pentanedioic acid;
2-[[propylhydroxyphosphinyl]oxy]pentanedioic acid;
2-[[butylhydroxyphosphinyl]oxy]pentanedioic acid;
2-[[cyclohexylhydroxyphosphinyl]oxy]pentanedioic acid;
2-[[(cyclohexyl)methylhydroxyphosphinyl]oxy]pentanedioic acid;
2-[[phenylhydroxyphosphinyl]oxy]pentanedioic acid;
2-[[benzylhydroxyphosphinyl]oxy]pentanedioic acid;
2-[[phenylethylhydroxyphosphinyl]oxy]pentanedioic acid;
2-[[phenylpropylhydroxyphosphinyl]oxy]pentanedioic acid;
2-[[phenylbutylhydroxyphosphinyl]oxy]pentanedioic acid;
2-[[(4-methylbenzyl)hydroxyphosphinyl]oxy]pentanedioic acid;
2-[[(4-fluorobenzyl)hydroxyphosphinyl]oxy]pentanedioic acid;
2-[[(2-fluorobenzyl)hydroxyphosphinyl]oxy]pentanedioic acid;
2-[[(pentafluorobenzyl)hydroxyphosphinyl]oxy]pentanedioic acid;
2-[[(methoxybenzyl)hydroxyphosphinyl]oxy]pentanedioic acid;
2-[[(2,3,4-trimethoxyphenyl)hydroxyphosphinyl]oxy]pentanedioic acid;
2-[[(1-naphthyl)hydroxyphosphinyl]oxy]pentanedioic acid;
2-[[(2-naphthyl)hydroxyphosphinyl]oxy]pentanedioic acid;
2-[[(1-naphthyl)methylhydroxyphosphinyl]oxy]pentanedioic acid;
2-[[(2-naphthyl)methylhydroxyphosphinyl]oxy]pentanedioic acid;
2-[[(1-naphthyl)ethylhydroxyphosphinyl]oxy]pentanedioic acid;
2-[[(2-naphthyl)ethylhydroxyphosphinyl]oxy]pentanedioic acid;
2-[[(1-naphthyl)propylhydroxyphosphinyl]oxy]pentanedioic acid;
2-[[(2-naphthyl)propylhydroxyphosphinyl]oxy]pentanedioic acid;
2-[[(1-naphthyl)butylhydroxyphosphinyl]oxy]pentanedioic acid;
2-[[(2-naphthyl)butylhydroxyphosphinyl]oxy]pentanedioic acid;
2-[[(phenylprop-2-enyl)hydroxyphosphinyl]oxy]pentanedioic acid;
2-[[benzylhydroxyphosphinyl]oxy]pentanedioic acid;
2-[[((hydroxy)phenylmethyl)hydroxyphosphinyl]oxy]pentanedioic acid;
2-[[(3-methylbenzyl)hydroxyphosphinyl]oxy]pentanedioic acid;
2-[[(4-fluorophenyl)hydroxyphosphinyl]oxy]pentanedioic acid;
2-[[(2-fluorobenzyl)hydroxyphosphinyl]oxy]pentanedioic acid;
2-(phosphono)oxy]pentanedioic acid;
2-[[(3-trifluoromethylbenzyl)hydroxyphosphinyl]oxy]pentanedioic acid;
2-[[methylhydroxyphosphinyl]oxy]-2-phenylethanoic acid;
2-[[ethylhydroxyphosphinyl]oxy]-2-phenylethanoic acid;
2-[[propylhydroxyphosphinyl]oxy]-2-phenylethanoic acid;
2-[[butylhydroxyphosphinyl]oxy]-2-phenylethanoic acid;
2-[[cyclohexylhydroxyphosphinyl]oxy]-2-phenylethanoic acid;
2-[[(cyclohexyl)methylhydroxyphosphinyl]oxy]-2-phenylethanoic acid;
2-[[phenylhydroxyphosphinyl]oxy]-2-phenylethanoic acid;
2-[[benzylhydroxyphosphinyl]oxy]-2-phenylethanoic acid;
2-[[phenylethylhydroxyphosphinyl]oxy]-2-phenylethanoic acid;
2-[[phenylpropylhydroxyphosphinyl]oxy]-2-phenylethanoic acid;
2-[[phenylbutylhydroxyphosphinyl]oxy]-2-phenylethanoic acid;
2-[[(2,3,4-trimethoxyphenyl)-3-hydroxyphosphinyl]oxy]-2-phenylethanoic acid;
2-[[(1-naphthyl)hydroxyphosphinyl]oxy]-2-phenylethanoic acid;
2-[[(2-naphthyl)hydroxyphosphinyl]oxy]-2-phenylethanoic acid;
2-[[(1-naphthyl)methylhydroxyphosphinyl]oxy]-2-phenylethanoic acid;
2-[[(2-naphthyl)methylhydroxyphosphinyl]oxy]-2-phenylethanoic acid;
2-[[(1-naphthyl)ethylhydroxyphosphinyl]oxy]-2-phenylethanoic acid;
2-[[(2-naphthyl)ethylhydroxyphosphinyl]oxy]-2-phenylethanoic acid;
2-[[(1-naphthyl)propylhydroxyphosphinyl]oxy]-2-phenylethanoic acid;
2-[[(2-naphthyl)propylhydroxyphosphinyl]oxy]-2-phenylethanoic acid;
2-[[(1-naphthyl)butylhydroxyphosphinyl]oxy]-2-phenylethanoic acid;
2-[[(2-naphthyl)butylhydroxyphosphinyl]oxy]-2-phenylethanoic acid;
2-[[phenylprop-2-enylhydroxyphosphinyl]oxy]-2-phenylethanoic acid;
2-[(methylhydroxyphosphinyl)oxy]hexanedioic acid;
2-[(benzylhydroxyphosphinyl)oxy]hexanedioic acid;
2-[(methylhydroxyphosphinyl)oxy]heptanedioic acid;
2-[(benzylhydroxyphosphinyl)oxy]heptanedioic acid;
2-[(methylhydroxyphosphinyl)oxy]octanedioic acid;
2-[(benzylhydroxyphosphinyl)oxy]octanedioic acid;
2-[(methylhydroxyphosphinyl)oxy]nonanedioic acid;
2-[(benzylhydroxyphosphinyl)oxy]nonanedioic acid;
2-[(methylhydroxyphosphinyl)oxy]decanedioic acid;
2-[(benzylhydroxyphosphinyl)oxy]decanedioic acid;
2-[[benzylhydroxyphosphinyl]oxy]-2-methylethanoic acid;
2-[[benzylhydroxyphosphinyl]oxy]-2-ethylethanoic acid;
2-[[benzylhydroxyphosphinyl]oxy]-2-propylethanoic acid;
2-[[benzylhydroxyphosphinyl]oxy]-2-butylethanoic acid;
2-[[benzylhydroxyphosphinyl]oxy]-2-cyclohexylethanoic acid;

2-[[benzylhydroxyphosphinyl]oxy]-2-(cyclohexyl)
methylethanoic acid;
2-[[benzylhydroxyphosphinyl]oxy]-2-phenylethanoic acid;
2-[[benzylhydroxyphosphinyl]oxy]-2-benzylethanoic acid;
2-[[benzylhydroxyphosphinyl]oxy]-2-phenylethylethanoic
acid;
2-[[benzylhydroxyphosphinyl]oxy]-2-phenylpropylethanoic
acid;
2-[[benzylhydroxyphosphinyl]oxy]-2-phenylbutylethanoic
acid;
2-[[benzylhydroxyphosphinyl]oxy]-2-(2,3,4-trimethoxyphenyl)ethanoic acid;
2-[[benzylhydroxyphosphinyl]oxy]-2-(1-naphthyl)ethanoic
acid;
2-[[benzylhydroxyphosphinyl]oxy]-2-(2-naphthyl)ethanoic
acid;
2-[[benzylhydroxyphosphinyl]oxy]-2-(1-naphthyl)
methylethanoic acid;
2-[[benzylhydroxyphosphinyl]oxy]-2-(2-naphthyl)
methylethanoic acid;
2-[[benzylhydroxyphosphinyl]oxy]-2-(1-naphthyl)
ethylethanoic acid;
2-[[benzylhydroxyphosphinyl]oxy]-2-(2-naphthyl)
ethylethanoic acid;
2-[[benzylhydroxyphosphinyl]oxy]-2-(1-naphthyl)
propylethanoic acid;
2-[[benzylhydroxyphosphinyl]oxy]-2-(2-naphthyl)
propylethanoic acid;
2-[[benzylhydroxyphosphinyl]oxy]-2-(1-naphthyl)
butylethanoic acid;
2-[[benzylhydroxyphosphinyl]oxy]-2-(2-naphthyl)
butylethanoic acid;
2-[[benzylhydroxyphosphinyl]oxy]-2-phenylprop-2-enylethanoic acid;
2-[[(2-pyridyl)methylhydroxyphosphinyl]oxy]pentanedioic
acid;
2-[[(3-pyridyl)methylhydroxyphosphinyl]oxy]pentanedioic
acid;
2-[[(4-pyridyl)methylhydroxyphosphinyl]oxy]pentanedioic
acid;
2-[[(3-pyridyl)ethylhydroxyphosphinyl]oxy]pentanedioic
acid;
2-[[(3-pyridyl)propylhydroxyphosphinyl]oxy]pentanedioic
acid;
2-[[(tetrahydrofuranyl)methylhydroxyphosphinyl]oxy]
pentanedioic acid;
2-[[(tetrahydrofuranyl)ethylhydroxyphosphinyl]oxy]
pentanedioic acid;
2-[[(tetrahydrofuranyl)propylhydroxyphosphinyl]oxy]
pentanedioic acid;
2-[[(2-indolyl)methylhydroxyphosphinyl]oxy]pentanedioic
acid;
2-[[(3-indolyl)methylhydroxyphosphinyl]oxy]pentanedioic
acid;
2-[[(4-indolyl)methylhydroxyphosphinyl]oxy]pentanedioic
acid;
2-[[(3-indolyl)ethylhydroxyphosphinyl]oxy]pentanedioic
acid;
2-[[(3-indolyl)propylhydroxyphosphinyl]oxy]pentanedioic
acid;
2-[[(2-thienyl)methylhydroxyphosphinyl]oxy]pentanedioic
acid;
2-[[(3-thienyl)methylhydroxyphosphinyl]oxy]pentanedioic
acid;
2-[[(4-thienyl)methylhydroxyphosphinyl]oxy]pentanedioic
acid;
2-[[(3-thienyl)ethylhydroxyphosphinyl]oxy]pentanedioic
acid;
2-[[(3-thienyl)propylhydroxyphosphinyl]oxy]pentanedioic
acid; and
pharmaceutically acceptable salts and hydrates thereof.

33. The method of claim 30, wherein:
$R_2$ is selected from the group consisting of hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, benzyl and phenyl, wherein said $R_2$ is unsubstituted or substituted with $C_3$–$C_8$ cycloalkyl, $C_5$–$C_7$ cycloalkenyl, $C_1$–$C_6$ straight or branched chain alkyl, $C_2$–$C_6$ straight or branched chain alkenyl, $C_1$–$C_4$ alkoxy, phenyl or mixtures thereof.

34. The method of claim 33, wherein the glutamate-derived hydroxyphosphinyl derivative is selected from the group consisting of:
2-[[(2-pyridyl)methylhydroxyphosphinyl]oxy]-2-phenylethanoic acid;
2-[[(3-pyridyl)methylhydroxyphosphinyl]oxy]-2-phenylethanoic acid;
2-[[(4-pyridyl)methylhydroxyphosphinyl]oxy]-2-phenylethanoic acid;
2-[[(3-pyridyl)ethylhydroxyphosphinyl]oxy]-2-phenylethanoic acid;
2-[[(3-pyridyl)propylhydroxyphosphinyl]oxy]-2-phenylethanoic acid;
2-[[(tetrahydrofuranyl)methylhydroxyphosphinyl]oxy]-2-phenylethanoic acid;
2-[[(tetrahydrofuranyl)ethylhydroxyphosphinyl]oxy]-2-phenylethanoic acid;
2-[[(tetrahydrofuranyl)propylhydroxyphosphinyl]oxy]-2-phenylethanoic acid;
2-[[(2-indolyl)methylhydroxyphosphinyl]oxy]-2-phenylethanoic acid;
2-[[(3-indolyl)methylhydroxyphosphinyl]oxy]-2-phenylethanoic acid;
2-[[(4-indolyl)methylhydroxyphosphinyl]oxy]-2-phenylethanoic acid;
2-[[(3-indolyl)ethylhydroxyphosphinyl]oxy]-2-phenylethanoic acid;
2-[[(3-indolyl)propylhydroxyphosphinyl]oxy]-2-phenylethanoic acid;
2-[[(2-thienyl)methylhydroxyphosphinyl]oxy]-2-phenylethanoic acid;
2-[[(3-thienyl)methylhydroxyphosphinyl]oxy]-2-phenylethanoic acid;
2-[[(4-thienyl)methylhydroxyphosphinyl]oxy]-2-phenylethanoic acid;
2-[[(3-thienyl)ethylhydroxyphosphinyl]oxy]-2-phenylethanoic acid;
2-[[(3-thienyl)propylhydroxyphosphinyl]oxy]-2-phenylethanoic acid;
2-[[benzylhydroxyphosphinyl]oxy]-2-(2-pyridyl)
methylethanoic acid;
2-[[benzylhydroxyphosphinyl]oxy]-2-(3-pyridyl)
methylethanoic acid;
2-[[benzylhydroxyphosphinyl]oxy]-2-(4-pyridyl)
methylethanoic acid;
2-[[benzylhydroxyphosphinyl]oxy]-2-(3-pyridyl)
ethylethanoic acid;
2-[[benzylhydroxyphosphinyl]oxy]-2-(3-pyridyl)
propylethanoic acid;
2-[[benzylhydroxyphosphinyl]oxy]-2-(tetrahydrofuranyl)
methylethanoic acid;
2-[[benzylhydroxyphosphinyl]oxy]-2-(tetrahydrofuranyl)
ethylethanoic acid;
2-[[benzylhydroxyphosphinyl]oxy]-2-(tetrahydrofuranyl)
propylethanoic acid;

2-[[benzylhydroxyphosphinyl]oxy]-2-(2-indolyl) methylethanoic acid;
2-[[benzylhydroxyphosphinyl]oxy]-2-(3-indolyl) methylethanoic acid;
2-[[benzylhydroxyphosphinyl]oxy]-2-(4-indolyl) methylethanoic acid;
2-[[benzylhydroxyphosphinyl]oxy]-2-(3-indolyl) ethylethanoic acid;
2-[[benzylhydroxyphosphinyl]oxy]-2-(3-indolyl) propylethanoic acid;
2-[[benzylhydroxyphosphinyl]oxy]-2-(2-thienyl) methylethanoic acid;
2-[[benzylhydroxyphosphinyl]oxy]-2-(3-thienyl) methylethanoic acid;
2-[[benzylhydroxyphosphinyl]oxy]-2-(4-thienyl) methylethanoic acid;
2-[[benzylhydroxyphosphinyl]oxy]-2-(3-thienyl) ethylethanoic acid;
2-[[benzylhydroxyphosphinyl]oxy]-2-(3-thienyl) propylethanoic acid; and
pharmaceutically acceptable salts and hydrates thereof.

35. The method of claim 10, wherein X is $NR_1$.

36. The method of claim 35, wherein $R_2$ is substituted with carboxy.

37. The method of claim 36, wherein the glutamate-derived hydroxyphosphinyl derivative is selected from the group consisting of:
2-[[methylhydroxyphosphinyl]amino]pentanedioic acid;
2-[[ethylhydroxyphosphinyl]amino]pentanedioic acid;
2-[[propylhydroxyphosphinyl]amino]pentanedioic acid;
2-[[butylhydroxyphosphinyl]amino]pentanedioic acid;
2-[[cyclohexylhydroxyphosphinyl]amino]pentanedioic acid;
2-[[(cyclohexyl)methylhydroxyphosphinyl]amino] pentanedioic acid;
2-[[phenylhydroxyphosphinyl]amino]pentanedioic acid;
2-[[benzylhydroxyphosphinyl]amino]pentanedioic acid;
2-[[phenylethylhydroxyphosphinyl]amino]pentanedioic acid;
2-[[phenylpropylhydroxyphosphinyl]amino]pentanedioic acid;
2-[[phenylbutylhydroxyphosphinyl]amino]pentanedioic acid;
2-[[(4-methylbenzyl)hydroxyphosphinyl]amino] pentanedioic acid;
2-[[(4-fluorobenzyl)hydroxyphosphinyl]amino] pentanedioic acid;
2-[[(2-fluorobenzyl)hydroxyphosphinyl]amino] pentanedioic acid;
2-[[(pentafluorobenzyl)hydroxyphosphinyl]amino] pentanedioic acid;
2-[[(methoxybenzyl)hydroxyphosphinyl]amino] pentanedioic acid;
2-[[(2,3,4-trimethoxyphenyl)hydroxyphosphinyl]amino] pentanedioic acid;
2-[[(1-naphthyl)hydroxyphosphinyl]amino]pentanedioic acid;
2-[[(2-naphthyl)hydroxyphosphinyl]amino]pentanedioic acid;
2-[[(1-naphthyl)methylhydroxyphosphinyl]amino] pentanedioic acid;
2-[[(2-naphthyl)methylhydroxyphosphinyl]amino] pentanedioic acid;
2-[[(1-naphthyl)ethylhydroxyphosphinyl]amino] pentanedioic acid;
2-[[(2-naphthyl)ethylhydroxyphosphinyl]amino] pentanedioic acid;
2-[[(1-naphthyl)propylhydroxyphosphinyl]amino] pentanedioic acid;
2-[[(2-naphthyl)propylhydroxyphosphinyl]amino] pentanedioic acid;
2-[[(1-naphthyl)butylhydroxyphosphinyl]amino] pentanedioic acid;
2-[[(2-naphthyl)butylhydroxyphosphinyl]amino] pentanedioic acid;
2-[[(phenylprop-2-enyl)hydroxyphosphinyl]amino] pentanedioic acid;
2-[[benzylhydroxyphosphinyl]amino]pentanedioic acid;
2-[[(2-fluorobenzyl)hydroxyphosphinyl]amino]-2- pentanedioic acid;
2-[[((hydroxy)phenylmethyl)hydroxyphosphinyl]amino] pentanedioic acid;
2-[[(3-methylbenzyl)hydroxyphosphinyl]amino] pentanedioic acid;
2-[[(4-fluorophenyl)hydroxyphosphinyl]amino] pentanedioic acid;
2-[(phosphono)amino]pentanedioic acid;
2-[[(3-trifluoromethylbenzyl)hydroxyphosphinyl]amino]- pentanedioic acid;
2-[(methylhydroxyphosphinyl)amino]hexanedioic acid;
2-[(benzylhydroxyphosphinyl)amino]hexanedioic acid;
2-[(methylhydroxyphosphinyl)amino]heptanedioic acid;
2-[(benzylhydroxyphosphinyl)amino]heptanedioic acid;
2-[(methylhydroxyphosphinyl)amino]octanedioic acid;
2-[(benzylhydroxyphosphinyl)amino]octanedioic acid;
2-[(methylhydroxyphosphinyl)amino]nonanedioic acid;
2-[(benzylhydroxyphosphinyl)amino]nonanedioic acid;
2-[(methylhydroxyphosphinyl)amino]decanedioic acid;
2-[(benzylhydroxyphosphinyl)amino]decanedioic acid;
3-[[(2-pyridyl)methylhydroxyphosphinyl]amino] pentanedioic acid;
3-[[(3-pyridyl)methylhydroxyphosphinyl]amino] pentanedioic acid;
3-[[(4-pyridyl)methylhydroxyphosphinyl]amino] pentanedioic acid;
3-[[(3-pyridyl)ethylhydroxyphosphinyl]amino]pentanedioic acid;
3-[[(3-pyridyl)propylhydroxyphosphinyl]amino] pentanedioic acid;
3-[[(tetrahydrofuranyl)methylhydroxyphosphinyl]amino] pentanedioic acid;
3-[[(tetrahydrofuranyl)ethylhydroxyphosphinyl]amino] pentanedioic acid;
3-[[(tetrahydrofuranyl)propylhydroxyphosphinyl]amino] pentanedioic acid;
3-[[(2-indolyl)methylhydroxyphosphinyl]amino] pentanedioic acid;
3-[[(3-indolyl)methylhydroxyphosphinyl]amino] pentanedioic acid;
3-[[(4-indolyl)methylhydroxyphosphinyl]amino] pentanedioic acid;
3-[[(3-indolyl)ethylhydroxyphosphinyl]amino]pentanedioic acid;
3-[[(3-indolyl)propylhydroxyphosphinyl]amino] pentanedioic acid;
3-[[(2-thienyl)methylhydroxyphosphinyl]amino] pentanedioic acid;
3-[[(3-thienyl)methylhydroxyphosphinyl]amino] pentanedioic acid;
3-[[(4-thienyl)methylhydroxyphosphinyl]amino] pentanedioic acid;

3-[[(3-thienyl)ethylhydroxyphosphinyl]amino]pentanedioic acid;

3-[[(3-thienyl)propylhydroxyphosphinyl]amino]pentanedioic acid; and pharmaceutically acceptable salts and hydrates thereof.

38. The method of claim 1, wherein the glutamate abnormality is epilepsy.

39. The method of claim 2, wherein the glutamate abnormality is schizophrenia.

40. The method of claim 2, wherein the glutamate abnormality is chronic pain.

* * * * *